US 7,737,178 B2

(12) United States Patent
Serhan et al.

(10) Patent No.: US 7,737,178 B2
(45) Date of Patent: Jun. 15, 2010

(54) ASPIRIN-TRIGGERED LIPID MEDIATORS

(75) Inventors: Charles N. Serhan, Needham, MA (US); Clary B. Clish, Medford, MA (US)

(73) Assignee: The Brigham and Woman's Hospital, Inc., Boston, MA (US)

( * ) Notice: Subject to any disclaimer, the term of this patent is extended or adjusted under 35 U.S.C. 154(b) by 0 days.

(21) Appl. No.: 12/338,240

(22) Filed: Dec. 18, 2008

(65) Prior Publication Data

US 2009/0149538 A1 Jun. 11, 2009

Related U.S. Application Data

(60) Continuation of application No. 11/334,330, filed on Jan. 18, 2006, which is a division of application No. 10/663,061, filed on Sep. 12, 2003, now Pat. No. 7,053,230, which is a division of application No. 09/785,866, filed on Feb. 16, 2001, now Pat. No. 6,670, 396.

(60) Provisional application No. 60/238,814, filed on Oct. 6, 2000, provisional application No. 60/183,078, filed on Feb. 16, 2000.

(51) Int. Cl.
C07C 57/03 (2006.01)
A61K 31/20 (2006.01)

(52) U.S. Cl. .................... 514/560; 554/115; 554/219; 554/224; 562/400; 562/512; 562/549; 562/560; 514/549; 514/552

(58) Field of Classification Search .............. 562/400, 562/512, 549, 579; 514/549, 552, 560; 554/115, 554/219, 224
See application file for complete search history.

(56) References Cited

U.S. PATENT DOCUMENTS

| 4,201,211 | A | 5/1980 | Chandrasekaran et al. |
| 4,442,099 | A | 4/1984 | Nicolau et al. |
| 4,567,290 | A | 1/1986 | Nicolau et al. |
| 4,576,758 | A | 3/1986 | Morris et al. |
| 4,666,701 | A | 5/1987 | Horrobin et al. |
| 4,710,521 | A | 12/1987 | Soukup et al. |
| 4,759,880 | A | 7/1988 | Nicolau et al. |
| 4,810,424 | A | 3/1989 | Gerwick et al. |
| 5,087,790 | A | 2/1992 | Petasis et al. |
| 5,136,501 | A | 8/1992 | Silverman et al. |
| 5,177,046 | A | 1/1993 | Savoca et al. |
| 5,409,955 | A | 4/1995 | Bockow et al. |
| 5,411,988 | A | 5/1995 | Bockow et al. |
| 5,441,951 | A | 8/1995 | Serhan |
| 5,594,732 | A | 1/1997 | Bell et al. |
| 5,604,258 | A | 2/1997 | Ferrante et al. |
| 5,648,512 | A | 7/1997 | Serhan |
| 5,650,157 | A | 7/1997 | Bockow |
| 5,709,855 | A | 1/1998 | Bockow et al. |
| 5,752,238 | A | 5/1998 | Dedrick |
| 5,756,789 | A | 5/1998 | Bruce et al. |
| 5,814,599 | A | 9/1998 | Mitragotri et al. |
| 5,842,040 | A | 11/1998 | Hughes et al. |
| 5,845,265 | A | 12/1998 | Woolston |
| 5,846,974 | A | 12/1998 | Kallman et al. |
| 5,861,399 | A | 1/1999 | Seed et al. |
| 5,870,717 | A | 2/1999 | Wiecha |
| 5,878,400 | A | 3/1999 | Carter, III |
| 5,878,423 | A | 3/1999 | Anderson et al. |
| 5,890,138 | A | 3/1999 | Godin et al. |
| 5,896,379 | A | 4/1999 | Haber |
| 5,912,006 | A | 6/1999 | Bockow et al. |
| 5,932,598 | A | 8/1999 | Talley et al. |
| 5,946,467 | A | 8/1999 | Pathakis et al. |
| 6,030,715 | A | 2/2000 | Thompson et al. |
| 6,030,917 | A | 2/2000 | Weinberg et al. |
| 6,048,897 | A | 4/2000 | Serhan |
| 6,069,109 | A | 5/2000 | Kao et al. |
| 6,117,911 | A | 9/2000 | Grainger et al. |
| 6,201,022 | B1 | 3/2001 | Mease et al. |
| 6,232,467 | B1 | 5/2001 | Petasis et al. |
| 6,259,699 | B1 | 7/2001 | Opalka et al. |
| 6,272,474 | B1 | 8/2001 | Garcia |
| 6,316,648 | B1 | 11/2001 | Serhan |
| 6,336,105 | B1 | 1/2002 | Conklin et al. |
| 6,336,138 | B1 | 1/2002 | Caswell et al. |
| 6,377,937 | B1 | 4/2002 | Paskowitz |
| 6,397,212 | B1 | 5/2002 | Biffar |
| 6,415,270 | B1 | 7/2002 | Rackson et al. |
| 6,427,132 | B1 | 7/2002 | Bowman-Amuah |

(Continued)

FOREIGN PATENT DOCUMENTS

EP 0736509 10/1996

(Continued)

OTHER PUBLICATIONS

"Scope and Editorial Policy", *Organometallics*, published by the American Chemical Society 21 (1) 2002, 13A, 14A.
"Epolinsatures", Bulletin De La Societe Chimique de France, No. 3, pp. 419-432, 1989.
XP002184773. Database WPI, Section Ch, Week 199334. Derwent Publications Ltd., London, GB; AN 1993-269748. (See also JP 05186342, Jul. 27, 1993).
Alami, et al., A Versatile Route to conjugated hydroxyl (e,z,e,e)—Tetraenoic acids: highly chemo-and stereoselective synthesis of lipoxin B4 Tetrahedro Asym., 8 (17) 1997, pp. 2949-2958.
Albert, C. M. et al., "Blood levels of long-chain n-e fatty acids and the risk of sudden death", *N. Engl. J. Med.*, vol. 346, 2002, pp. 1113-1118.

(Continued)

*Primary Examiner*—Shailendra Kumar
(74) *Attorney, Agent, or Firm*—Scott D. Rothenberger; Colin L. Fairman; Fulbright & Jaworski LLP

(57) ABSTRACT

Aspirin triggered lipid mediators (ATLMs) are disclosed which are useful for the treatment of prevention of inflammation associated with various diseases, including ischemia.

5 Claims, 51 Drawing Sheets

U.S. PATENT DOCUMENTS

| | | | |
|---|---|---|---|
| 6,428,990 B1 | 8/2002 | Mukerji et al. | |
| 6,569,075 B2 | 5/2003 | Serhan | |
| 6,602,817 B1 | 8/2003 | Petasis | |
| 6,620,919 B2 | 9/2003 | Serhan | |
| 6,635,776 B2 | 10/2003 | Serhan | |
| 6,653,493 B2 | 11/2003 | Serhan | |
| 6,670,396 B2 * | 12/2003 | Serhan et al. | 514/549 |
| 6,750,360 B2 | 6/2004 | Serhan | |
| 6,887,901 B1 | 5/2005 | Serhan | |
| 6,949,664 B2 | 9/2005 | Petasis | |
| 7,030,159 B2 * | 4/2006 | Serhan et al. | 514/560 |
| 7,053,230 B2 * | 5/2006 | Serhan et al. | 554/224 |
| 7,341,840 B2 | 3/2008 | Serhan et al. | |
| 2001/0023500 A1 | 9/2001 | Serhan | |
| 2001/0031882 A1 | 10/2001 | Serhan | |
| 2002/0010351 A1 | 1/2002 | Serhan | |
| 2002/0045579 A1 | 4/2002 | Madara et al. | |
| 2002/0055538 A1 | 5/2002 | Serhan et al. | |
| 2002/0055539 A1 | 5/2002 | Bockow et al. | |
| 2002/0082435 A1 | 6/2002 | Serhan | |
| 2002/0091279 A1 | 7/2002 | Serhan | |
| 2002/0094549 A1 | 7/2002 | Serhan et al. | |
| 2002/0107289 A1 | 8/2002 | Serhan | |
| 2002/0111505 A1 | 8/2002 | Serhan | |
| 2002/0120013 A1 | 8/2002 | Serhan | |
| 2002/0132847 A1 | 9/2002 | Serhan | |
| 2002/0143069 A1 | 10/2002 | Serhan | |
| 2002/0193431 A1 | 12/2002 | Serhan et al. | |
| 2003/0032827 A1 | 2/2003 | Serhan | |
| 2003/0055275 A1 | 3/2003 | Serhan | |
| 2003/0060512 A1 | 3/2003 | Madara et al. | |
| 2003/0069435 A1 | 4/2003 | Serhan | |
| 2003/0134901 A1 | 7/2003 | Serhan | |
| 2003/0166716 A1 | 9/2003 | Serhan et al. | |
| 2003/0191184 A1 | 10/2003 | Serhan et al. | |
| 2003/0191332 A1 | 10/2003 | Serhan | |
| 2003/0195248 A1 | 10/2003 | Serhan et al. | |
| 2003/0236423 A1 | 12/2003 | Petasis | |
| 2004/0019110 A1 | 1/2004 | Van Dyke et al. | |
| 2004/0044028 A1 | 3/2004 | Obukowicz | |
| 2004/0044050 A1 | 3/2004 | Goodman et al. | |
| 2004/0053998 A1 | 3/2004 | Serhan et al. | |
| 2004/0059144 A1 | 3/2004 | Serhan et al. | |
| 2004/0116408 A1 | 6/2004 | Serhan | |
| 2004/0151712 A1 | 8/2004 | Madara et al. | |
| 2004/0192785 A1 | 9/2004 | Serhan | |
| 2005/0075398 A1 | 4/2005 | Bazan et al. | |
| 2005/0228047 A1 | 10/2005 | Petasis | |
| 2005/0261255 A1 | 11/2005 | Serhan et al. | |
| 2006/0128804 A1 | 6/2006 | Serhan et al. | |
| 2006/0293288 A1 | 12/2006 | Serhan et al. | |
| 2008/0096961 A1 | 4/2008 | Serhan et al. | |

FOREIGN PATENT DOCUMENTS

| | | |
|---|---|---|
| GB | 2033745 | 5/1980 |
| JP | 5186342 | 7/1993 |
| WO | WO 91/16914 | 11/1991 |
| WO | WO 97/19415 | 5/1997 |
| WO | WO 98/19259 | 5/1998 |
| WO | WO 98/35469 | 8/1998 |
| WO | WO 98/46588 | 10/1998 |
| WO | WO 99/06913 | 2/1999 |
| WO | WO 99/13417 | 3/1999 |
| WO | WO 99/56727 | 11/1999 |
| WO | WO 00/32210 | 6/2000 |
| WO | WO 00/74632 | 12/2000 |
| WO | WO 01/60778 | 8/2001 |
| WO | WO 03/051350 | 6/2003 |
| WO | WO 03/053123 | 7/2003 |
| WO | WO 03/053423 | 7/2003 |
| WO | WO 03/084305 | 10/2003 |
| WO | WO 03/105776 | 12/2003 |
| WO | WO 2004/014835 | 2/2004 |
| WO | WO 2005/089744 | 9/2005 |

OTHER PUBLICATIONS

Arita et al., "Stereochemical Assignment, Antiinflammatory Properties, and Receptor for the Omega-3 Lipid Mediator Resolvin E1", *J. Exp. Med.* 201(5) 2005, 713-722.

Arita, et al., "Resolvin E1, An Endogenous Lipid Mediator Derived from Omega-3 Eicosapentaenoic Acid, Protects Against 2, 4,6-Trinitrobenzene Sulfonic Acid-induced Colitis", *Proc. Natl. Acad. Sci*, USA, 102(21) 2005, pp. 7671-7676.

Babine, R.E. and S.L. Bender., "Molecular Recognition of Protein-Ligand Complexes: Applications to Design", *Chem. Rev*, 97, 1997, pp. 1359-1472.

Bandeira-Mielo et al., "Cyclooxygenase-2 derived prostaglandin $E_2$ and lipoxin $A_4$ accelerate resolution of allergic edema in Antiostrongylus costaricensis-infected rats: relationship with concurrent eosinophilia", *J. Immunol.*, vol. 164, 2000, pp. 1029-1036.

Bannenberg, et al., "Molecular Circuits of Resolution: Formation and Actions of Resolvins and Protectins", *Immunol*. 174(7) 2005, pp. 4345-4355.

Bazan, et al., "Docosahexaneoic Acid (22:6, n-3) is metabolized to lipoxygenase reaction products in the retina", *Biochem. Biophys. Res. Comm.*, vol. 125, 1984, pp. 741-747.

Bazan et al., "Pathways for the uptake and conservation of docosahexaenoic acid in photoreceptors and synapses: biochemical and autoradiographic studies", *Can. J. Physiol. Pharmacol.*, vol. 71, 1993, pp. 690-698.

Beamer L.J. et al. "Crystal structure of Human BPI and two bound phospholipids at 2.4 angstrom resolution", *Science*, vol. 276, 1997, pp. 1861-1864.

Bhaley, G. et al., "Solid Phase Synthesis of Diverse Tetrahydro-1,4-Benzodiazepine-2-ones", *Tetrahedron Letters* 38(48) 1997, pp. 8375-8378.

Biliman et al., "Prevention of sudden cardiac death by dietary pure ω-3 polyunsaturated fatty acids in dogs", *Circulation 99* ,1999, pp. 2452-2457.

Blaser, E. et al., "Asymmetrix Steering of oxa Diels-Aider Reactions with Silyloxydienes Employing Proline Esters as Chiral Auxiliary Groups", *Eur. J. Org. Chem.*, 1999, pp. 329-333.

Boland et al., "Stereospecific Syntheses and Spectroscopis Properties of Isomeric 2,4,6,8- Undecatetraenes. New Hydrocarbons from the Marine Brown Alga Giffordia Mitchellae", *Helv. Chim. Acta* 70, 1987, pp. 1025-1040.

Booyens et al., "Some effects of the essential fatty acids linoleic acid and alpha-linolenic acid and of their metabolites gamma-linolenic acid, arachidonic acid, eicosapentaenoic acid docosahexaenoic acid, and of prostaglandins A1 and e1 on the proliferation of human osteogenic sarcoma cells in culture", *Prostoglandins Leukot. Med.*, vol. 15, 1984, pp. 15-33.

Buchanan et al., "Regulation of endothelial cell and platelet receptor-ligand binding by the 12- and 15-lipoxygenase monohydroxides, 12-, 15-HETE and 13-HODE", Prostaglandins Leukot. Essent. Fatty Acids, 1998, pp. 339-346.

Canny, G. et al., "Lipid mediator-induced expression of bactericidal/permeability-increasing protein (BPI) in human mucosal epithelia", *Proc. Natl. Acad., Sci., USA*, vol. 99, No. 6, 2002, pp. 3902-3907.

Capdevila et al., "The highly stereoselective oxidation of polyunsaturated fatty acids by cytochrome P450BM-3", J. Biol. Chem., 1996, pp. 22663-22671.

Catelia-Lawson et al., "Cycloxygenase inhibitors and the antiplatelet effects of aspirin", *N. Engl. J. Med.*, vol. 345, 2001, pp. 1809-1817.

Chiang et al., "Aspirin-triggered 15-epi-lipoxin A4 (ATL) generation by human leukocytes and murine peritonitis exudates: Development of a specific 15-epi-LXA4 Elisa", J. Pharmacol. Exp. Ther., 1998, pp. 779-790.

Chiang et al., "Leukotriene B4 receptor transgenic mice reveal novel protective roles for lipoxins and aspirin-triggered lipoxins in reperfusion", *J. Clin. Invest.*, 1999, pp. 309-316.

Claria et al., "Aspirin triggers previously undescribed bioactive eicosanoids by human endothelial cell-leukocyte interactions", *Proc. Natl. Acad. Sci., USA*, 1995, pp. 9475-9479.

Clish et al., "Oxidoreductases in lipoxin $A_4$ metabolic inactivation", *J. Biol. Chem.*, vol. 375, 2000, pp. 25372-25380.

Colgan, S.P .et al., "Defective in vitro motility of polymorphonuclear leuocytes of homozygote and heterozygote Chediak-Higashi cats", *Vet Immunol. Immunopathology*, 1992, pp. 205-227.

Colgan et al., "Lipoxin $A_4$ modulates transmigration of human neutrophils across intestinal epithelial monolayers", *J. Clin. Invest.*, vol. 92,1993, pp. 75-82.

Cooper, S.F., et al., "Identification of Antibacterial Fatty Acids from Phaeodactylum tricomtum grown in dialysis culture", The Faculty Press, 1985, pp. 28-36.

Corey, E. J. et al., "Docosahexaaenoic acid is a strong inhibitor of prostaglandin but not leukotriene biosynthesis", *Proc. Natl. Acad. Sci. USA*, vol. 80, 1983, pp. 3581-3584.

Crofford. "Rational use of analgesic and anti-inflammatory drugs", *N. Engl. J. Med.*, vol. 345, 2001, pp. 1844-1846.

Cronstein et al., "A mechanism for the anti-inflammatory effects of corticosteriods: The glucocorticold receptor regulates leukocyte adhesion to endothelial cells and expression of endothelial-leukocyte adhesion molecule 1 and intercellular adhesion molecule 1", Proc. Natl. Acad. Sci. 1992, pp. 9991-9995.

Croset, M. et al., "Inhibition by Lipoxygenase Products of TXA2-Like Responses of Platelets and Vascular Smooth Muscle", Biochemical Pharmacology, vol. 37, No. 7, 1988, pp. 1275-1280, XP002445509.

De Caterina et al., "n-e Fatty Acids and Vascular Disease", *Current Topics in Cardiovascular Disease*, Springer-Verlag, London, 1993.

De Montarby, L. et al., "Syntheses stereoselective de metabolites hydroxyles d'acides gras polyinsatures", Bulletin DeLa Societe Chimique De France, Societe Francaise De Chimie. Paris, FR, No. 3, 1989, pp. 419-432, XP00220024.

Dharmsathaphorn, K. et al., "Established intestinal cell lines as model systems for electrolyte transport studies", *Methods in Enzymology*, vol. 192, 1990, pp. 354-389.

Dioux, Laurent and Morris Srebnik, "Asymmetric Boron-Catalyzed Reactions", *Chem Rev.* 93, 1993, pp. 763-784.

Drazen et al., "Heterogeneity of therapeutic responses in asthma", Br. Med. Bull., vol. 56, 2000, pp. 1054-1070.

Durantel et al., "Study of the mechanism of Antiviral Action of Iminosugar Derivatives against Bovine Viral Diarrhea Virus", *J. Virology* 75 (19) 2001, pp. 8987-8998.

Eckmann, L. et al., "Epithelial cell secrete the chemokines interleukin-8 in response to bacterial entry", *Infection and Immunity*, vol. 61, No. 11, 1993, pp. 4569-4574.

Elsbach, P. et al., "Role of the bactericidal/permeability-increasing protein in host defence", Current Opinion in Immunology, vol. 10, No. 1, 1998, pp. 45-49.

Eritsland et al., "Effects of Highly Concentrated Omega-3 PUF As and Acetylsalicylic Acid, Alone and Combined, on Bleeding Time and Serum Liquid Profile", *J. Oslo City Hosp.*, vol. 39 (8-9) 1989, pp. 97-101.

Evans, B.E. et al., "Design of Nonpetidal ligands for a Peptide Receptor: Cholecystokinin Antagonists", *J. Med. Chem.* 30, 1987, pp. 1229-1239.

Fischer et al., "Uptake, release and metabolism of docosahexaenoic acid (DHA, C22:6w3) in human platelets and neutrophils", *Biochem, Blophys. RES. Commun.*, vol. 120, 1984, pp. 907-918.

Fletcher, M.D. and M.C. Campbell, "Partially Modified Retro-Inverso Peptides: Development, Sythesis, and Conformational Behavior", *Chem. Rev.*, 98, 1998, pp. 763-795.

Fored et al., "Acetaminophen, aspirin, and chronic renal failure", *N. Engl. J. Med.*

Freedman et al., "Characterization of LPS-induced lung inflammation in cftr mice and the effect of docosahexaenoic acid", *J. Appl. Physiol.* vol. 92, 2002, pp. 2169-2176.

Ganz T. et al., "Antimicrobial peptides of phagocytes and epithelia", Seminars in Hematology, vol. 34, No. 4, 1997, pp. 343-354.

Garcia-Cardena et al., "Biomechanical activation of cascular endothelium as a determinant of its functional phenotype", *Proc. Natl. Acad. Sci. USA*, vol. 98, 2001, pp. 4478-4485.

Garro-Hellon et al., "Mild and selective Palladium (0)-Catalyzed Deallylation of Allylic Amines, Allylamine and Diallylamines as Very Convenient Ammonia Equivalents for the Synthesis of Primary Amines", *J. Org. Chem.* 58, 1993, pp. 6109-6113.

George et al., "Expression purification and characterization of recombinant human inductible prostaglandin G/H synthase from baculovirus-infected insect cells", Protein Expres. Purif., 1996, pp. 19-26.

Gilroy et al., "Inducible cyclooxygenase may have anti-inflammatory properties", *Nature Med.*, vol. 5, 1999, pp. 698-701.

GISSI-Preventive Investigators, "Dietary supplementation with n-3 polyunsaturated fatty acids and vitamin E after myocardial infarction: Results of the GISSI-Prevenzione trial", *Lancet*, vol. 354, 1999, pp. 447-455.

Golebiowski, A. and J. Jurczak, "Alpha-Amino-Beta-Hydroxy Acids in the Total Synthesis of Amino Sugars", *Synlett*, Apr. 1993, pp. 241-245.

Greeling et al., "Fat intake and fatty acid profile in plasma phospholipids and adipose tissue in patients with Crohn's disease, compared with controls", *Am. J. Gastroenterol.*, vol. 94, 1999, pp. 410-417.

Gronert, et al., "Transcellular regulation of eicosanoid biosynthesis", Eicosanoid Protocols 1999, pp. 119-144.

Guilier et al., "Linkers and Cleavage Stategies in Solid Phase Organic Synthesis and Combinatorial Chemistry", *Chem. Rev.*, 100, 2000, pp. 2091-2157.

Gum et al., "Aspirin use and all-cause mortality among patients being valuated for known or suspected coronary artery disease: a propensity analysis", *J.A.M.A.*, vol. 286, 2001, pp. 1187-1194.

Gunstone et al., "The Lipid Handbook", 2$^{nd}$ Ed., Chapman & Hall, London, 1994, pp. 1-551.

Hanessia, S. et al., "Design and Synthesis of Conformationally Constraines Amino Acids as Versatile Scaffolds and Peptide Manners", *Tetrahedron Lett.*, 53, 1997, pp. 12789-12854.

Herschman, "Recent progress in the cellular and molecular biology of prostaglandin synthesis", *Trends Cardiovasc. Med.*, 1998, pp. 145-150.

Hibbeln, "Fish consumption and major depression", *Lancet*, vol. 351, 1998, p. 1213.

Higuchi, R. et al., "Kinetic PCR analysis: real time monitoring of DNA amplification reactions", Biotechnology, vol. 11, 1993, pp. 1026-1030.

Hill et al., "Trout thrombocytes contain 12-but not 5-lipoxygenase activity", Biochem. Biophys. Acta 1999, pp. 63-70.

Hill, E.M. et al., "Identification and egg hatching activity of monohydroxy fatty acid eicosanoids in the barnacle Balanus balanoides", Proc. R. Soc. London, Ser. B, vol. 247, No. 1318, 1992, pp. 41-46, XP002200247.

Hill, E.M., *Proc R. Soc. London Ser. B.*, 247 (1318) 1992, pp. 41-46.

Hong, et al., "Novel Docosatrienes and 17S-Resolvins Generated from Docosahexaenoic Acid in Murine Brain, Human Blood, and Glial Cells", Autacoids in Anti-Inflammation, *J. Biol. Chem.* 278(17), 2003, pp. 14677-14687.

Hoyng, C.F. and A.D. Patel, "Aldehyde Components for use in Four-Component Condensation ("4CC") UGI Reaction Peptide Synthesis", *Tetrahedron Lett.*, (21) 1980, pp. 4795-4798.

Humphrey, J.M. and A.R. Chamberlin, "Chemical Synthesis of Natural Product Peptides Coupling Methods for the Incorporation of noncoded Amino Acids into Peptides", *Chem. Rev.*, 97, 1997, pp. 2243-2266.

Iacoviello et al., "Modulation of Fibrinolytic Response to Venous Occlusion in Humans by a Combination of Low-Dose Aspirin and n-3 PUFAs", Arteriosclerosis Thrombosis, vol. 10, 1992, pp. 1191-1197.

Ikeda et al., "Chiral Allenylboronic Esters as Practical Reagent for Enantioselective Carbon-Carbon Bond formation Facile Synthesis of (-) Ipsenol", *J. Am. Chem, Soc.*,108, 1986, pp. 483-4486.

Jenski, L.J., et al. "docosahexaenoic acid-induced alteration of Thy-1 and CD8 expression on murine splenocytes", *Biochim, Biophys. Acta.* 1236, pp. 39-50, 1995.

Karanian, J. et al., "Physiological functions of hydroxy-docosahexaenoic acid", 1992, XP002200246.

Karanian, J.W. et al., "Inhibitory Effects of n-6 and n-3 Hydroxy Fatty Acids on Thromboxane (U46619)-Induced Smooth Muscle Contraction", J. of Pharmacology and Experimental Therapeutics, vol. 270, No. 3, 1994, pp. 1105-1109.

Kato, T. et al., "Production of hydroxy unsaturated fatty acids using crude lipoxygenase obtained from infected rice plants", Bulletin of the Chemical Society of Japan, vol. 69, No. 6, 1996, pp. 1663-1666, XP002200251.

Khair-El-Din et al., "Transcription of the murine INOS gene is inhibited by docosahexanaenoic acid, a major constituent of fetal serum and fish oils diets inhibits IFN alpha-induced la-expression by murine macrophases in vitro", J. Immuno., vol. 154, 1995, pp. 1296-1306.

Khair-El-Din, et al. "Transcription of the Murine iNOS Gene is Inhibited by Docosahexaenoic Acid, a Major Constituent of Fetal and Neonatal Sera as Well as Fish Oils", J. Exp. Med., vol. 183, pp. 1241-1246, 1996.

Khalfoun, B. et al., "Docosahexaenoic and Eicosapentaenoic Acids Inhibit Human Lymphoproliferative Responses In Vitro but not the Expression of T cells Surface Activation Markers", Scandinavian J. Immunology, vol. 43, 1996, pp. 248-256, XP0000878923, ISSN: 0300-9475.

Kitajka et al., "The role of n-3 polyunsaturated fatty acids in brain: Modulation of rat brain gene expression by dietary n-3 fatty acids", Proc. Natl. Acad. Sci., USA9, 2002, pp. 2619-2624.

Knapp, Howard R., et al., "Bactericidal Effects of Polyunsaturated Fatty Acids", The Journal of Infectious Diseases, vol. 154, No. 1, 1986, pp. 84-94.

Konig et al., "Synthesis of N-Tert-Alkylglyxolic Acid Amides", Syntheses, pp. 1233-1234, (1993), [ In German, English language abstract on 1 st page of article ].

Lau et al., "Effects of Fish Oil Supplementation on Non-Steroidal Anti-Inflammatory Drug (NSAID) Requirement in Patients with Mild Rheumatoid Arthritis—A Double-Blind Placebo Controlled Study", British Journal of Rheumatology, vol. 32 (11), 1993, pp. 982-989.

Lee et al., "Characterization and biologic properties of 5,12-dihydroxy derivatives of eicosapentaenoic acid, including leukotriene B5 and the double lipoxygenase product", J. Biol. Chem., 1984, pp. 2383-2389.

Lee et al., "Effects of exogenous arachidonic, eicosapentaenoic, and docosahexaenoic acids on the generation of 5-lipoxygenase pathway products by ionophore-activated human neutrophils", J. Clin. Invest., vol. 74, 1984, pp. 1922-1933.

Levy et al., "Lipid mediator class switching during acute inflammation: signals in resolution", Nature Immunol., vol. 2, 2001, pp. 612-619.

Levy, "Prostaglandin H synthases, nonsteriodal anti-inflammatory drugs, and colon cancer", FASEB J., 1997, pp. 234-247.

Levy, O. "A neutrophil-derived anti-infective molecule: bactericidal/permeability-increasing protein", Antimicrobial Agents and Chemotherapy, vol. 44, No. 11, 2000, pp. 2925-2931.

Levy, O., "Antimicrobial proteins and peptides of blood: templates for novel antimicrobial agents", Blood, vol. 96, No. 8, 2000, pp. 2664-2672.

Levy, Bruce D. et al. "Protectin D1 Is Generated in Asthma and Dampens Airway Inflammation and Hyperresponsiveness," The Journal of Immunology, 2007, 178: 496-502.

Libby, "Atherosclerosis, The New View", Sci. Am., vol. 286, 2002, pp. 46-55.

Ligo, et al., "Inhibitory Effects of Docosahexaenoic Acid on Colon Carcinoma to the Lung", Br. J. Cancer, 1997, pp. 650-655.

Lockhart, D.J. et al., "Expression monitoring by hybridization to high-density oligonucleotide arrays", Nature Biotechnology, vol. 14, No. 13, 1996, pp. 1675-1680.

Loeschke D. et al., Dig. Dis. Sci., vol. 41, 1996, pp. 2087-2094.

Maddox et al., "Lipoxin $A_4$ and $B_4$ are potent stimuli for human monocyte migration and adhesion" selective inactivation by dehydrogenation and reduction, J. Exp. Med., vol. 183, 1996, pp. 137-146.

Marcheselli, et al. "Novel Docosanoids Inhibit Brain Ischemia-Reperfusion-Mediated Leukocyte Infiltration and Pro-Inflammatory Gene Expression", J. Biol. Chem. 278(44), 2003, pp. 43807-43817.

Marchioli, R. et al., "Early protection against sudden death by n-3 polyunsaturated fatty acids after myocardial infarction: time-course analysis of the results of the Gruppo-Italiano per lo Studion della Sopravivenze nell'Infarto Miocardico", Circulation, vol. 105, 2002, pp. 1897-1903.

Marchioloi, "Dietary supplementation with n-3 polyunsaturated fatty acids and vitamin E after myocardial infarction: results of the GISSI-Prevenzione trial", Lancet 1999, pp. 447-455.

Marcus, "Platelets: their role in hemostasis, thrombosis, and inflammation", Inflammation: Basic Principles and Clinical Correlates, 1999, pp. 77-95.

Martinez et al., "Docohexaenoic acid—a new therapeutic approach to peroxisomal disorder patients: Experience with two cases", Neurology, vol. 43, 1993, pp. 1389-1397.

Marx et al., "Synthetic Design for Combinatorial Chemistry. Solution and Polymer-Supported Synthesis of Polycyclic Lactams by Intramoloecular Cyclization of Azomethane Ylides", J. Chem. Soc., 119, 1997, pp. 6153-6167.

Marzo et al., "Biosynthesis of docohexaenoic acid in human cells, evidence that two different—desaturase activities may exist", Biochem. Biophys. Acta 1301, 1996, pp. 263-272.

Mata de Urquiza et al., "Docosahexaenoic acids, a ligand for the retinoid X receptor in mouse brain", Science, vol. 290, 2000, pp. 2140-2144.

McCormick, B.A. et al., "Salmonella typhimurium attachment to human intestinal epithelial monolayers: transcellular signaling to subepithelial neurophils", J. Cell Biology, vol. 123, No. 4, 1993, pp. 895-907.

McLennan et al., "The cardiovascular protective role of the docosahexaenoic acid", Eur. J. Pharmacol. vol. 300, 1996, pp. 83-89.

McMahon et al., "Lipoxins: Revelations On Resolution", Trends in Pharmacological Sciences, vol. 22, 2001, pp. 391-395.

Mehta et al., "Structure—Activity Relationship of a New Class of Anti-Hepatitis B Virus Agents", Antimicrobial Agents and Chemotherapy, 46(12) 2002, pp. 4004-4008.

Miller et al., "Dietary supplementation with ethyl ester concentrates of fish oil (n-3) and borage oil (n-6) polyunsaturated fatty acids induces epidermal generation of local putative anti-inflammatory metabolites", J. Invest. Dermat., vol. 96, 1991, pp. 98-103.

Miller et al., "Oxidative metabolism of dihomogammalinolenic acid by guinea pig epidermis: Evidence of generation of anti-inflammatory products", Prostaglandins, vol. 35, 1988, pp. 917-938.

Miller et al., "Guinea Pig Epidermis Generates Putative Anti-Inflammatory Metabolites from Fish Oil Polyunsaturated Fatty Acids", Lipids, Chemical Abstract 24(12), 112: 117062, pp. 998-1003, 1989. Lipids, Chemical Abstract 112:117062, 1989, pp. 998-1003.

Needleman et al., "The discovery and function of COX-2", J. Rheumatol, 1997, pp. 6-8.

Nicolaou et al., "Lipoxins and Related Eicosanoids: Biosynthesis, Biological Properties and Chemical Synthesis," Angew. Chem. Ed. Engl. 30, 1991, pp. 1100-1116.

Nicolaou et al., "Novel IBX-Mediated Process for the Synthesis of Amino Sugars and Libraries Thereof", Angew. Chem. Int. Ed. Engl., 39, 2000, pp. 2525-2529.

Node et al., "Anti-Inflammatory properties of cytochrome P450 epoxygenase-derived eicosanoids", Science, 1999, pp. 1276-1279.

Noyori, R. (Ed), "Enantioselective Addition of Organometallic Reagents to Carbonyl Compounds: Chirality Transfer, Multiplication and Amplification," Chapter 5 in Asymmetriccal Catalysts in Organic Synthesis, New York; Wiley & Sons, Inc., 1994, pp. 225-297.

Nugent, William A., "Chiral Lewis Acid Catalysts. Enantioselective Additon of Azide to Meso Epoxides", J. Am. Chem. Soc., 114(7), 1992, pp. 2768-2769.

O'Banion et al., "Cdna Cloning and functional activity of a glucocorticoid-regulated inflammatory cyclooxygenase", Proc. Natl., Acad., Sci. USA, vol. 89, 1992, pp. 4888-4892.

O'Donnell, Martin J. and J. Falmagne, "The Synthesis of Amino Acids via Organoboranes", J. Chem. Soc. Chem. Commun., No. 17, Sep. 1, 1985, pp. 1168-1169.

Olfson et al., "National trends in the outpatient treatment of depression", JAMA, vol. 287, 2002, pp. 203-209.

Palmantieri, et al., "Transcellular metabolism of arachidonic acid in platelets and polymorphonuclear leukocytes activated by physiological agonists: enhancement of leukotriene B4 synthesis", *Cell-Cell Interactions in the Release of Inflammatory Mediators*, vol. 314, 1991, pp. 73-89.

Petasis, N. A. and I.A. Zavialov, "A New and Practical Syntrhesis of Alpha Amino Acids from Alkenyl Boronic Acids", *J. Am. Chem. Soc.*, 119(2), 1997, pp. 445-446.

Petasis, N. A. and I.A. Zavialov, "The Boronic Acid Mannich Reaction: A New Method for the Synthesis of Geometrically Pure Allylamines", *Tetrahedron Letters*, 34(4)1993, pp. 538-586.

Pfaffl, M.W., "A new mathematical model for relative quantification in real-time RT-PCR", Nucleic Acids Research, vol. 29, No. 9, 2001, pp. 2002-2007.

Poling, et al., "Docosahexaenoic acid block of neuronal voltage-gated K+ channels: subunit selective antagonism by zinc", *Neuropharmacology*, vol. 35, 1996, pp. 969-982.

Pullarkat et al., "Leukocyte docosahexaenoic acid in juvenile form of ceroidlipofuscinosis", *Neuropadiatrie*, vol. 9, 1987, pp. 127-130.

Qiu et al., "Aspirin-triggered lipoxin $A_4$ and lipoxin $A_4$ up-regulate transcriptional corepressor NAB1 in human neutrophils", *FASEB J.* 1096/ fj. 1001-0576fje, 2001, vol. 10.

Rao et al, "Comparative Pharmacology of Cyclooxygenase Inhibitors on Platelet Function", *Prostaglandins Leukot Med.*, vol. 18 (1), 1985, pp. 119-131.

Rapp et al., "Dietary eicosapentaenoic acid and docosahexaenoic acid form fish oil", *Arteriosclerosis and Thrombosis*, vol. 11, 1991, pp. 903-911.

Reddy et al., "Change in content, incorporation and lipoxygenation of docosahexaenoic acid in retina and retinal pigment epithelium in canine ceroid lipofuscinosis", *Neuroscience Lett.*, vol. 59, 1985, pp. 67-72.

Reich, E.E. et al., "Formation of novel D-ring and E-ring isoprostane-like compounds ($D_4/E_4$- neuroprostanes) in vivo from docosahexaenoic acid", *Biochemistry*, vol. 39, 2000, pp. 2376-2383.

Reynaud et al., *Analytical Biochemistry* (1993), 214(1), pp. 165-170 , CA 119: 265901.

Ridker et al., "Inflammation, aspirin, and the risk of cardiovascular disease in apparently healthy men", N. Engl. J. Med. 1997, pp. 973-979.

Rodriguez and Spur, "Total Synthesis of aspirin-triggered 15-epi-lipoxin A4", *Tetrahedron Letters*, 42, 2001, pp. 6057-6060.

Rolinson et al., "Spatial requirements for 15-(R)- hydroxyl-5Z,8Z,11Z,13E-eicosatetraenoic acid synthesis with the cyclooxygenase active site of murine COX-2", J. Biol. Chem., vol. 275, 2000, pp. 6586-6591.

Rosenberg et al., "Fish-food to calm the heart", *N. Engl. J. Med.*, vol. 346, 2002, pp. 1102-1103.

Rowley et al., "Homeostasis in fish—an evolutionary perspective", *Throm. Homeost.*, vol. 77, 1997, pp. 227-233.

Ruettinger et al., "Epoxidation of unsaturated fatty acids by a soluble cytochrome P-45-dependent system from bacillus megaterium", J. Biol. Chem., 1981, pp. 5728-5734.

Salem, N. et al., "Arachidonic and docosahexaenoic acids are biosynthesized from their 18-carbon precursors in human infants", *Proc. Natl. Acad. Sci. USA*, vol. 93, 1996, pp. 49-54.

Samuelson et al., "From studies of biochemical mechanisms to novel biological mediators: prostaglandin endoperoxides, thromboxanes and leukotrienes", *In Les Prix Nobel*, 1982, pp. 165-174.

Samuelson et al., "Leukotrienes and lipoxins: structure, biosynthesis, and biological effects", *Science*, vol. 237, 1987, pp. 1171-1176.

Sawazaki et al., "Lipoxygenation of docosaxaenoic acid by the rate pineal body", *J. Neurochem.*, vol. 62, 1994, pp. 2437-2447.

Schmedtje, Jr. et al., "Hypoxia Induces Cyclooxygenase-2 via the NF- Kb p65 Transcription Factor in Human Vascular Endothelial Cells", *J. Biol. Chem.*, vol. 272, No. 1, 1997, pp. 601-608.

Serhan et al, "Design of lipoxin A4 stable analogs that block transmigration and adhesion of human neutrophils", *Biochemistry*, 1995, pp. 14609-14615.

Serhan et al., "Nomenclature of lipoxins and related compounds derived from arachidonic acid and eicosapentaenoic acid", Prostaglandins ,1987, pp. 201-204.

Serhan et al., "Novel functional sets of lipid-derived mediators with Anti-inflammatory Actions generated from omega-3 fatty acids via cyclooxygenase 2-nonsteroidal anti-inflammatory drugs and transcellular processing", *J. Exp. Med.*, vol. 192, No. 8, 2000, pp. 1197-1204.

Serhan et al., "Resolvins, Docosatrienes, and Neuroprotectins, Novel Omega-3-Derived Mediators, and their Aspirin-Triggered Endogenous Epimers: An Overview of Their Protective Roles in Catabasis", *Prostaglandins Other Lipid Mediat.* 5543, 2004, pp. 1-18.

Serhan et al., "Unorthodox routes to prostanoid formation: new twists in cyclooxygenase-initiated pathways" *J. Clin. Invest.*, vol. 107, 2001, pp. 1481-1489.

Serhan, "A Search for Endogenous Mechanisms of Anti-Inflammation Uncovers Novel Chemical Mediators: Missing Links to Resolution", *Histochem Cell Biol.* 122(4), 2004, pp. 305-321.

Serhan, "Novel Encosanoid and Docosanoid Mediators: Resolvins, Docosatrienes, and Neuroprotectins", *Cuff Opin Clin Nutr Metab Care*, 8(2), 2005, pp. 1-7.

Serhan, "Novel Omega-3-Derived Local Mediators in Anti-Inflammation and Resolution", *Pharmacol. Ther.* 105(1), 2005, pp. 7-21.

Serhan, et al., "Novel Endogenous Small Molecules as the Checkpoint Controllers in Inflammation and Resolution: Entrée for Resoleomics" *Rheum Dis Clin North Am.* 30(1), 2004, pp. 69-95.

Serhan, et al., "Novel functional sets of Lipid-derived mediators with anti-inflammatory actions generated from omega-3 fatty acids via Cyclooxygenase 2-nonsteroidal Anti-inflammatory drugs and transcelllular processing", *J. Exp. Med. Col.* vol. 192, 2000, pp. 1197-1204.

Serhan, et al., "Novel Pathways and Endogenous Mediators in Anti-Inflammation and Resolution", *Chem Immunol Allergy*, 83, 2003, pp. 115-145.

Serhan, et al., "Resolvins, Docosatrienes and Nueroprotectins, Novel Omega-3 Derived Mediators and their Endogenous Aspirin-Triggered Epimers", Lipids, vol. 39, 2004, pp. 1125-1132.

Serhan, et al., "Resolvins: a family of bioactive products of omega-3 fatty acids transformation circuits initiated by aspirin treatment that counter proinflammation signals", *J. Exp. Med.*, vol. 196, No. 8, 2002, pp. 1025-1037.

Serhan, et al. "Resolvins, Docosatrienes, and Neuroprotectins, Novel Omega-3-Derived Mediators, and their Endogenous Aspirin-Triggered Epimers", *Lipids*, 73: 155-172, 2004.

Sethi et al., "Inhibition of phagocyte-endothelium interactions by oxidized fatty acids: A natural anti-flammatory mechanism?", J. Lab. Clin. Med., 1996, pp. 27-38.

Shimizu, T. et al., "Enzyme with dual lipooxygenase activities catalyzes luekotriene $A_4$ synthesis from arachidonic acid", *Proc. Natl. Acad Sci. USA*, vol. 81, 1994, pp. 689-693.

Shinmura et al., "Cyclooxygenase-2 medaites the cardioprotectie effects of the late phase of ischemic preconditioning in conscious rabbits", *Proc. Natl. Acad. Sci. USA*, vol. 97, 2000, pp. 10197-10202.

Simopoulos, "Workshop on the essentiality of an recommended dietary intakes for omega-6 and omega-3 fatty acids", *J. Am. Coll. Nutr.*, 1999, pp. 487-489.

Srivastava, "Docosahexaenoic acid (C22:6w3) and linoleic acid are anti-aggregatory, and alter arachodonic acid metabolism in human platelets", *Prostaglandins Leukot. Med.*

Takeshi Terano, Ensho, Chemical Abstract 107:22439, 1987, pp. 63-71.

Takeshi Terano et al., "Eicosapentaenoic acid and docosahexaenoic acid inhibit vascular smooth muscle cell proliferation by inhibiting phosphorylation of Cdk2-cyclinE complex", *Biochem. Biophys. Res. Comm.*, vol. 254, pp. 502-506.

Taylor, C.T. et al., "Critical role of cAMP response element binding protein expression in hypoxia-elicited induction of epithelial tumor necrosis factor-a", J. Biol. Chem., vol. 274, No. 27, 1999, pp. 19447-19454.

Thompson, L.A. and J.A. Ellman, "Synthesis and Applications of Small Molecule Libraries", *Chem. Rev.* , 96, 1996, pp. 555-6000.

Tou, "Acylation of docosahexaenoic acid into phospholipids by by intact human neutrophils", *Lipids*, vol. 21, 1986, pp. 324-327.

Van Dyke, et al., "Resolution of Inflammation: A New Paradigm for the Pathogenesis of Periodontal Diseases", *J. Dent. Res.*, 82(2) 2003, pp. 82-90.

Vane et al., "Therapeutic Roles of Selective COX-2 Inhibitors", *William Harvey Press*, London, 2001.

VanRollins et al., "Autooxidation of docosahexaenoic acid: Analysis of ten isomers of hydroxydocosahexaenoate", *J. Lipid Res.*, vol. 25, 1984, pp. 507-517.

VanRollins et al., "Oxidation of docosahexaenoic acid by rat liver microsomes", *J. Biol. Chem.*, vol. 259, 1984, pp. 5776-5783 (CA 101:19194).

Vu Bois et al., "Novel, Stereoselcetive Synthesis of 2 Amino Saccharides", *J. Am. Chem. Soc.* 119, 1997, pp. 3179-3180.

Waki, M. and J. Meienhofer, "Peptide Synthesis Using the Four-Component Condensation (Ugi Reaction)," *J. Am. Chem. Soc.*, 99., 1997, pp. 6075-6082.

W.E.M. Lands, "Proceedings of the AOCS Short Course on Polyunsaturated Fatty Acids and Eicosanoids", American Oil Chemists' Society, 1987.

Weersink, A., et al., "Human granulocytes express a 550-kDa lipopolysaccharide-binding protein on the cell surface that is identical to the bactericidal/permeability-increasing protein", *J. Immunology*, vol. 150, No. 1, 1993, pp. 253-263.

Weiss, J. et al., "Purification and characterization of a potent bactericidal and membrane active protein from the granules of human polymorphonuclear leukocytes", *J. Biol. Chem.*, vol. 253, No. 8, 1987, pp. 2664-2672.

Weissmann, "Aspirin", *Sci. Am.*, 1991, pp. 84-90.

Whelan et al., "The unique characteristics of the purified 5-lipoxygenase from potato tubers and the proposed mechanism of formation of leukotrienes and lipoxins", *Biological Oxidation Systems*, vol. 2, 1990, pp. 765-778.

Xiao et al., "Analysis of hydroperoxide-induced tyrosyl radicals and lipoxygenase activity in aspirin-treated human prostaglandin H synthase-2", Biochemistry, 1997, pp. 1836-1845.

Yamamoto, Y. and N. Asao, "Selective Reactions Using Allylic Metals", *Chem Rev.*, 93, 1993, pp. 2207-2293.

Yamane, M. et al., "Docosahexaenoic/arachiconic acid omega-hydroxylation system and differentiation in the human colonic adenocarcinoma cell line, Caco-2", Cancer Letters, vol. 122, 1998, pp. 51-59, XP002200245.

Yergey et al., "High-performance liquid chromatography/ thermospray mass spectrometry of eicosanoids and novel oxygenated metabolites of docosahexaenoic acid", *Anal. Chem.*, vol. 58, 1986, pp. 1344-1348.

Yokomizo et al., "A G-protein-coupled receptor for leukotriene B4 that mediates chemotaxis", Nature, 1997, pp. 620-624.

Zeldin, "Epoxygenase pathways of arachidonic acid metabolism", *J. Biol. Chem.*, vol. 276, 2001, pp. 36059-36062.

Ziboth et al., "Inhibition of sheep vesicular gland oxygenase by unsaturated fatty acids from skin of essential acid deficient rats", *Prostaglandins*, 1974, vol. 5, pp. 233-240.

Ziboth et al., "Metabolism of polyunsaturated fatty acids by skin epidermal enzymes: generation of anti-inflammatory and antiproliferative metabolites", Am. J. Clin. Nutr., vol. 71 (Suppl.), 2000, pp. 361S-366S.

Chemical Abstracts online citation, AN:2004:143088, retrieved Aug. 15, 2007, from STN, Columbus, OH.

Hong, et al. "Rainbow trout (oncorhynchus mykiss) brain cells biosynthesize novel docasahexaenoic acid-derived resolvins and protectins—mediator lipidomic analysis", *Prostaglandins & Other Lipid Mediators*, Elsevier, vol. 78, No. 1-4, Jun. 13, 2005, pp. 107-116. XP005174168.

Serhan, Charles N. et al. "Anti-Inflammatory Actions of Neuroprotectin D1/Protectin D1 and it's Natural Stereoisomers: Assignments of Dihydroxy-Containing Docosatrienes", Journal of Immunology, 176(3), 1848-1959 Coden: J01MA3; ISSN 0022-1767, Feb. 1, 2006. XP002429095.

Chambers et al., Book of Abstracts, 215th ACS National Meeting, Dallas, Mar. 298-Apr. 2 (1998), MEDI-053 Publisher, American Chemical Society, Washington, D.C., Coden: 65QTAA.

Testa "Prodrug research: Futile or Fertile?" Biochemical Pharmacology, 2004, vol. 68, pp. 2097-2106.

Slots, et al., "General Health Risk of Periodontal Disease", International Dental Journal, Dec. 2001, 51(6), pp. 417-422.

Green, Gary A., "Understanding NSAIDS: From Aspirin to COX-2", Clinical Cornerstrone, Sports Medicine 2001, 3(5), pp. 50-59.

Merck Index, "Gingivitis", Copyright © 1995-2007 Merck & Co., Inc., Whitehouse Station, NJ, USA, Last Full Version, Feb. 2003, 3 pgs.

Stella, Valentino J., Expert Opinion of Therapeutic Patents, Prodrugs as Therapeutics, 2004, 14(3), pp. 277-280.

Wolff et al., "Burger's Medicinal Chemistry and Drug Discovery." 5th Ed., vol. 1, pp. 975-977, 1994.

Dragoli et al., "Parallel Synthesis of Prostaglandin E$_1$ Analogues", J. Comb. Chem., 19699, pp. 534-539.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005 (in name of Trustees of Boston University).

PCT/US2006/011222 International Search Report dated Oct. 5, 2007.

PCT/US2005/009056 International Search Report dated Nov. 16, 2005.

Stahl, G.L. et al., Pharmacologic profile of lipoxins A5 and B5: new biologically active eicosanoids European Journal of Pharmacology, 1989, vol. 163, No. 1, 99. 55-60.

Lloyd-Evans, P. et al., Eicosanoid generation and effects on the aggregation of thrombocytes from the rainbow trout, Oncorhynchus mykiss, Biochimica et Biophysica Acta, Lipids and Lipid Metabolism, 1994, vol. 1215, No. 3. pp. 291-299.

Yamane, M. et al., High-performance liquid chromatography-thermospray mass spectrometry of epoxy polyunsaturated fatty acids and epoxyhydroxy polyunsaturated fatty acids from an incubation mixture of rat tissue homogenate, Journal of Chromatography, B: Biomedical Sciences and Applications, 1994, vol. 652, No. 2, pp. 123-136.

Inhibitory potencies of fish oil hydroxyl fatty acids on cellular lipoxygenases and platelet aggregation, Biochemical Pharmacology, 1991, vol. 42, No. 4, p. 959-962.

\* cited by examiner

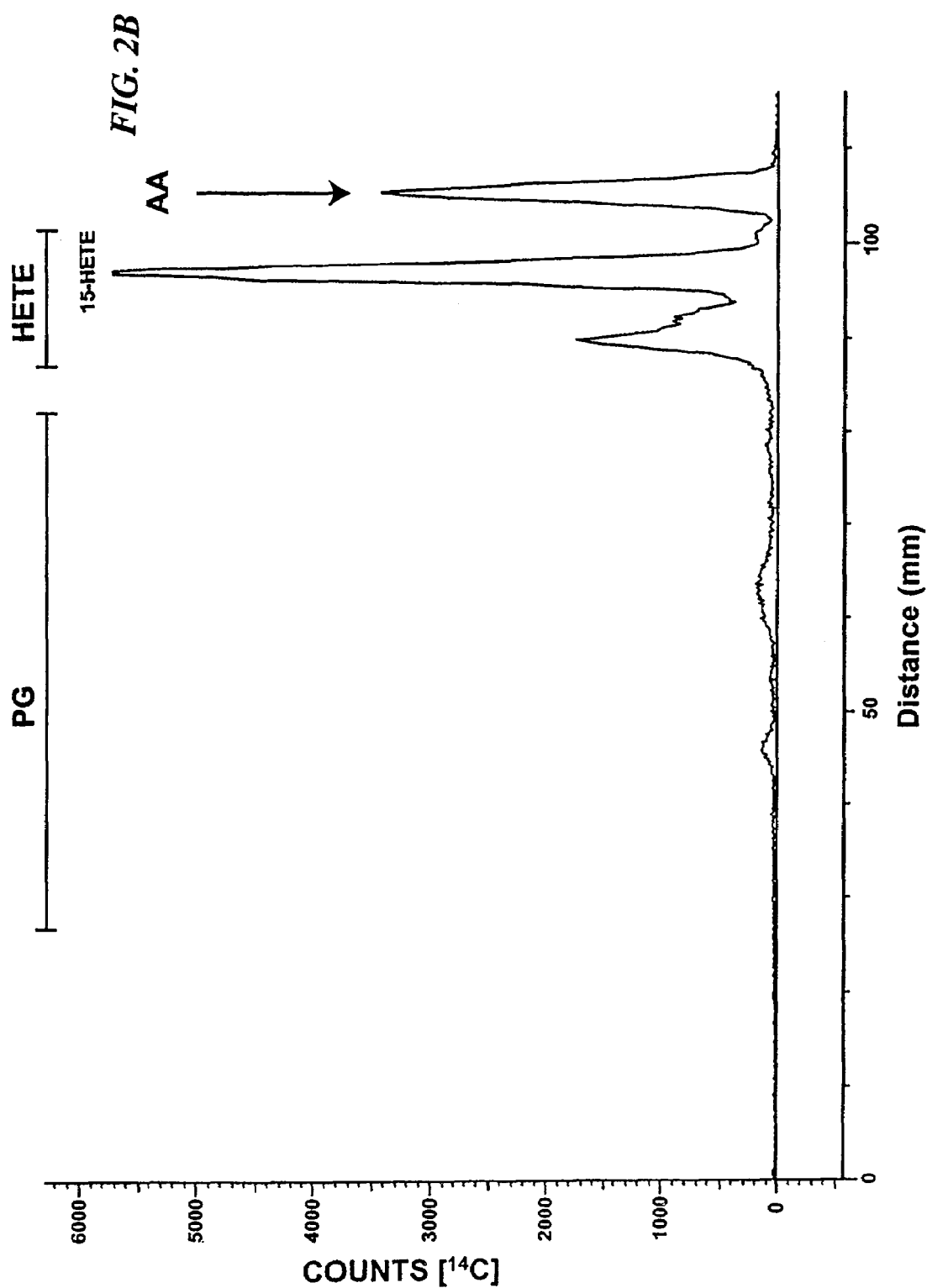

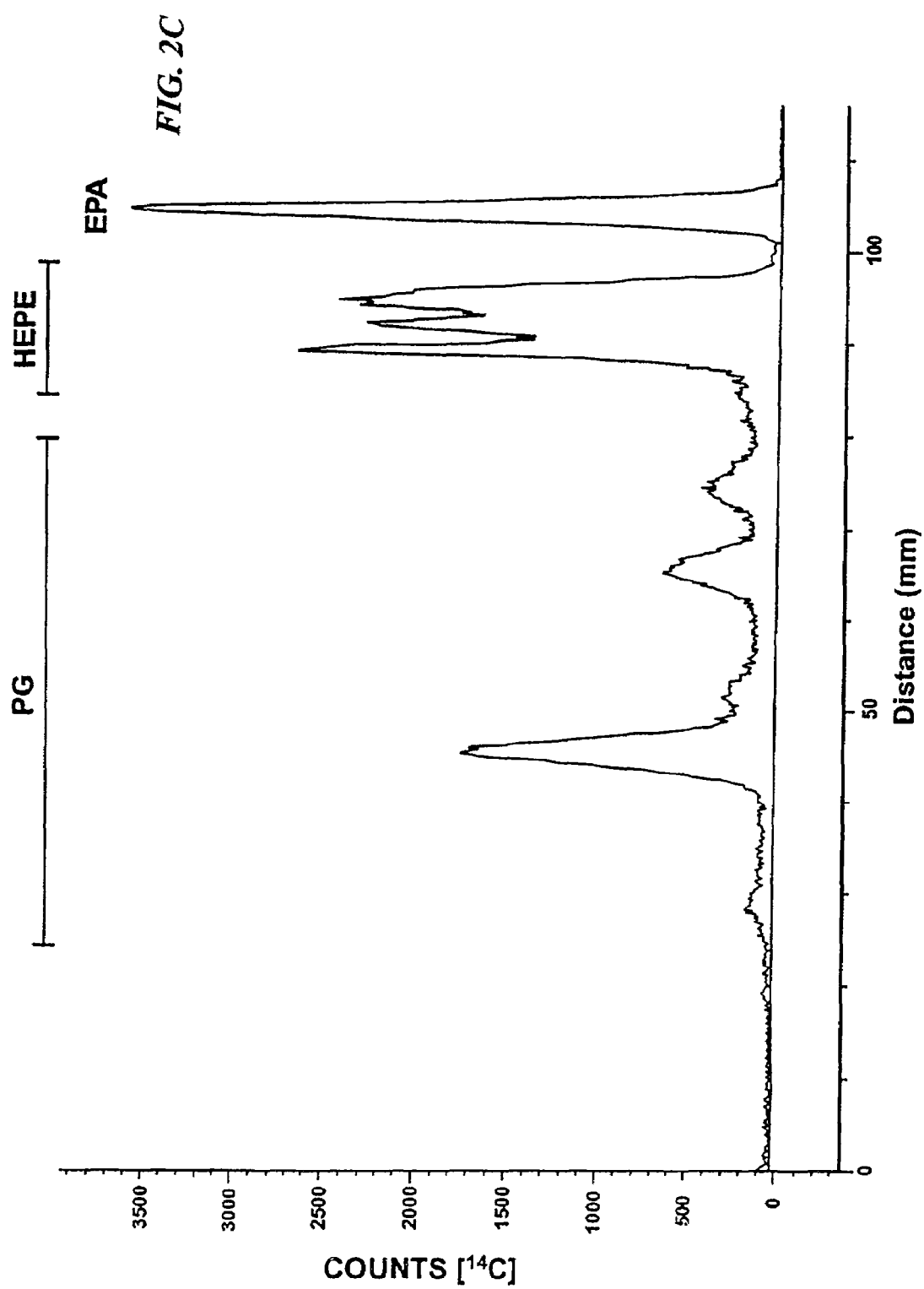

Conversion of EPA by *B. megaterium*

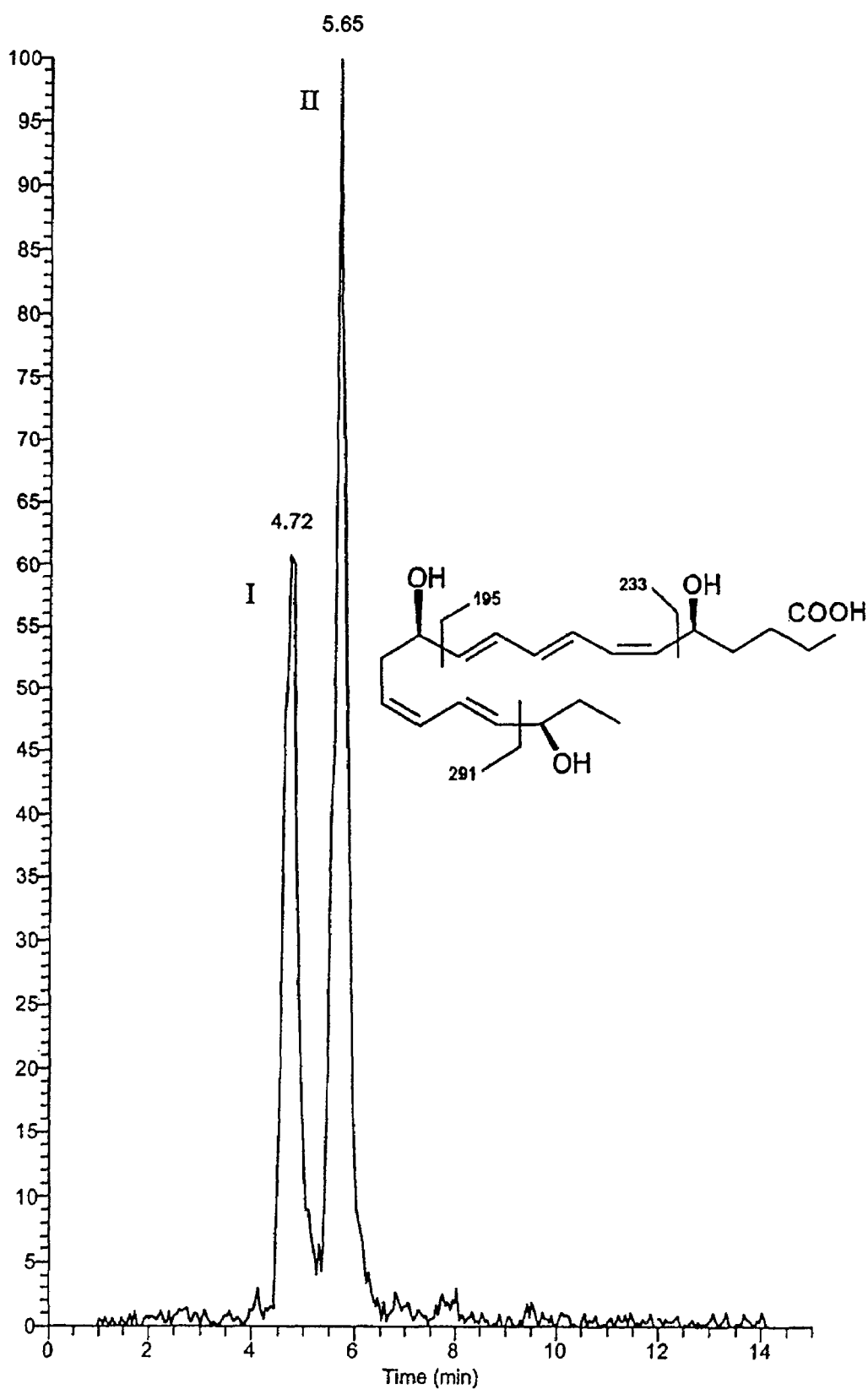
FIG. 5-1  MS 5,12,18-tri-HEPE from B. megaterium

I MS/MS m/z 349.4

II MS/MS m/z 349.4

Mono-HEPES: Enzymatic Products from Acetylated COX 2 and EPA

A

B

Major Products | Minor Products

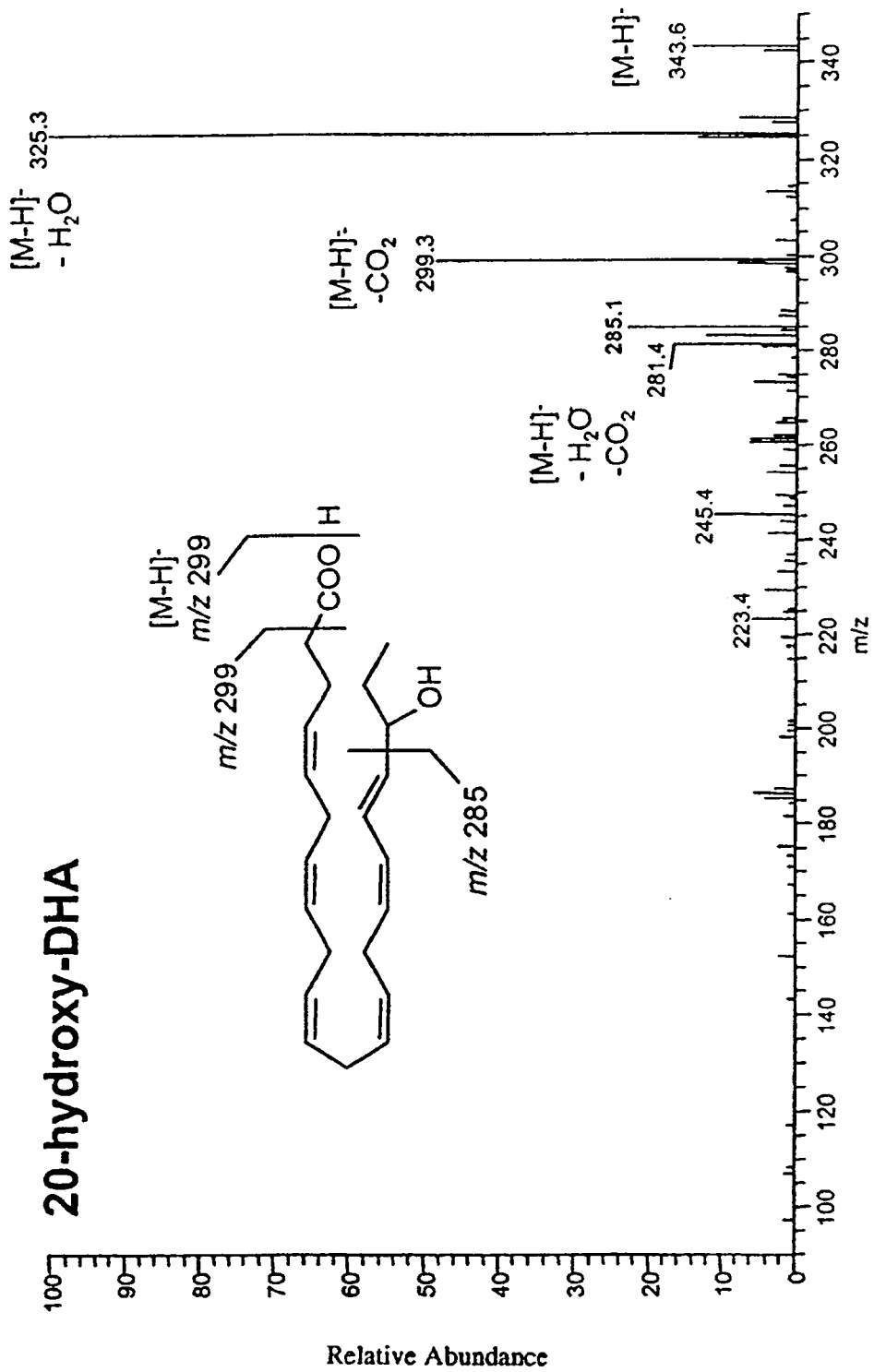
FIG. 14G-2 20-hydroxy-DHA

ASPIRIN-TRIGGERED LIPID MEDIATORS

CROSS-REFERENCE TO RELATED APPLICATIONS

This application is a continuation of U.S. application Ser. No. 11/334,330, filed Jan. 18, 2006, which is a divisional application of U.S. application Ser. No. 10/663,061, filed Sep. 12, 2003, now U.S. Pat. No. 7,053,230 which claims priority to U.S. Divisional patent application Ser. No. 09/785,866, filed Feb. 16, 2001, now U.S. Pat. No. 6,670,396 issued on Dec. 30, 2003, which claims priority to U.S. Provisional Application Ser. No. 60/183,078, filed Feb. 16, 2000, entitled "Aspirin-Triggered Lipid Mediators" by Charles N. Serhan and U.S. Provisional Application Ser. No. 60/238,814, filed Oct. 6, 2000, entitled "Aspirin-Triggered Lipid Mediators" by Charles N. Serhan, the contents of which are incorporated herein by reference in their entirety.

STATEMENT REGARDING FEDERALLY SPONSORED RESEARCH

The U.S. government may have rights in this invention pursuant to National Institute of Health grants GM38765, HL60569, and P01-DE13499.

BACKGROUND

Numerous reports of the past 25 years suggest that supplementation of dietary omega-3 polyunsaturated fatty acids (w-3 PUFA) with linseed, canola, or fish oils has beneficial effects in human diseases and laboratory animals (1. De Caterina, R., S. Endres, S. D. Kristensen, and E. B. Schmidt, editors. 1993. *n-3 Fatty Acids and Vascular Disease*. Springer-Verlag, London and 2. Lands, W. E. M., editor. 1987. *Proceedings of the AOCS Short Course on Polyunsaturated Fatty Acids and Eicosanoids*. American Oil Chemists' Society, Champaign, Ill.). These have included lively discussions of potential antithrombotic, immunoregulatory, and antiinflammatory responses relevant in arteriosclerosis, arthritis, and asthma as well as antitumor and antimetastratic effects (Ref. 1 and Iigo, M., T. Nakagawa, C. Ishikawa, Y. Iwahori, M. Asamoto, K. Yazawa, E. Araki, and H. Tsuda. 1997. Inhibitory effects of docosahexaenoic acid on colon carcinoma 26 metastasis to the lung. *Br. J. Cancer* 75:650-655). Their potential for preventative actions in cardiovascular diseases was recently bolstered with the finding that major dietary ω-3 PUFAs, eicosapentaenoic acid (C20:5 ω-3; EPA) and docosahexaenoic acid (C22:6 ω-3; DHA), have a dramatic effect on ischemia-induced ventricular fibrillation and can protect against sudden cardiac death in dogs (4. Billman, G. E. et al. 1999 Prevention of sudden cardiac death by dietary pure ω-3 polyunsaturated fatty acids in dogs. *Circulation*. 99:2452-2547). Emergence of such possible preventative and/or therapeutic actions of ω-3 PUFA supplementation in infant nutrition, cardiovascular diseases, and mental health has led to a call for recommended dietary intakes by an international workshop (5. Simopoulous, A. P. et al. 1999. Workshop on the Essentiality of and Recommended Dietary Intakes for Omega-6 and Omega-3 Fatty Acids. *J. Am. Coll. Nutr.* 18:487-489). Also, the Gruppo Italiano per lo Studio della Sopravvivense nell'Infarto Miocardio (GISSI) Prevenzione trial evaluated the effects of ω-3 PUFA supplementation with >11,300 patients surviving myocardial infarction taking ~1 g of ω-3 PUFA daily (n=2,836) along with recommended preventive treatments including aspirin, and reported a significant benefit with a decrease in cardiovascular death (6. Marchioloi, R. 1999. Dietary supplementation with n-3 polyunsaturated fatty acids and vitamin E after myocardial infarction: results of the GISSI-Prevenzione trial. Gruppo Italiano per lo Studio della Sopravvivenza nell'Ifarto miocardioco. *Lancet*. 354:447-455). However, the cellular and molecular mechanism(s) for dietary ω-3 protective actions in all of the studies including those with neural tissues (Parkinson's disease and Alzheimer's disease and other known to involve inflammation in the brain) to date remain largely unexplained.

It is believed that the actions of the major lipid of fish oil, C20:5, are based upon (a) preventing conversion of arachidonic acid (C20:4%-6; AA) to proinflammatory eicosanoids (i.e. prostaglandins [PGs] and leukotrienes [LTS]); (b) serving as an alternate substrate producing 5-series LTS that are less potent; and/or (c) conversion by cyclooxygenase (COX) to 3-series prostanoids (i.e., $PGI_3$) with potencies equivalent to their 4-series PG counterparts to maintain antithrombotic actions (References 1, 3 and 4). These and other explanations offered have not been generally accepted because of the lack of molecular evidence in vivo and high concentrations of ω-3 PUFA required to achieve putative "beneficial actions" in vitro (References 1-5).

Although the proinflammatory roles of LT and PG are appreciated, there is new evidence that other eicosanoids derived from arachidonate, namely lipoxins (LXs) and their endogenous analogues, the aspirin-triggered 15 epimer LXs (ATLs), are potent counterregulators of PMN-medicated injury and acute inflammation (7. Weissmann, G. 1991. Aspirin. *Sci. Am.* 264:84-90; 8. Marcus, A. J. 1999. Platelets: their role in hemostasis, thrombosis, and inflammation. In Inflammation: Basic Principles and Clinical Correlates. J. I. Gallin and R. Snyderman, editors. Lippincott Williams & Wilkins, Philadelphia. 77-9; 9. Claria, J., and C. N. Serhan. 1995. Aspirin triggers previously undescribed bioactive eicosanoids by human endothelial cell-leukocyte interactions. *Proc. Natl. Acad. Sci. USA* 92:9475-9479; 10. Serhan, C. N., J. F. Maddox, N. A. Petasis, I. Akritopoulou-Zanze, A. Papayianni, H. R. Brady, S. P. Colgan, and J. L. Madara. 1995. Design of lipoxin $A_4$ stable analogs that block transmigration and adhesion of human neutrophils. *Biochemistry* 34:14609-14615; and 11. Chiang, N., K. Gronert, C. B. Clish, J. A. O'Brien, M. W. Freeman, and C. N. Serhan. 1999. Leukotriene $B_4$ receptor transgenic mice reveal novel protective roles for lipoxins and aspirin-triggered lipoxins in reperfusion. *J. Clin. Invest.* 104:309-316). At least two isoforms for COX, the classic site of action for nonsteroidal antiinflammatory drugs (NSAIDs), have been uncovered (COX-1 and 2) that appear to serve separate physiologic and pathophysiologic roles in humans (12. Herschman, H. R. 1998. Recent progress in the cellular and molecular biology of prostaglandin synthesis. *Trends Cardiovasc. Med.* 8:145-150). Each COX isoform carries dual enzymatic activities, a bisoxygenase and a peroxidase. Inhibition of COX-2 is the current focus of several pharmaceutical companies, as selective inhibition of COX-2 without blocking COX-1 could reduce unwanted side effects associated with traditional NSAIDs (13. Needleman, P., and P. C. Isakson. 1997. The discovery and function of COX-2. *J. Rheumatol.* 24 (Suppl. 49):6-8). In this regard, acetylation of COX-2 by the classic NSAID, aspirin (ASA), prevents the formation of prostanoids, but the acetylated enzyme remains active in situs to generate 15R-hydroxyeicosatetraenoic acid (15R-HETE) from C20:4 that is released and converted by activated inflammatory cells to the 15-epimeric LXs (14. Chiang, N., T. Takano, C. B. Clish, N. A. Petasis, H.-H. Tai, and C. N. Serhan. 1998. Aspirin-triggered 15-epi-lipoxin $A_4$ (ATL) generation by human leukocytes and murine peritonitis exudates: Development of a specific 15-epi-LXA$_4$ ELISA. *J. Pharmacol. Exp. Ther.* 287: 779-790 and 15. Xiao, G., A.-L. Tsai, G. Palmer, W. C. Boyar, P. J. Marshall, and R. J. Kulmacz. 1997. Analysis of hydroperoxide-induced tyrosyl radicals and lipoxygenase activity in aspirin-treated human prostaglandin H synthase-2. *Biochemistry* 36:1836-1845). Synthetic analogues of these natural local mediators with prolonged biological half-life display potent antiinflammatory properties providing evidence that cell-cell interactions can be responsible for conversion of AA (and/or other lipids and PUFA see FIG. 1) to mediators that possess antiinflammatory properties by regulating signaling events important to host defense (Reference 11 and 16. Clish, C. B., J. A. O'Brien, K. Gronert, G. L. Stahl, N. A. Petasis, and C. N. Serhan. 1999. Local and systemic delivery of a stable aspirin-triggered lipoxin prevents neutrophil recruitment in vivo. *Proc. Nad. Acad. Sci. USA* 96:8247-8252).

SUMMARY OF THE INVENTION

Aspirin therapy inhibits prostaglandin biosynthesis without directly acting on lipoxygenases, yet via acetylation of cyclooxygenase 2 (COX-2) it leads to bioactive lipoxins (LXs) epimeric at carbon 15 (15-epi-LX, also termed aspirin-triggered LX [ATL]). The present invention provides that inflammatory exudates from mice treated with ω-3 polyunsaturated fatty acid and aspirin (ASA) generate a novel array of bioactive lipid signals. Human endothelial cells with upregulated COX-2 treated with ASA converted C20:5 w-3 to 18R-hydroxyeicosapentaenoic acid (HEPE) AND 15R-HEPE. Each was used by polymorphonuclear leukocytes to generate separate classes of novel trihydroxy-containing mediators, including 5-series 15R-LX and 5,12,18R-triHEPE. These new compounds proved to be potent inhibitors of human polymorphonuclear leukocyte transendothelial migration and infiltration in vivo (ATL analogue >5,12,18R-triHEPE >18R-HEPE). Acetaminophen and indomethacin also permitted 18R-HEPE and 15R-HEPE generation with recombinant COX-2 as well as ω-5 and ω-9 and other novel oxygenations of polyunsaturated fatty acids (e.g., C18:3, C22:6) that act on vascular, brain, inflammatory and hematologic cells. These findings establish new transcellular routes for producing arrays of bioactive lipid mediators via COX-2-nonsteroidal antiinflammatory drug-dependent oxygenations and cell-cell interactions that impact microinflammation. The generation of these and related compounds, provides a novel mechanism(s) for the therapeutic benefits of ω-3 dietary supplementation, which are important in inflammation, neoplasis, and vascular diseases.

Oxidation of C20:4 via P450 in endothelial cells (ECs) also leads to 11,12-epoxyeicosatetraenoic acid that appears to block EC activation, while nonenzymatic oxidation of EPA can down regulate EC adhesion molecules (17. Node, K., Y. Huo, X. Ruan, B. Yang, M. Spiecker, K. Ley, D. C. Zeldin, and J. K. Liao. 1999. Anti-inflammatory properties of cytochrome P450 epoxygenase-derived eicosanoids. *Science* 285:1276-1279 and 18. Sethi, S., A. Y. Eastman, and J. W. Eaton. 1996. Inhibition of phagocyte-endothelium interactions by oxidized fatty acids: A natural anti-inflammatory mechanism? *J. Lab. Clin. Med.* 128:27-38). As PMN-vessel interactions are pivotal to recruitment and PMN-dependent tissue injury, the local signals involved in their "cross talk dialogue" are of interest. The present invention provides that aspirin-acetylated COX-2 remains active in vivo to generate specific ATLs that can be effector of well established antiinflammatory reactions offers a mechanism for beneficial effects of ASA that cannot be attributed to inhibition of prostanoids alone (References 8, 12, 14). New therapeutic application for ASA and related NSAIDs continue to emerge. However, they usually require molecular definition to provide a rationale. This includes the reported prophylactic benefit of ASA in colorectal cancer and the lower risk of a second myocardial infarction (Reviewed in 19. Levy, G. N. 1997. Prostaglandin H synthases, nonsteroidal anti-inflammatory drugs, and colon cancer. *FASEB J* 11:234-247). In view of the qualitatively overlapping beneficial profiles assigned to dietary (ω)-3 PUFA in human disease (References 1-6), the present invention is directed toward novel pathways for lipid-derived signals that provide a molecular basis and also serve as markers for these beneficial actions.

The present invention is drawn to methods for treating or preventing inflammation in a mammal by administration of a combination of a polyunsaturated fatty acid(s) (PUFA(s)) and aspirin, i.e., polyunsaturated fatty acids including C18:3, C20:4 and C22:6. In one embodiment, the omega fatty acid, e.g., C18:3 or C22:6, and aspirin are administered at two different times. The present invention is also drawn to methods for treating arterial inflammation, arthritis, psoriasis, urticara, vasculitis, asthma, ocular inflammation, pulmonary inflammation, pulmonary fibrosis, seborrheic dermatitis, pustular dermatosis, or cardiovascular diseases in a mammal by administration of a combination of an omega fatty acid and aspirin to the mammal.

In another embodiment, the present invention is drawn to methods for treating or preventing inflammation in a mammal by administration of an anti-inflammatory of the natural class of ASA-triggered lipid (ω-3) mediators having one of the following formulae:

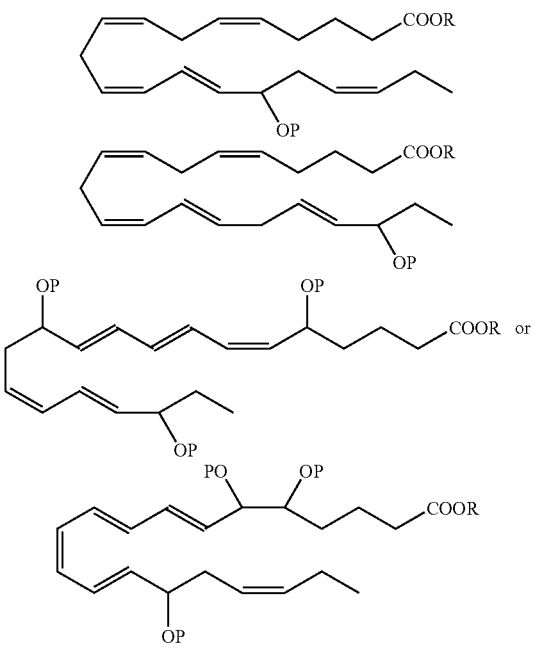

and their steroisomers, e.g., enantiomers, diastereomers, racemates, wherein R is a hydrogen atom or a pharmaceutically acceptable salt, ester, amide or prodrug, e.g., pharmaceutically acceptable analogues thereof. Preferred analogues include methyl, ethyl and glycerol esters. P is H (hydroxyl) or a suitable protecting group or groups where there are multiple hydroxyl groups, such as those known in the art. These hydroxyl protecting group(s) include esters (acetate, ethylacetate), ethers (methyl, ethyl), ethoxylated derivatives (ethylene glycol, propylene glycol) and silylated groups (TMS or TIPPS).

In another embodiment, the present invention is drawn to compositions and methods for treating or preventing inflammation in a mammal by administration of an anti-inflammatory of the natural class of ASA-triggered lipid ω-2, ω-3 or ω-4) mediators that are monohydroxylated docosahexaenoic acids (DHA) (C22:6), i.e., 13-hydroxy-DHA, 14-hydroxy-DHA, 16-hydroxy-DHA, 17-hydroxy-DHA, 19-hydroxy-DHA or 20-hydroxy-DHA, wherein the carboxylic acid can be functionalized as a hydrogen atom or a pharmaceutically acceptable salt, ester, amide or prodrug, e.g., pharmaceutically acceptable analogues thereof. Preferred analogues include methyl, ethyl and glycerol esters. The hydroxyl groups of the mono-hydroxylated DHA compounds can also be protected as described herein. Suitable protecting group or groups, such as those known in the art. These include esters (acetate, ethylacetate), ethers (methyl, ethyl), ethoxylated derivatives (ethylene glycol, propylene glycol) and silyl ether groups (TMS or TIPPS).

In one aspect of the invention, the compound(s) of the invention are substantially purified and isolated by techniques known in the art. The purity of the purified compounds is generally at least about 90%, preferably at least about 95%, and most preferably at least about 99% by weight.

In still another embodiment, the invention is drawn to methods for treating arterial inflammation, arthritis, or cardiovascular diseases in a mammal, comprising administering to the mammal one or more of the above-described compounds.

Surprisingly, it has been unexpectedly discovered that the interaction between aspirin, COX-II and omega-3 and omega-6 fatty acids have an anti-inflammatory effect upon tissue(s). Moreover, this combination produces unique compounds having the above-identified formulae. These compounds have anti-inflammatory properties and can be used as anti-inflammatory agents for treatment of disease states or conditions which have inflammation associated with these diseases or conditions.

Advantageously, the compounds and methods of the invention have minimal side effects. Targeting of neutrophils by the compounds of the invention, prevents typical side effects associated with NSAIDs. NSAIDs have a broad range of biological/physiological actions whereas the compounds of the invention are more selective for neutrophils. As these compounds are neutrophil directed therapeutics to alleviate inflammation, side effects are decreased dramatically in comparison to typical NSAIDs. The compounds of the invention have minimal unwanted side effects, if any, in terms of constipation, renal toxicity and gastro-intestinal ulcerations or bleeding. These advantages provide useful alternatives for patients seeking relief from inflammatory conditions that would otherwise needlessly suffer from one or more of the typical side effects associated with NSAIDs.

BRIEF DESCRIPTION OF THE DRAWINGS

The invention will be more fully understood from the following detailed description taken in conjunction with the accompanying drawings, in which:

FIG. 10A-10L depict LC/MS/MS ion chromatograms and mass spectral analyses of monohydroxy products generated from dihomo-γ-linoleic acid (C20:3, ω-3) and aspirin acetylated-COX-2.

FIG. 14G-14H depict an LC/MS/MS ion chromatogram and mass spectral analysis of 16-hydroxy-DHA generated from DHA by aspirin acetylated-COX-2.

FIG. 14I-14J depict an LC/MS/MS ion chromatogram and mass spectral analysis of
17-hydroxy-DHA generated from DHA by aspirin acetylated-COX-2.

FIG. 14K-14L depict an LC/MS/MS ion chromatogram and mass spectral analysis of 19-hydroxy-DHA generated from DHA by aspirin acetylated-COX-2.

FIG. 14M-14N depict an LC/MS/MS ion chromatogram and mass spectral analysis of 20-hydroxy-DHA generated from DHA by aspirin acetylated-COX-2.

DETAILED DESCRIPTION OF THE INVENTION

Figure 1:
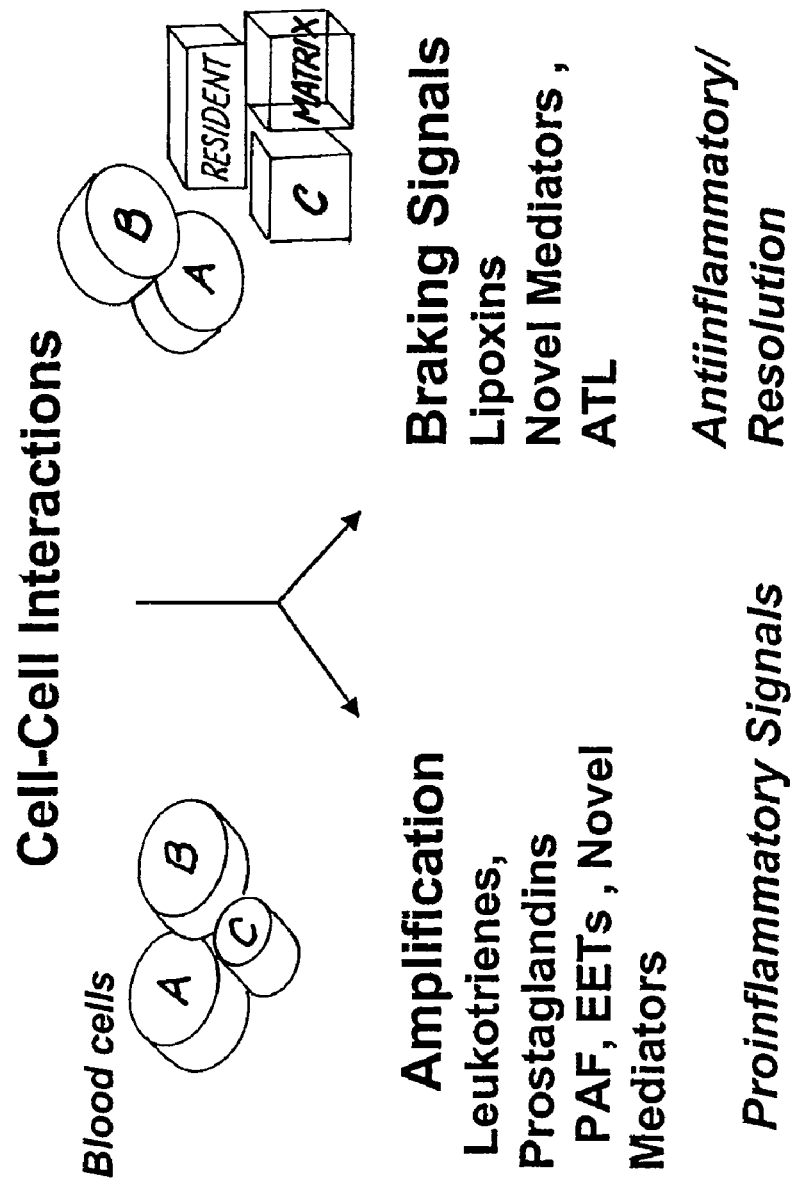
FIG. 1 depicts transcellular lipid mediator (LM) biosynthesis.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Abbreviations used throughout the present application include the following and are included here for convenience. NSAID, nonsteroidal anti-inflammatory drug; PUFA, polyunsaturated fatty acid(s); ALXR, LXA₄ receptor; ASA, aspirin; ATL, aspirin-triggered 15-epi-LX, 15R-LX; ATLM, aspirin-triggered lipid mediators; COX, cyclooxygenase I, II (isoforms); EC, endothelial cells; HUVEC, human umbilical vascular endothelial cells; LC/MS/MS, liquid chromatography tandem mass spectrometry; LM, lipid-derived mediators; LO, lipoxygenase; LT, leukotriene; LX, lipoxin; PG, prostaglandins; PMN, polymorphonuclear leukocyte; EPA eicosapentaenoic acid; HEPE, hydroxyeicosapentaenoic acid; HETE, hydroxyeicosatetraenoic acid; LXA₄, 5S,6R,15S-trihydroxy-7,9,13-trans-11-cis-eicosatetraenoic acid; 15-epi-LXA₄, 5S,6R,15R-trihydroxy-7,9,13-trans-11-cis-eicosatetraenoic acid; C20:5 (eicosapentaenoic acid, EPA, an ω-3 fatty acid); C20:4 (arachidonic acid, AA, an ω-6 fatty acid); and C22:6 (docosahexaenoic acid, DHA, an ω-3 fatty acid).

The present invention is drawn to methods for treating or preventing inflammation in a mammal by administration of a combination of an omega-3 (ω-3) fatty acid and aspirin. In one embodiment, the omega fatty acid, e.g., EPA, or DHA and aspirin are administered at two different times. The present invention is also drawn to methods for treating arterial inflammation, arthritis, or cardiovascular diseases in a mammal by administration of a combination of an omega fatty acid, such as EPA or DHA, and aspirin to the mammal.

In another embodiment, the present invention is drawn to compositions and methods for treating or preventing inflammation in a mammal by administration of an anti-inflammatory having one of the following formulae. Compound 1 has the formula:

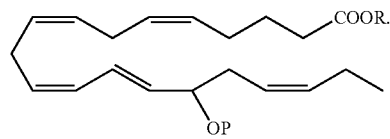

In a preferred embodiment, the hydroxyl at the carbon 15 position has an R configuration. In another embodiment, the hydroxyl at the carbon 15 position has an S configuration. Alternatively, the hydroxyl at the carbon 15 position is an R/S racemic mixture.

Compound 2 has the formula:

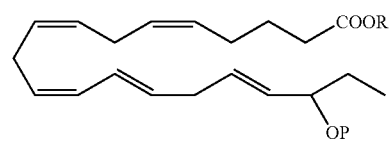

In a preferred embodiment, the hydroxyl at the carbon 18 position has an R configuration. In another embodiment, the hydroxyl at the carbon 18 position has an S configuration. Alternatively, the hydroxyl at the carbon 18 position is an R/S racemic mixture.

Compound 3 has the formula:

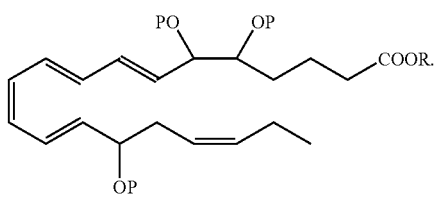

In one embodiment, the hydroxyl at the carbon 5 position has an S configuration, the hydroxyl at the carbon 6 position has an R configuration and the hydroxyl at the carbon 15 position has an R configuration. In another embodiment, the hydroxyl at the carbon 5 position has an R/S configuration, the hydroxyl at the carbon 6 position has an R/S configuration and the hydroxyl at the carbon 15 position has an R/S configuration.

Compound 4 has the formula:

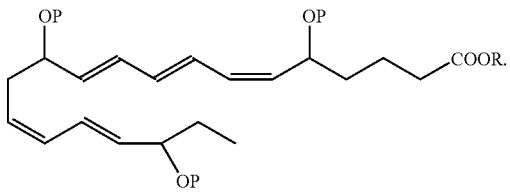

In one embodiment, the 5-hydroxyl has an S configuration, the 12-hydroxyl has an R configuration and the 18-hydroxyl has an R configuration. In another embodiment, the 5-hydroxyl has an R/S configuration, the 12-hydroxyl has an R/S configuration and the 18-hydroxyl has an R/S configuration.

Compound 5 has the formula

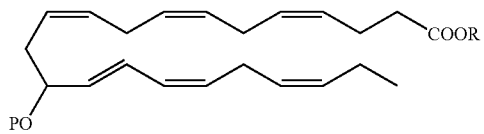

designated as 13-hydroxy-DHA, where P=H (hydroxyl). In one embodiment, the 13-hydroxyl has an S configuration. In another embodiment, the 13-hydroxyl has an R configuration. In still another embodiment, the 13-hydroxyl is a racemic mixture, e.g., an R/S configuration.

Compound 6 has the formula

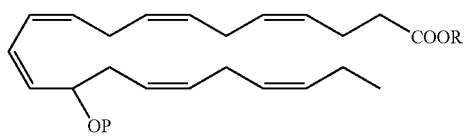

designated as 14-hydroxy-DHA, where P=H (hydroxyl). In one embodiment, the 14-hydroxyl has an S configuration. In another embodiment, the 14-hydroxyl has an R configuration. In still another embodiment, the 14-hydroxyl is a racemic mixture, e.g., an R/S configuration.

Compound 7 has the formula

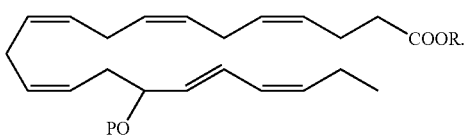

designated as 16-hydroxy-DHA, where P=H. In one embodiment, the 16-hydroxyl has an S configuration. In another embodiment, the 16-hydroxyl has an R configuration. In still another embodiment, the 16-hydroxyl is a racemic mixture, e.g., an R/S configuration.

Compound 8 has the formula

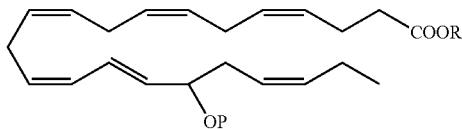

designated as 17-hydroxy-DHA, where P=H. In one embodiment, the 17-hydroxyl has an S configuration. In another embodiment, the 17-hydroxyl has an R configuration. In still another embodiment, the 17-hydroxyl is a racemic mixture, e.g., an R/S configuration.

Compound 9 has the formula

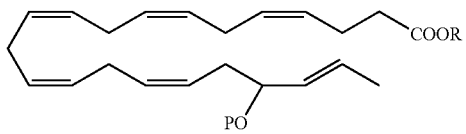

designated as 19-hydroxy-DHA, where P=H. In one embodiment, the 19-hydroxyl has an S configuration. In another embodiment, the 19-hydroxyl has an R configuration. In still another embodiment, the 19-hydroxyl is a racemic mixture, e.g., an R/S configuration.

Compound 10 has the formula

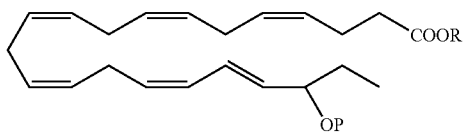

designated as 20-hydroxy-DHA, where P=H. In one embodiment, the 20-hydroxyl has an S configuration. In another embodiment, the 20-hydroxyl has an R configuration. In still another embodiment, the 20-hydroxyl is a racemic mixture, e.g., an R/S configuration.

In compounds 1 through 10, R is a hydrogen atom or is a pharmaceutically acceptable salt, ester, e.g., methyl ester, amide or prodrug. Preferred analogues include methyl, ethyl and glycerol esters.

In compounds 1 through 10, it should be understood that reference to "hydroxyl" stereochemistry is exemplary, and that the term is meant to include protected hydroxyl groups as well as the free hydroxyl group.

The hydroxyl(s) in compounds 1 through 10 can be protected by various protecting groups, such as those known in the art. An artisan skilled in the art can readily determine which protecting group(s) may be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, Chapters 5 and 7, 1991, the teachings of which are incorporated herein by reference. Preferred protecting groups include methyl and ethyl ethers, TMS or TIPPS groups, acetate or proprionate groups and glycol ethers, such as ethylene glycol and propylene glycol derivatives.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that for compounds 3 and 4, not all hydroxyl groups need be protected. One, two or all three hydroxyl groups can be protected. This can be accomplished by the stoichiometric choice of reagents used to protect the hydroxyl groups. Methods known in the art can be used to separate the mono, di- or tri-protected hydroxy compounds, e.g., HPLC, LC, flash chromatography, gel permeation chromatography, crystallization, distillation, etc.

It should be understood that there are one or more chiral centers in each of the above-identified compounds. It should understood that the present invention encompasses all stereochemical forms, e.g., enantiomers, diastereomers and racemates of each compound.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, once a pharmaceutically active compound is identified, those of skill in the pharmaceutical art generally can design prodrugs of the compound [see, e.g., Nogrady (1985) Medicinal Chemistry A Biochemical Approach, Oxford University Press, New York, pages 388-392]. Conventional procedures for the selection and preparation of suitable prodrug derivatives are described, for example, in "Design of Prodrugs," ed. H. Bundgaard, Elsevier, 1985. Suitable examples of prodrugs include methyl, ethyl and glycerol esters of the corresponding acid. Additionally, the protecting groups of the hydroxyl(s) functionality are considered as desirable as they can be metabolized to the parent compound, i.e., to the native hydroxyl functionality.

The compounds of the invention can be formulated into pharmaceutical compositions as described, infra. In a preferred embodiment, the compound can be administered over an extended period of time in a sustained release composition. Sustained release compositions are known in the art and one skilled in the art can formulate an acceptable composition based on generally recognized parameters in the art. In a most preferred embodiment, the glycerol ester can be used in the treatment of inflammatory conditions, described herein, in sustained release compositions, i.e., a transdermal patch, as known in the art. Suitable methods to prepare a transdermal patch can be found in U.S. Pat. Nos. 5,814,599, 5,846,974 or 4,201,211, the contents of which are incorporated herein by reference. More particularly, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with the inflammatory condition.

In still another embodiment, the invention is drawn to methods for treating arterial inflammation, arthritis, or cardiovascular diseases in a mammal, comprising administering to the mammal one or more of the above-described compounds.

The term "subject" as used herein refers to any living organism in which an, immune response, e.g., an antiinflammatory response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "mammal" as used herein refers to a living organism capable of eliciting an immune response to an antigen. The term subject includes, but is not limited to, nonhuman primates such as chimpanzees and other apes and monkey species, sheep, pigs, goats, horses, dogs, cats, mice, rats and guinea pigs, and the like.

The pharmaceutical compositions of the invention may include a "therapeutically effective amount" or a "prophylactically effective amount" of an antiinflammatory of the invention. A "therapeutically effective amount" refers to an amount effective, at dosages and for periods of time necessary, to achieve the desired therapeutic result, e.g., a diminishment or prevention of inflammation associated with various disease states or conditions. A therapeutically effective amount of the antiinflammatory may vary according to factors such as the disease state, age, sex, and weight of the individual, and the ability of the antiinflammatory to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antiinflammatory of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The antiinflammatory compounds of the invention, e.g., compounds 1 through 10, can be incorporated into pharmaceutical compositions suitable for administration to a subject. Typically, the pharmaceutical composition comprises an antiinflammatory of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antiinflammatory.

The antiinflammatories of the invention can be incorporated into a pharmaceutical composition suitable for parenteral administration. Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans. The preferred mode of administration is parenteral (e.g., intravenous, subcutaneous, intraperitoneal, intramuscular). In a preferred embodiment, antiinflammatory is administered by intravenous infusion or injection. In another preferred embodiment, the antiinflammatory is administered by intramuscular or subcutaneous injection. In the most preferred embodiment, antiinflammatory is administered orally.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (I.e., antigen, antibody or antibody portion) in the required amount in an appropriate solvent with one or a combination of ingredients enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The antiinflammatory of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antiinflammatory of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

As mentioned hereinbefore, compounds 1-10 described herein and pharmaceutically acceptable analogues thereof have use in the prevention and treatment of clinical conditions that involve the COX enzyme(s) that result in an inflammatory condition. For example, the ability of the compounds of invention to interact with the COX enzyme(s), renders them useful for the prophylaxis and treatment of inflammatory states associated with spasmogenic conditions, allergic conditions, conditions involving blood platelet aggregation, and more generally recognized inflammatory conditions.

Examples of spasmogenic conditions are those involving smooth muscle tissue, especially airway smooth muscle constriction such as asthma (including idiopathic bronchial asthma), bronchitis and arterial smooth muscle constriction such as coronary spasm (including that associated with myocardial infarction, which may or may not lead to left ventricular failure resulting in cardiac asthma), ischemia-induced myocardial injury, and cerebral spasm or stroke (which may lead to central nervous pathophysiology). Other examples include bowel disease caused by abnormal colonic muscular contraction such as the conditions known as inflammatory bowel disorder, spastic colon and mucous colitis.

Examples of allergic conditions are extrinsic asthma, allergic skin diseases having a total or partial allergic origin, such as eczema, allergic bowel diseases (including coeliac disease), allergic eye conditions, such as hayfever (which may additionally or alternatively affect the upper respiratory tract), allergic rhinitis, and allergic conjunctivitis.

Examples of conditions involving blood platelet aggregation are those resulting from thrombosis, including strokes having a total or partial thrombotic origin, coronary thrombosis, phlebitis and phlebothrombosis (the latter two conditions also possibly being associated with inflammation).

Examples of inflammatory conditions are those of the lungs, joints, eyes, bowel, skin, and heart; particularly those associated with the infiltration of leucocytes into inflamed tissue. Inflammatory lung conditions include asthma, adult respiratory distress syndrome, bronchitis and cystic fibrosis (which may additionally or alternatively involve the bowel or other tissue(s)). Inflammatory joint conditions include rheumatoid arthritis, rheumatoid spondylitis, osteoarthritis, gouty arthritis and other arthritic conditions. Inflammatory eye conditions include uveitis (including iritis) and conjunctivitis. Inflammatory bowel conditions include Crohn's disease, ulcerative colitis and distal proctitis.

Inflammatory skin diseases include those associated with cell proliferation, such as psoriasis, eczema, dermatitis, including eczematous dermnatitides, such as atopic and seborrheic dermatitis, allergic or irritant contact dermatitis, eczema craquelee, photoallergic dermatitis, phototoxic dermatitis, phytophotodermatitis, radiation dermatitis, and stasis dermatitis. Inflammatory skin diseases also include, but are not limited to, ulcers and erosions resulting from trauma, burns, bullous disorders, or ischemia of the skin or mucous membranes; several forms of ichthyoses; epidermolysis bullosae; hypertrophic scars and keloids; cutaneous changes of intrinsic aging and photoaging; frictional blistering caused by mechanical shearing of the skin; and cutaneous atrophy resulting from the topical use of corticosteroids. Additionally, inflammatory skin conditions include inflammation to mucous membranes, such as cheilitis, chapped lips, nasal irritation and vulvovaginitis.

Inflammatory conditions of the heart include coronary infarct damage. Other inflammatory conditions include tissue necrosis in chronic inflammation, endotoxin shock, smooth muscle proliferation disorders (for example, restenosis following angioplasty), and tissue rejection following transplant surgery.

Additional examples of disease states associated with inflammation are included, as described below. All examples of disease states that exhibit an inflammatory state or condition cited throughout this specification are included within the concept of the invention to treat inflammation. Further, these lists of inflammatory conditions are exemplary, and are not exhaustive. Those skilled in the art would recognize additional inflammatory conditions that fall within the concept of alleviating inflamed conditions wherein PMNs and/or leukocytes are locally increased, relative to baseline conditions, due to an injury, an insult, or a stimulant to the subject's physiology.

Accordingly, the present invention provides a method for the prevention or treatment of a clinical condition in a subject is indicated, such as, a spasmogenic condition, an allergic condition, a condition involving blood platelet aggregation, or an inflammatory condition. The treatment includes administration of a therapeutically effective amount of one or more of compounds 1 through 10 of the invention, or a pharmaceutically acceptable analogue as described herein. The present invention still further provides a method for the prevention or treatment of neurodegeneration or dementia associated with HIV infection in a subject that includes administration of a therapeutically effective amount of one or more of compounds 1 through 10 of the invention, or a pharmaceutically acceptable analogue as described herein.

In one embodiment, the antiinflammatories of the invention can be incorporated into a shampoo or a body cleansing product, e.g., a soap, for cleansing of the scalp and/or body. The use of these compounds in a shampoo or soap product can be used to treat psoriasis, seborrheic dermatitis, pustular dermatosis and dandruff. Additionally, the antiinflammatories of the invention, e.g. compound 1 through 10, and combinations thereof, can be used in topical lotions to treat the above-mentioned diseases as well as sunburn, poison ivy, dermatitis, and to slow the growth of metastatic cancers. Alternatively, the compounds of the invention can be used to treat Alzheimer's disease, where it is known that the action of antiinflammatories helps to reduce the long term effect(s) of plaquing. In an alternative embodiment, the compounds of the invention can be used in an aerosol or spray to treat airway inflammation, e.g., bronchitis, asthma, pneumonia, emphysema, and upper respiratory illnesses in general.

Supplementary active compounds can also be incorporated into the compositions. In certain embodiments, an antiinflammatory of the invention is coformulated with and/or coadministered with one or more additional therapeutic agents that are useful for treating disorders in which inflammation is detrimental. For example, an antiinflammatory of the invention may be coformulated and/or coadministered with one or more additional antiinflammatory compounds that bind other targets, e.g., receptors. Furthermore, one or more antiinflammatories of the invention may be used in combination with two or more of the foregoing therapeutic agents. Such combination therapies may advantageously utilize lower dosages of the administered therapeutic agents, thus avoiding possible toxicities or complications associated with the various monotherapies.

Surprisingly, it has been unexpectedly discovered that the interaction between aspirin, COX-II and omega-3 fatty acids has an anti-inflammatory effect upon tissue(s). Moreover, this combination produces unique compounds having the above-identified formulae. These compounds have anti-inflammatory properties and can be used as anti-inflammatory agents for treatment of disease states or conditions which have inflammation associated with these diseases or conditions.

Two classes of eicosanoids, namely LT and certain PG, mediate important actions relevant to human disease. Although the pro-inflammatory roles of LT and PG are established (See FIG. 1), the present invention provides new evidence that previously unknown LM and their stable analogs have potent counterregulatory actions in PMN-mediated tissue injury and acute inflammation. Along these lines, it is known that the oxidation of arachidonic acid in endothelial cells (EC) can lead to 11,12-EET via p450 displaying antiinflammatory properties blocking leukocyte adhesion molecules, and non-enzymatic oxidation of EPA also gives products yet to be identified that downregulate EC.

The present findings provide that the integrated host response, recognized as human diseases such as arterial inflammation, arthritis, cardiovascular diseases, geriatric inflammatory disorder, irritable bowel (colon), erysipelos, eczematoas, psoriasis, urticara, vasculitis, AIDS associated inflammation, ocular inflammation, asthma, pulmonary inflammation, pulmonary fibrosis, in part, reflects an overall balance between "pro" and "anti"-inflammatory signals". Among such signals, the role of LM remained to be established, likely because these products are rapidly generated, often via transcellular biosynthesis, are short-lived and act locally. In this regard, the lipoxins (LX) and recently elucidated aspirin-triggered LX (ATL) from arachidonic and their metabolically stable analogs have been of interest because prolonging their bio-half life enhances their in vivo beneficial actions.

Figure 4:
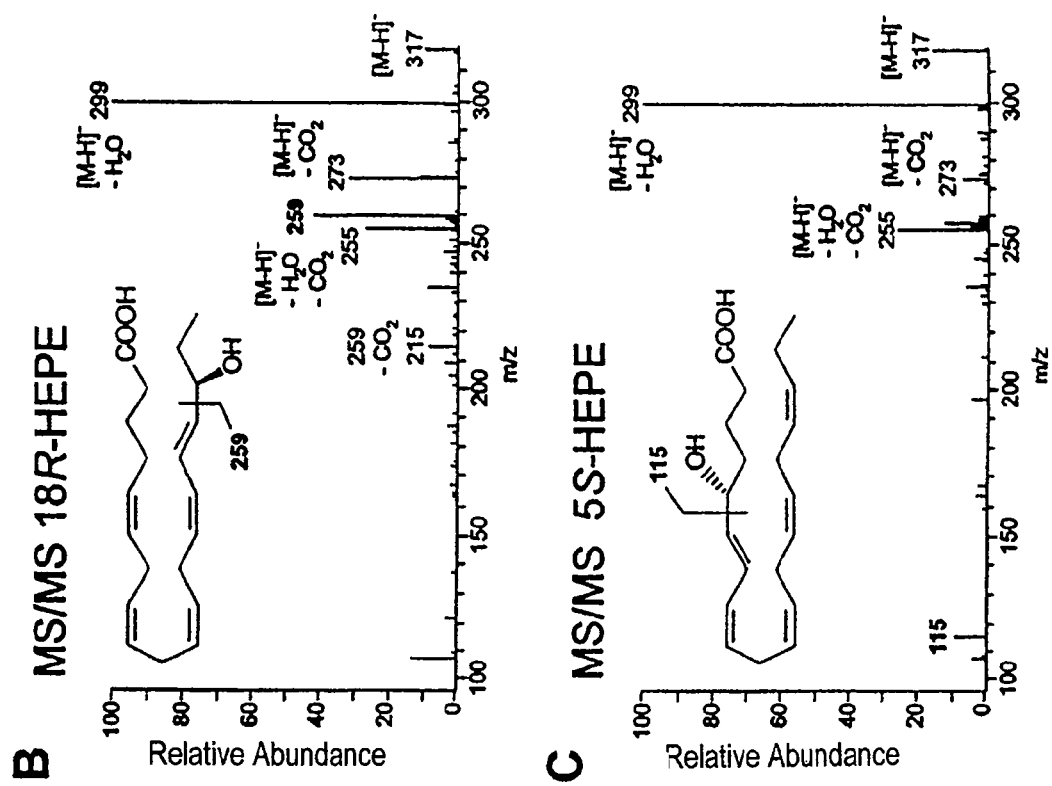
FIG. 4A is an LC/MS ion chromatogram of monohydroxy products generated from EPA in aspirin-treated murine dorsal air pouch inflammatory exudates.
FIG. 4B is a mass spectral analysis of 18R-HEPE generated from EPA in aspirin-treated murine dorsal air pouch inflammatory exudates.
FIG. 4C is a mass spectral analysis of 5S-HEPE generated from EPA in aspirin-treated murine dorsal air pouch inflammatory exudates.
FIG. 4D is a mass spectral analysis of 5,12,18R-triHEPE generated from EPA in aspirin-treated murine dorsal air pouch inflammatory exudates.
Figure 1:
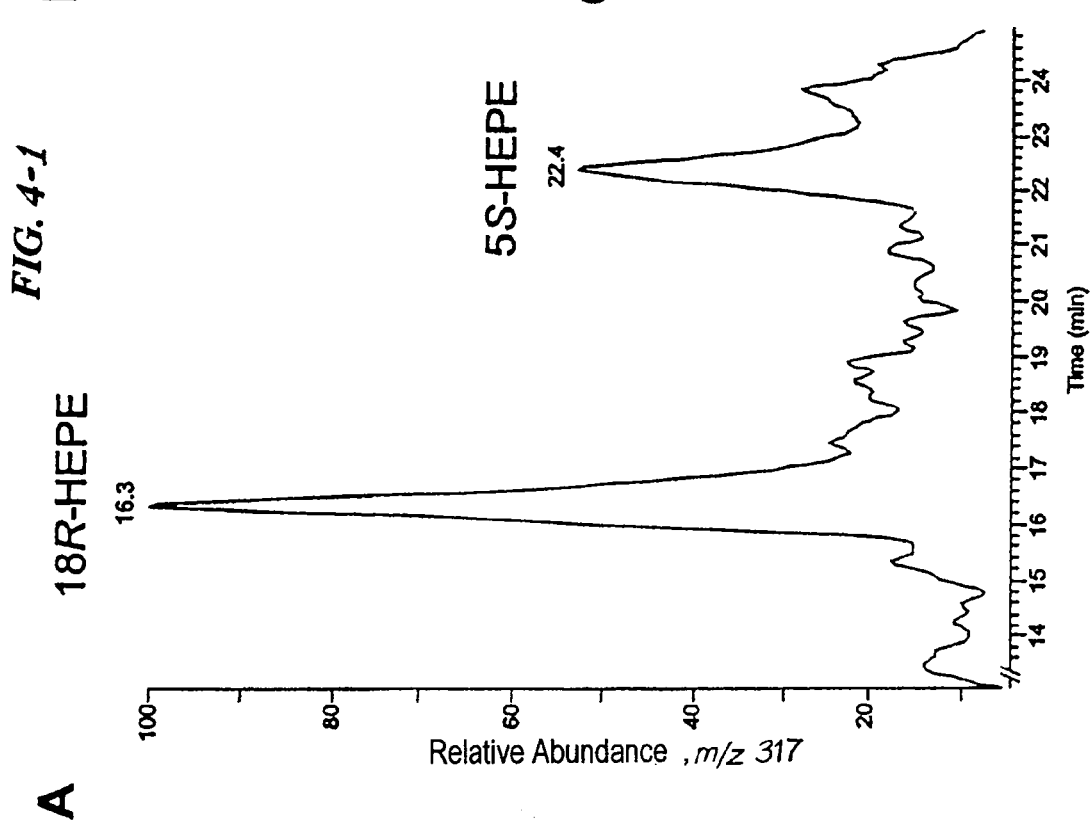
Figures 2, 4:
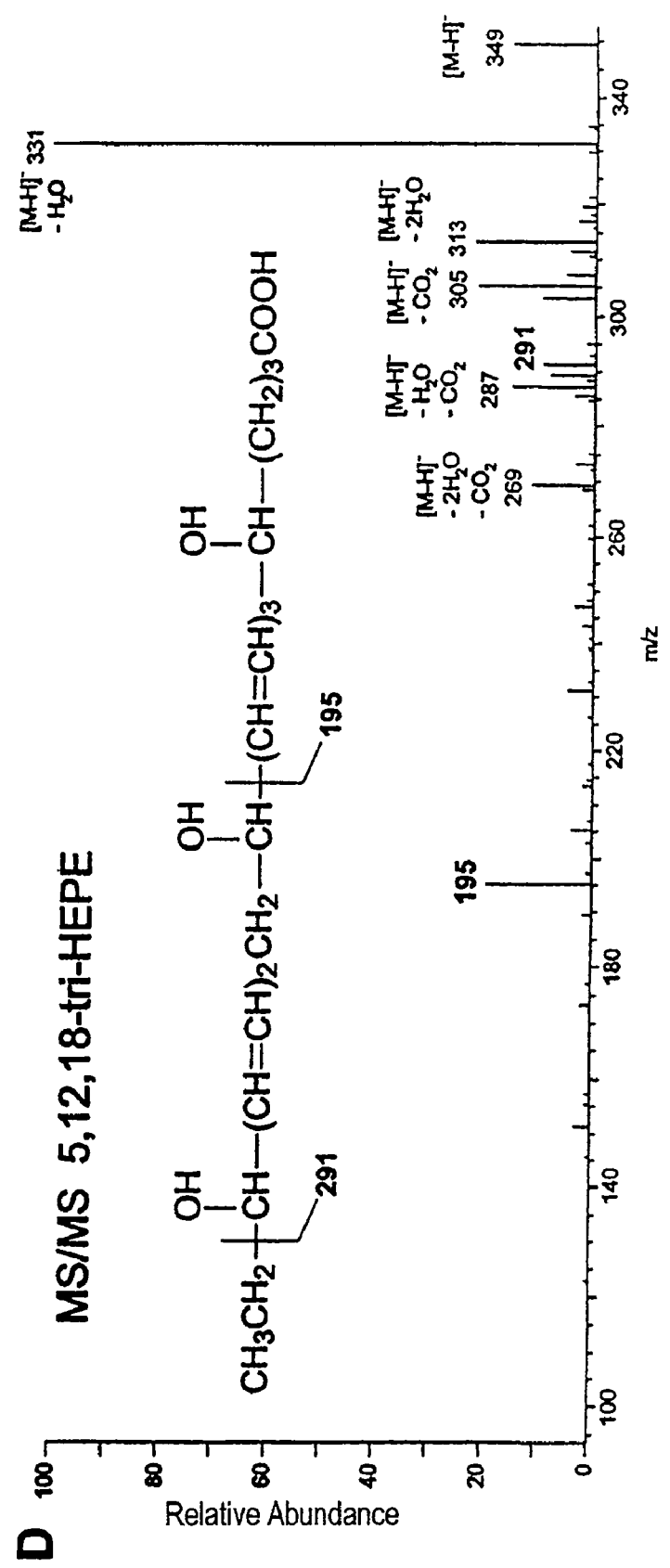

Because ASA triggers formation of epimeric forms of naturally occurring bioactive eicosanoids (Reference 9), the concept that NSAIDs might promote the formation of novel mediators from ω-3 PUFAs was tested. Inflammatory exudates formed in murine air pouches via intrapouch injections of TNF-α with ω-3 and ASA on board (2 h) generated several novel compounds (FIG. 4). These mice were fed a standard rodent diet containing 0.26% ω-3 PUFA. LC/MS/MS analyses of the exudate-derived-materials demonstrated monohydroxy acids, depicted in selected ion chromatograms from acquired results recalled at m/z 317 (FIG. 4A), i.e., 18-hydroxy-EPA (18-HEPE) and 5-HEPE, which coeluted with synthetic 5S-HEPE as well as novel trihydroxy-containing compounds derived from C20:5. LC retention times and MS/MS spectra (FIGS. 4B and 4C) gave product ions consistent with structures shown in the respective insets, namely m/z 317=(M-H)~-$H_2O$—$CO_2$. Diagnostic ions consistent with 18-HEPE identification were present at m/z 259 (FIG. 4B) and 5-HEPE at m/z 115 (FIG. 4C). These criteria were used throughout for identification. The stereochemistry of the alcohol at carbon 18 was established for exudate-derived 18-HEPE using a chiral column, and a reference 18R-HEPE was prepared via biogenic synthesis using *B. megaterium* (see FIGS. 5A-5C, Materials and Methods). This microbe monoxygenates fatty acids and, for example, converts C20:4 to 18R-HETE (22. Capdevila, J. H., S. Wei, C. Helvig, J. R. Falck, Y. Belosludtsev, G. Truan, S. E. Graham-Lorence, and J. A. Peterson. 1996. The highly stereoselective oxidation of polyunsaturated fatty acids by cytochrome P450BM-3. *J. Biol. Chem.* 271:22663-22671; and 23. Ruettinger, R. T., and A. J. Fulco. 1981. Epoxidation of unsaturated fatty acids by a soluble cytochrome P-450-dependent system from *Bacillus megaterium*. *J. Biol. Chem.* 256:5728-5734). The alcohol configuration at position 18 proved to be >98% R. These findings indicated that murine inflammatory exudates exposed in vivo to C20:5, ω-3 and ASA produced 5-lipoxygenase pathway 5-series 5S-HEPE, a product also identified with human PMNs, as well as a novel 18R-HEPE, whose route of formation was determined (vide infra) (24. Lee, T. H., J. M. Menica-Huerta, C. Shih, E. J. Corey, R. A. Lewis, and K. F. Austen. 1984. Characterization and biologic properties of 5,12-dihydroxy derivatives of eicosapentaenoic acid, including leukotriene B5 and the double lipoxygenase product. *J. Biol. Chem.* 259:2383-2389). Air pouch inflammatory exudate cells from these ASA- and EPA-treated mice contained predominantly PMN (as in FIG. 4), which were 25-50% lower in number than in exudates formed with TNF-α alone (n=3 illustrated in FIG. 6). Also, these exudates, when activated with ionophore $A_{23187}$ (4 μM), generated essentially equivalent amounts of 18R-HEPE (10.2±4.3 ng/$10^4$ cells) and 5S-HEPE (10.9±2.9 ng/$10^4$ cells). FIGS. 4A-D depict inflammatory exudates from Murine Dorsal Pouches treated with Aspirin to generate novel compounds shown by LC/MS/MS; TNFα-induced leukocyte exudates were collected at 6 h from FVB mice given ASA (3.5 h at 500 μg/air pouch) and EPA (4 h at 300 μg/pouch), contained 2.3+/–0.5×$10^6$ leukocyts/pouch) (See Methods);

Evidence for novel trihydroxy-containing products was also obtained in these inflammatory exudates (FIG. 4D). Ions present within MS/MS were consistent with a trihydroxy-containing product from 20:5 with a parent ion at m/z 349= (M-H)— and product ions of structural significance present at m/z 291 and 195 that are consistent with fragmentation denoted in the inset (FIG. 4D). Also, an observed 270 nm UV absorbance maximum indicative of a conjugated triene, together with the presence of the m/z 291 (cleavage C17-C18 positions) as well as the 20-carbon structure, implicated that 18R-HEPE and the triHEPE were biosynthetically related.

It was of interest to determine whether these new compounds were also generated by human cells and if they possess bioactivities. To this end, human ECs known to induce COX-2 with IL-1β or hypoxia (not shown) were pulsed with EPA and treated with ASA, and extracted materials were subject to LC/MS/MS analysis (FIG. 7A). Selected ion monitoring at m/z 259 revealed that HUVECs treated with ASA converted EPA to 18R-HEPE (FIG. 7A). Also, HMVECs created with ASA and EPA generated 18-HEPE (10.6 ng/$10^4$ cells) and 15-HEPE (6.0 ng/$10^6$ cells) (n=2, four determinations; data now shown). These observations implicated the involvement of COX-2 in the generation of these compounds, which proved to be the case with recombinant human COX-2 exposure to ASA and ω-3 PUFA (FIGS. 8A-8D and Table 1), findings that are of clinical significance.

Figure 2A:
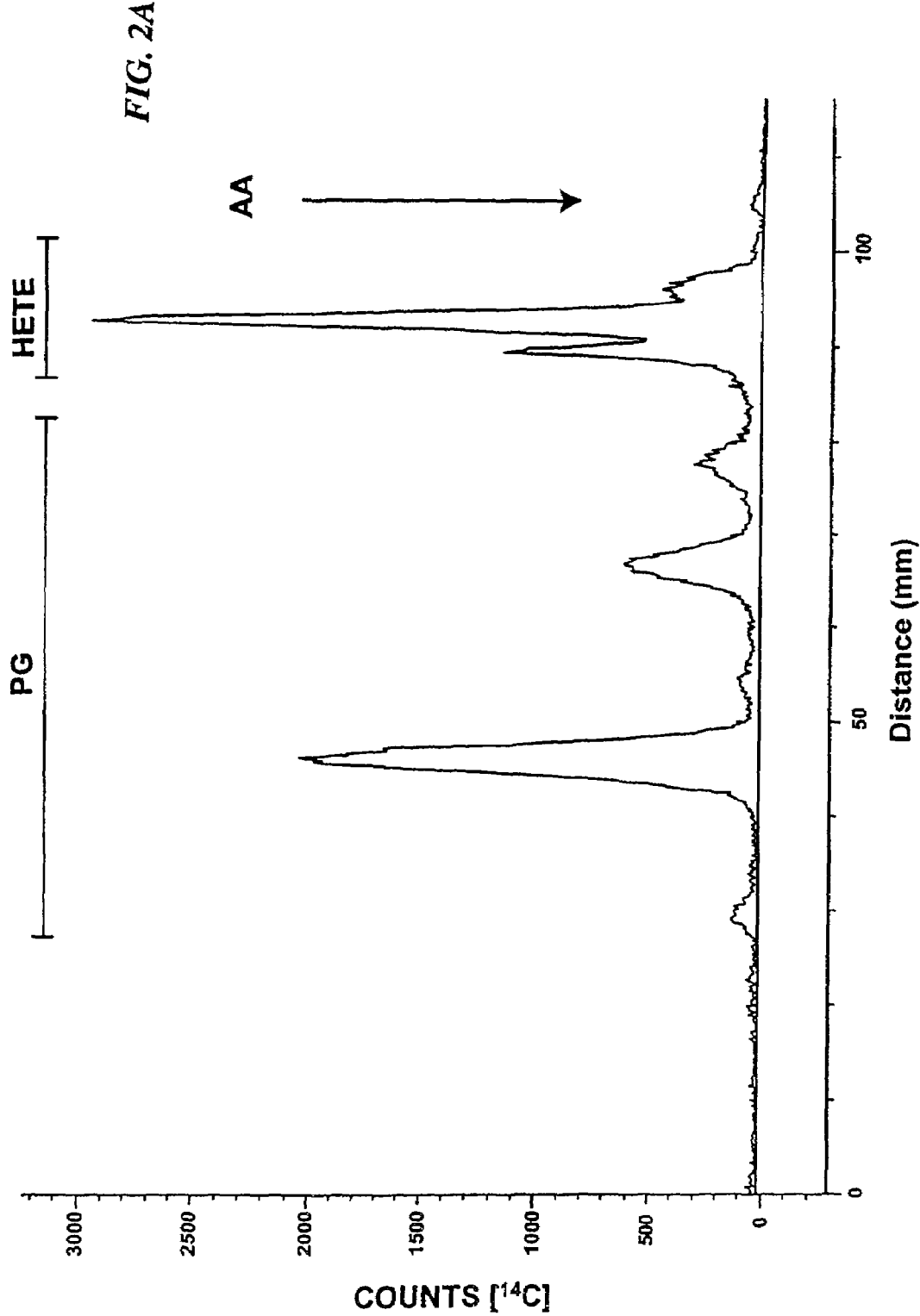
FIG. 2A depicts a thin layer chromatogram of products generated from $^{14}$C-labeled arachidonic acid (AA, ω-6) by cyclooxygenase 2 (COX-2).
Figure 2D:
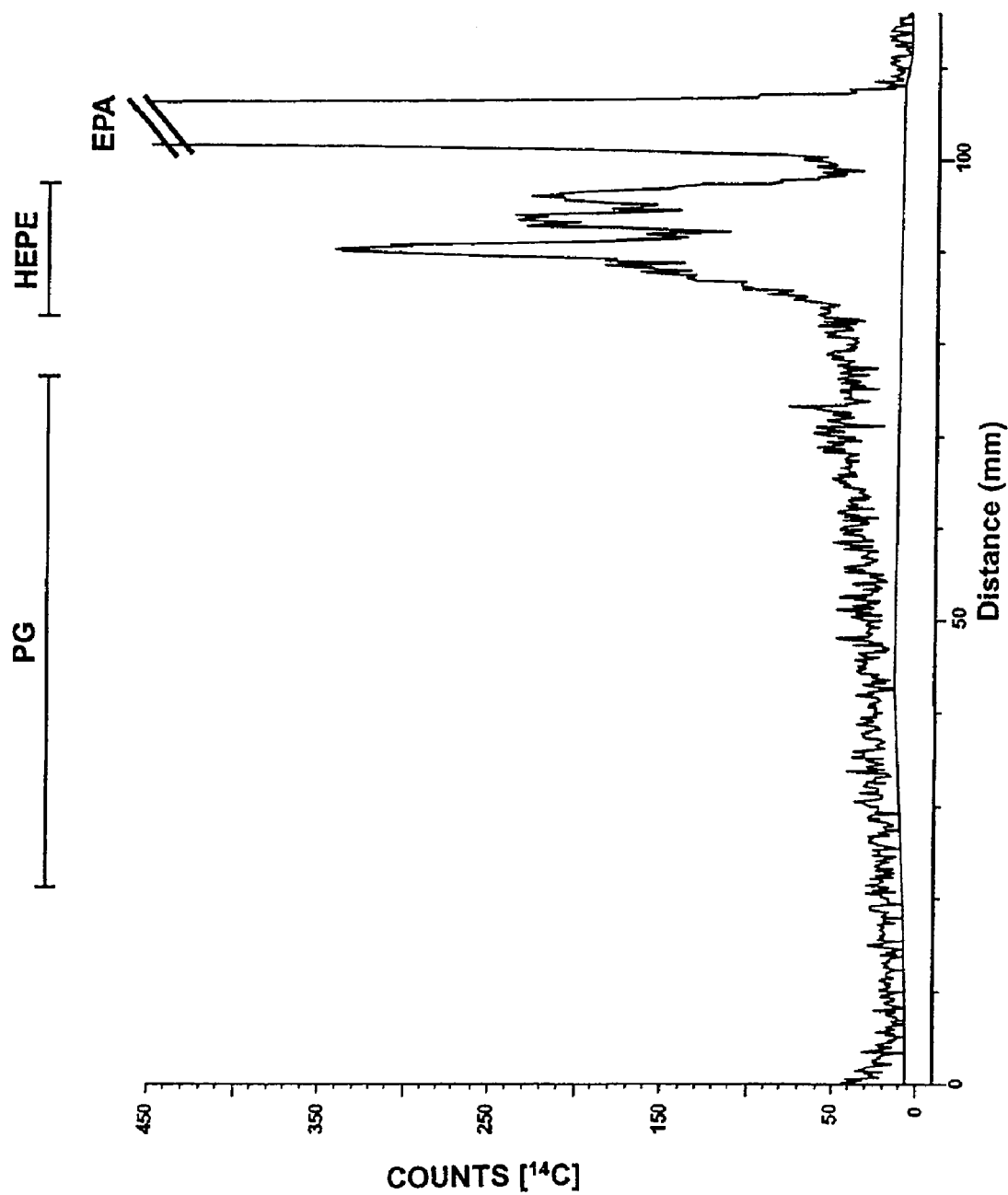
FIG. 2D depicts a thin layer chromatogram of products generated from $^{14}$C-labeled EPA(ω-3) by aspirin acetylated-COX-2.
Figures 1, 3:
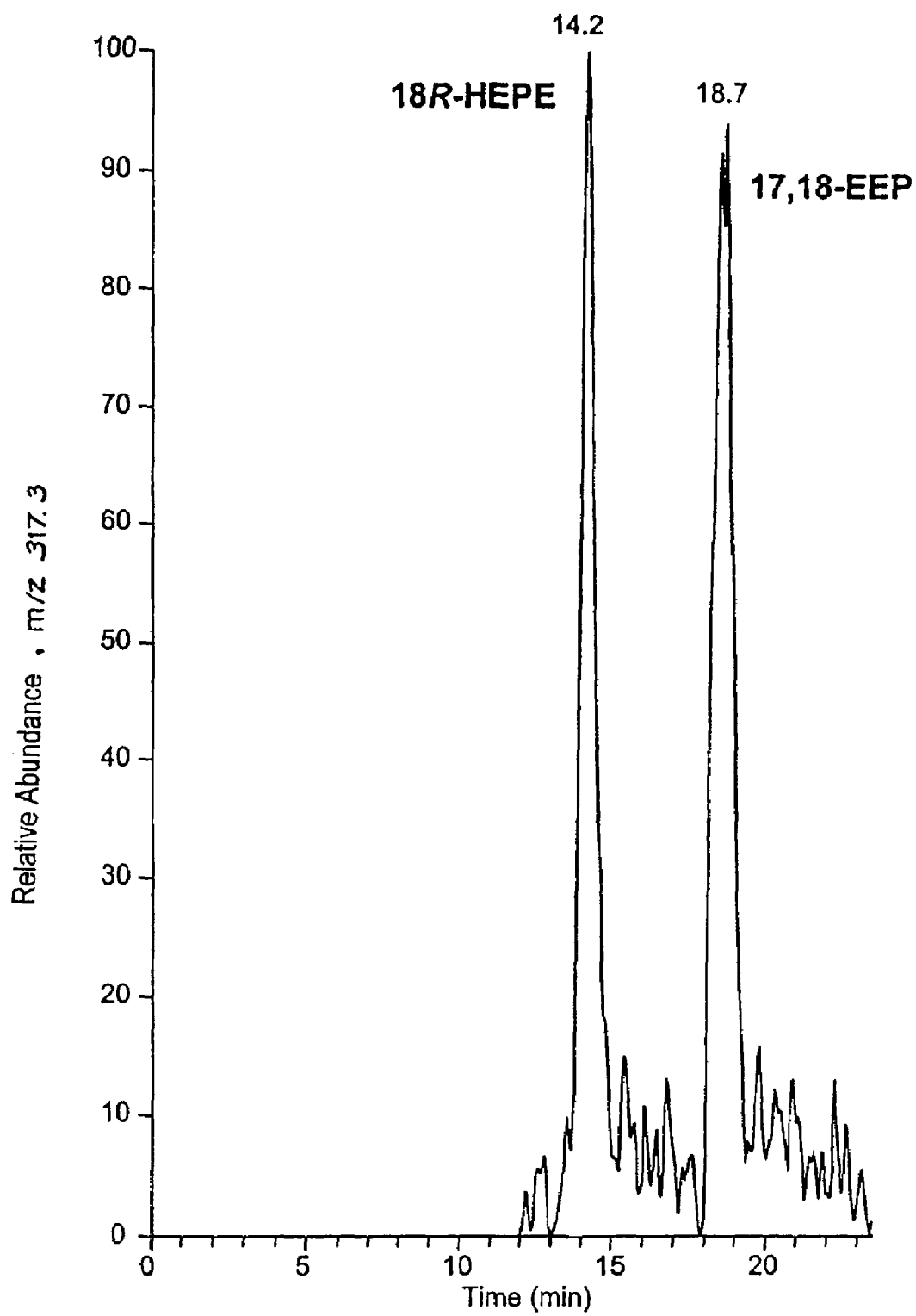
Figure 3:
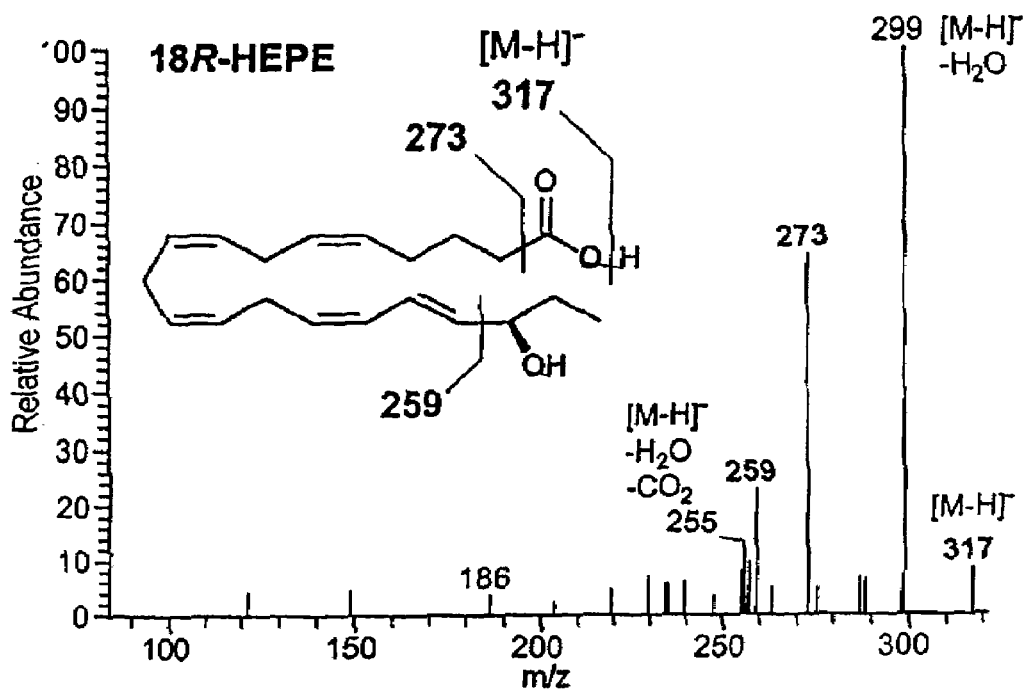
FIG. 3A-3C depict conversion of EPA (ω-3) by *B. megaterium* via LC/MS ion chromatogram and mass spectral analysis.
Figure 2:
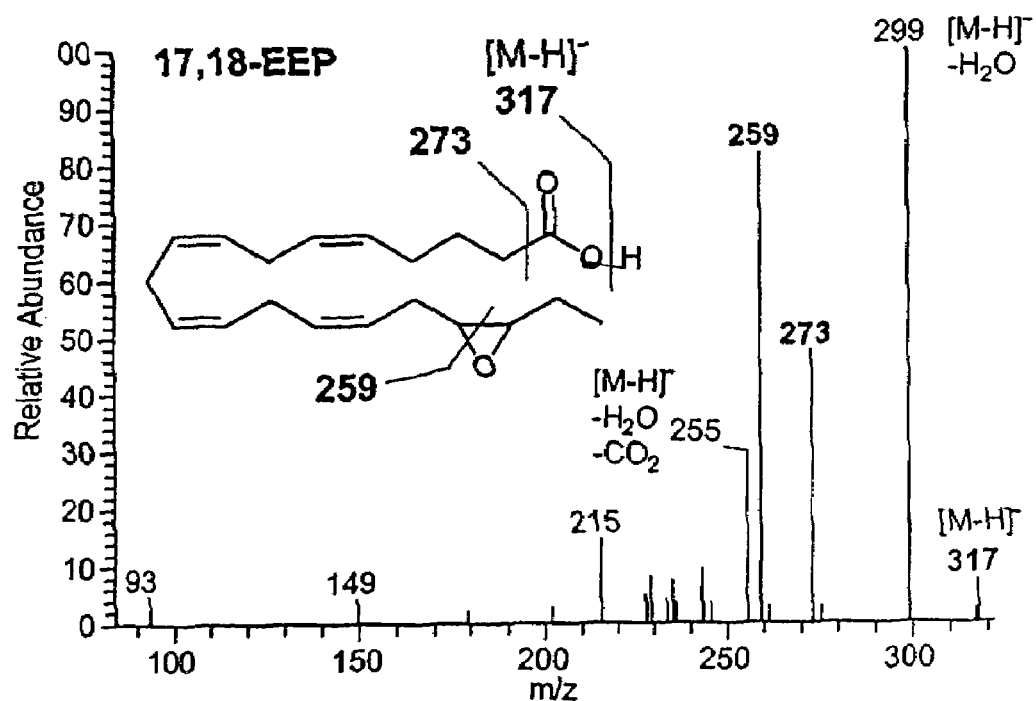
FIG. 2B depicts a thin layer chromatogram of products generated from $^{14}$C-labeled AA(ω-6) by aspirin acetylated-COX-2.
FIG. 2C depicts a thin layer chromatogram of products generated from $^{14}$C-labeled eicosapentaenoic acid (EPA, ω-3) by cyclooxygenase II (COX-2).

As shown in Table 1, linoleic acid (C18:2) was converted to both 13-hydroxy-9Z, 11E-octadocadienoic acid (13-HODE; n-5 oxygenation) and 9-HODE (ω-9), which were greatly diminished by ASA but not completely abolished. AA was converted to 15R-HETE (n-5) as well as 11R-HETE (n-9), consistent with earlier findings. ASA triggered the appearance of lipoxygenase activity that switched to 15R-HETE production by acetylated COX-2 (References 9, 14, 15), which did not appear to influence 11R-HETE formation (Table 1 and FIG. 8). 11R-HEPE was the major product with EPA and COX-2, with lesser amounts of 15R-HEPE (n-5) and 18R-HEPE (n-2). 1-$^{14}$C-labeled EPA was used to confirm precursor-product relationships (n=3 as in FIG. 2 in Methods). ASA acetylation of COX-2 (FIGS. 8A-8D for identification of each of the novel reaction products and indicated within their respective mass spectrum) led to an approximately twofold increase in 18R-HEPE (n-2), with a >85% reduction in 11R-HEPE (the ratio of positional oxygenation with C20:5 was 1:1:0.3, with 18R~15R>11R). Hence, together they suggested that acetylated COX-2 in ECs (FIG. 7) was a dominant source of 18R-HEPE and 15R-HEPE.

Figure 6:
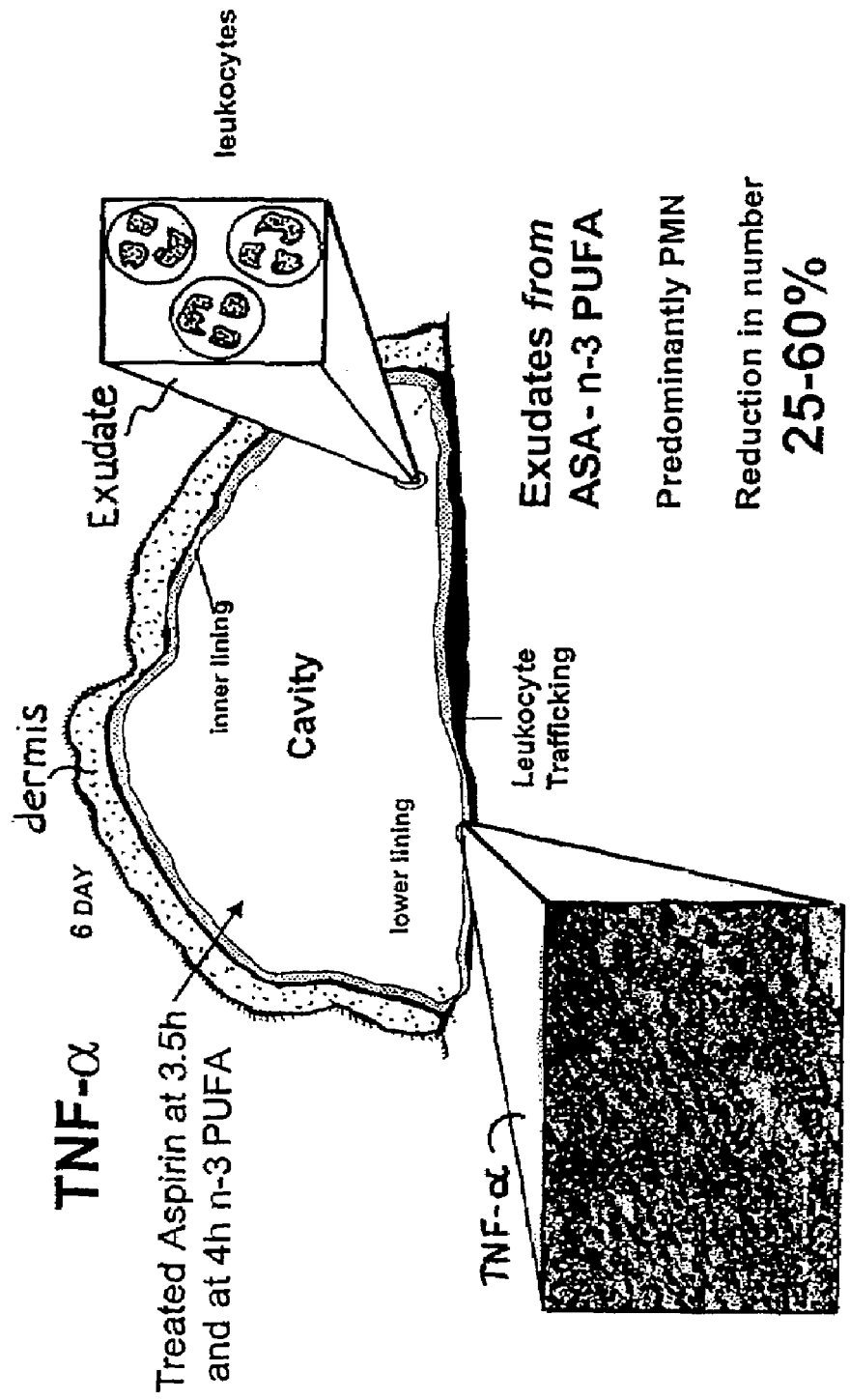
FIG. 6 depicts a murine dorsal air pouch treated with tumor necrosis factor-alpha (TNF-α) and aspirin.
Figures 1, 7:
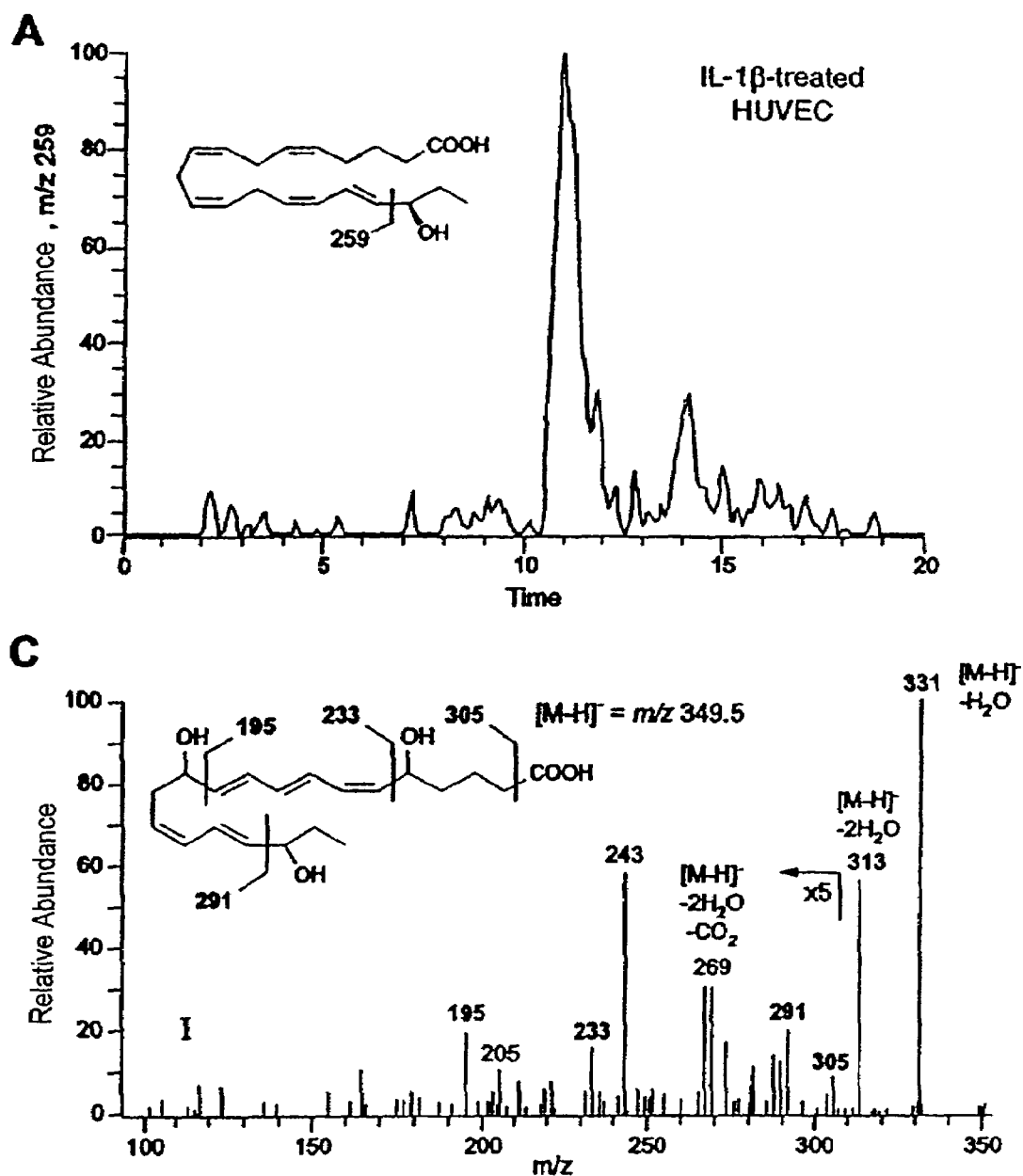
Figures 2, 7:
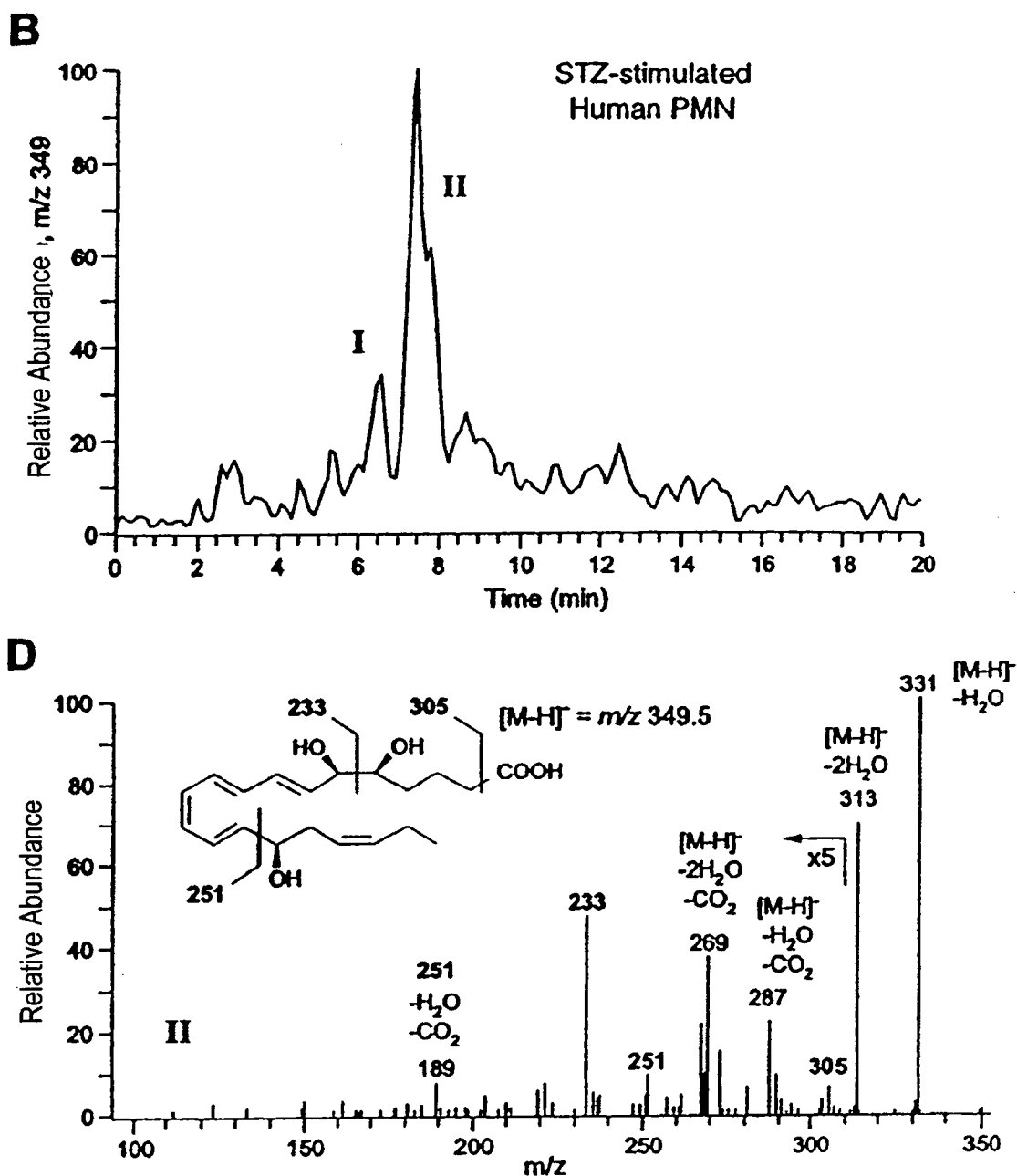
FIG. 7A depicts an LC/MS ion chromatogram of 18R-HEPE generated from IL-1β-stimulated human umbilical cord endothelial cells (HUVEC) treated aspirin and EPA.
FIG. 7B depicts an LC/MS ion chromatogram of triHEPEs generated from EPA by aspirin acetylated-COX-2 and serum treated zymosan (STZ)-stimulated human PMN.
FIG. 7C depicts a mass spectral analysis of triHEPE product I, 5,12,18R-triHEPE, in FIG. 7B.
FIG. 7D depicts a mass spectral analysis of triHEPE product II, 15-epi-LXA$_5$, in FIG. 7B.
Figures 1, 8:
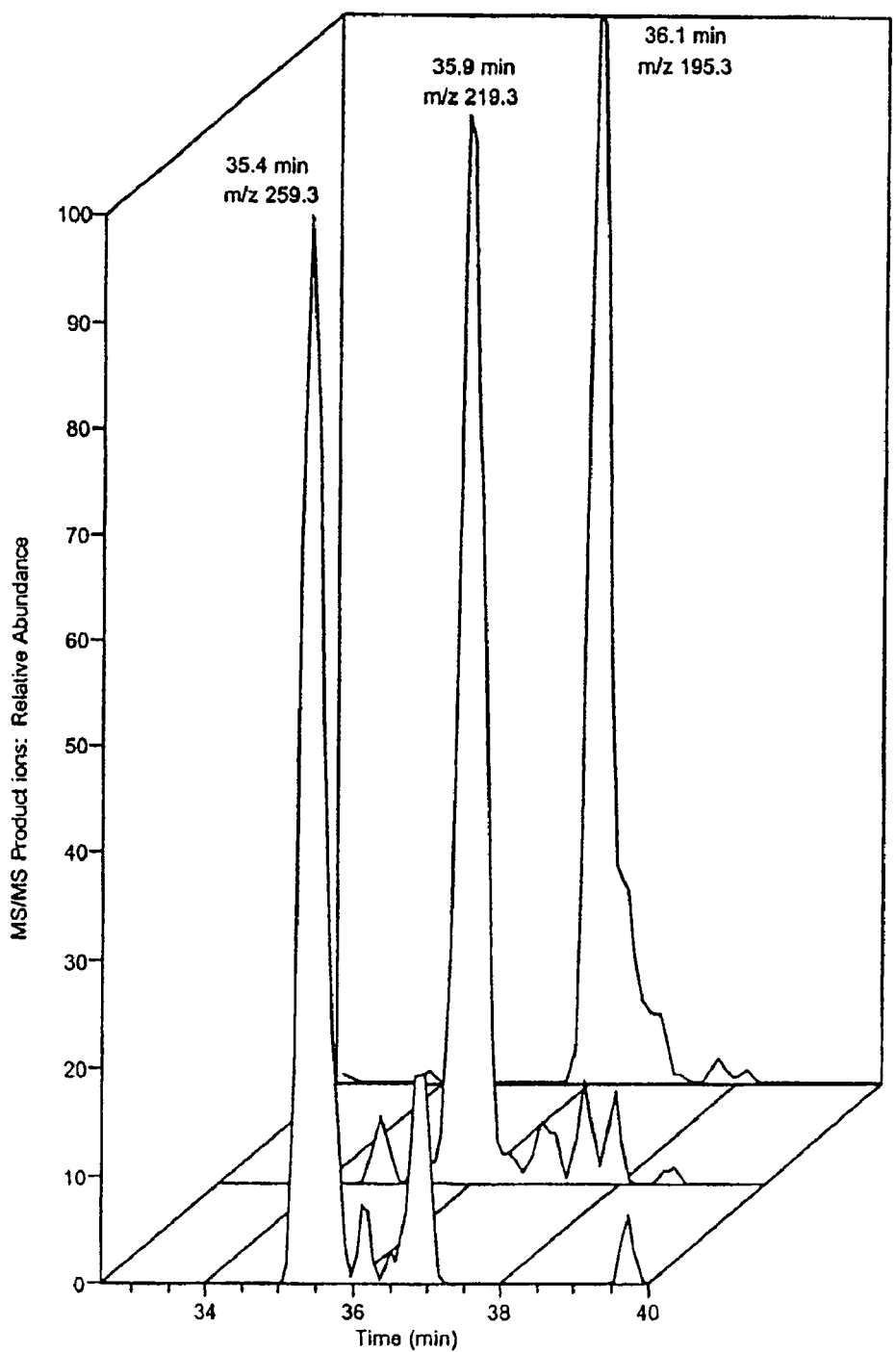
Figures 2, 8:
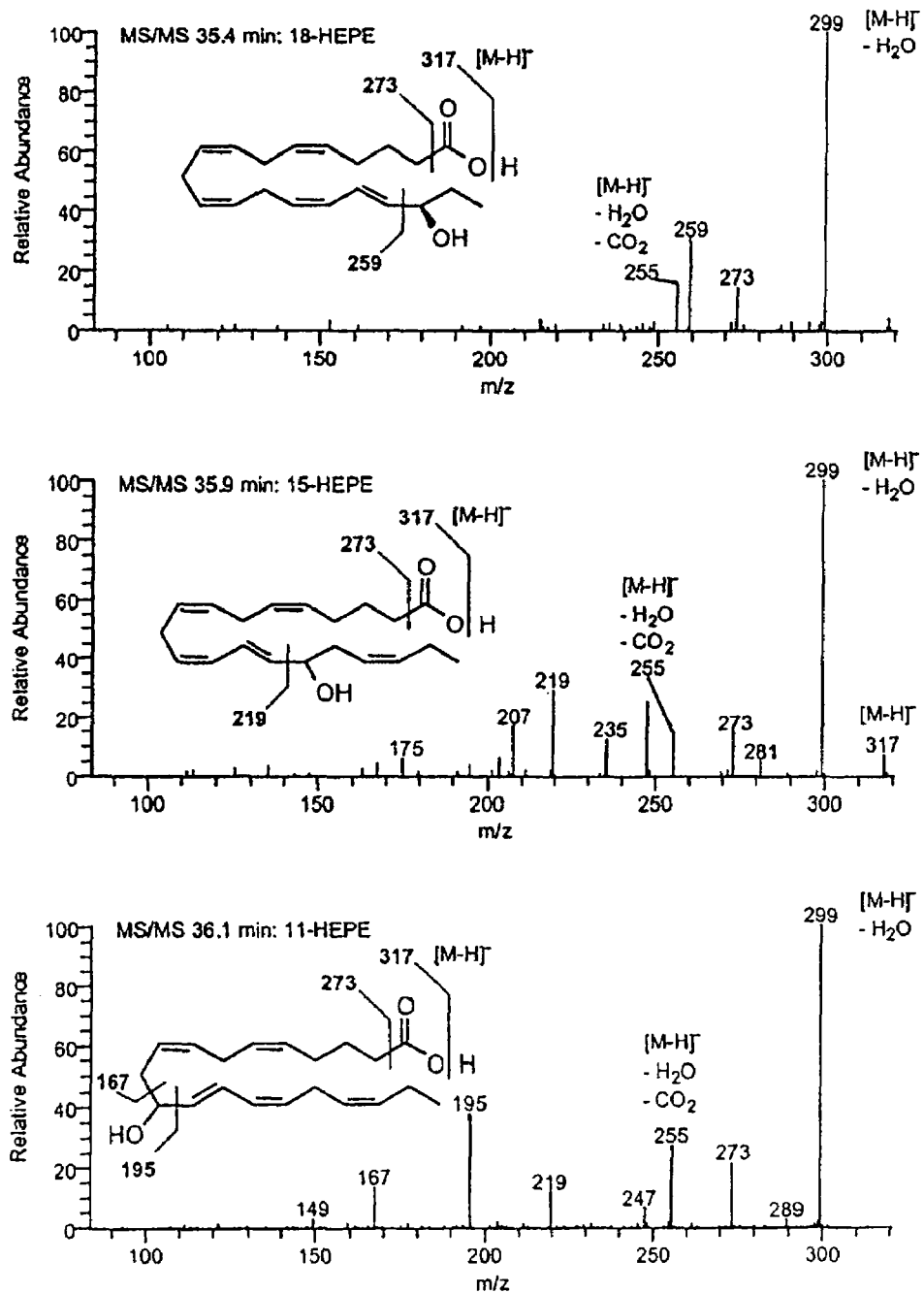
FIG. 8A-8D depict selected ion monitoring LC/MS/MS chromatograms of monhydroxy products generated from EPA by aspirin acetylated-COX-2 with mass spectral analyses of 18-HEPE, 15-HEPE, and 11-HEPE.

Interestingly and unlike the isolated COX-2 product profiles, neither 11R-HEPE (from C20:5) nor 11R-HETE (from C20:4) were major products of the vascular ECs (Table 1 and FIG. 7). With the selective COX-2 inhibitor NS398, these oxygenation were reduced, and only 18R-HEPE formation from EPA appeared to escape inhibition (Table 1). These results suggest that ASA treatment at local sites of inflammation along with ω-3 PUFA (i.e., EPA; C20:5, 6-3) administration, as exemplified by cytosine-drive acute inflammation (FIG. 4 and FIG. 6), can convert EPA via COX-2 to 18R-HEPE and 15R-HEPE.

Because human PMNs convert ASA-triggered, COX-2-derived 15R-HETE to 15-epi-LXA$_4$ (Reference 9) and EPA is converted to 5-series LX (25. Serhan, C. N., P. Y. Wong, and B. Samuelsson. 1987. Nomenclature of lipoxins and related compounds derived from arachidonic acid and eicosapentaenoic acid. *Prostaglandins* 34:201-204.) by human leukocytes as well as trout macrophage (26. Hill, D. J., D. H. Griffiths, and A. F. Rowley. 1999. Trout thrombocytes contain 12- but not 5-lipoxygenase activity. *Biochim. Biophys. Acta* 1437:63-70.), activated human PMNs engaged in phagocytosis handle acetylated COX-2-derived C20:5, ω-3 products 18R-HEPE and 15R-HEPE were evaluated. Serum treated zymosan (STZ), a phagocytic stimulus, indicated the utilization and conversion of acetylated COS-2 C20:5-derived products to two classes of tri-hydroxy-continuing EPE, determined again by selected ion monitoring at m/z 349.5 (M-H)—, the base peak molecular ion for these products (FIG. 7B). One, shown in FIG. 7C, gave essentially the same MS/MS observed in FIG. 4D from murine cells and was consistent with the 5,12,18R-triHEPE structure depicted in the inset giving diagnostic ions (FIG. 7C) as m/z 305, 233, 195, and 291 (FIG. 4D).

This product is an 18R-hydroxy-carrying "LTB$_5$-like" structure (see FIG. 7D, inset). Indeed, when isolated 18R-HEPE was incubated as above with activated PMNs, it was converted to several compounds, including this product. Also, synthetic LTB$_5$ incubated with *B. megaterium* homogenate and NADPH at pH 8.0 to facilitate hydroxylations (Reference 23) was transformed to a trihydroxy product (n=3) with an m/z 291 ion characteristic for the presence of the 18R alcohol group (FIGS. 5A-5C) as obtained from human PMNs show in FIG. 7C. These independent lines of evidence indicated that PMNs take up 18R-HEPE, which is converted by their 5-lipoxygenase, to insert molecular oxygen and in subsequent steps to 5-hydro(peroxy)-18R-DiH(p)EPE and 5(6)epoxide formation to 5,12,18R-triHEPE (an 18R-carrying LTB$_5$-like product) that is likely to posses the stereochemistry of LTB$_5$, retaining the 18R chirality of the precursor.

In an analogous biosynthetic fashion, 15R-HEPE was converted by PMN via 5-lipoxygenation to a 5-series LXA$_5$ analogue (FIG. 7D) that also retains their C15 configuration. Its MS/MS gave prominent ions, m/z 305, 233, and 251, depicted in the MS/MS spectrum, namely 15-epi-LXA$_5$, consistent with 15S-containing LX$_5$ structures (5-series) observed from endogenous sources of EPA in trout macrophages. In this case, the chirality of the precursor 15R is retained by human PMN to give 15-epi-LXA$_5$ (FIG. 7D), which is the 5-series ω-3 analogue of 15-epi-LXA$_4$. As with LX biosynthesis, conversion of both 18R- and 15R-HEPE by activated PMNs with 5-lipoxygenation was accompanied with a reduction in LTB$_4$, formation (not shown). Together, these results indicate that isolated human ECs and PMNs (FIG. 7) can generate the novel products observed with inflammatory exudates (FIGS. 1-4 and Table 1 and 2).

Figure 9:
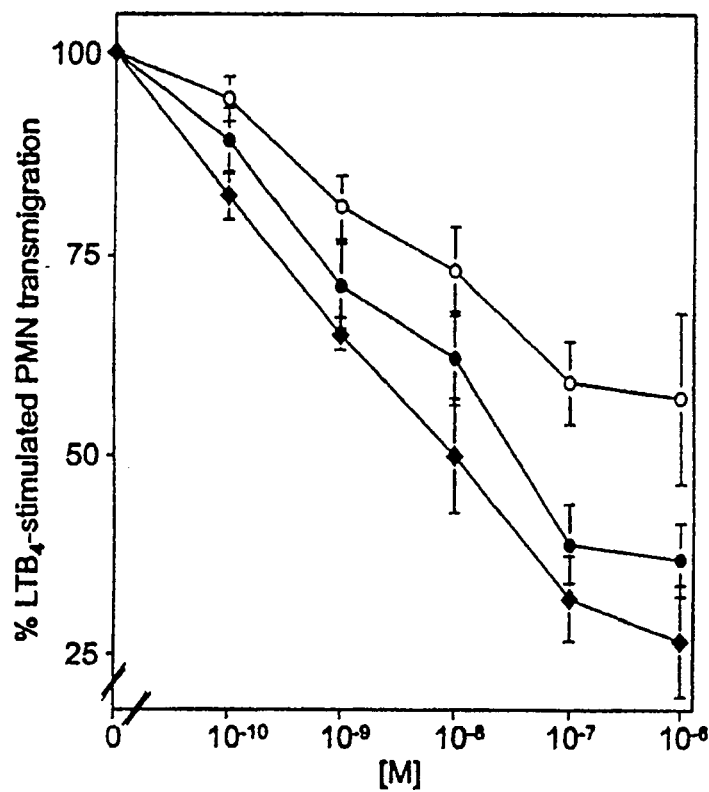
FIG. 9A shows inhibition of LTB$_4$-stimulated PMN transendothelial migration by 18R-HEPE (open circles), 5,12,18R-triHEPE (closed circles), and an aspirin-triggered lipoxin (ATL) analog reference compound (closed square).
FIG. 9B shows competition binding between either 18R-HEPE (open circles), 5,12,18R-triHEPE (closed circles), LTB$_5$ (open square), or homoligand LTB$_4$ (closed square) with $^3$H-LTB$_4$ on recombinant human LTB$_4$ receptor stably expressed in HEK-293 cells.
FIG. 9C depicts the inhibition of TNF-α induced leukocyte trafficking into the murine dorsal air pouch following intravenous injection of 100 ng of either 18R-HEPE, 5,12,18R-triHEPE, or an ATL analog reference compound (analog 15(S)-16(para-fluoro)-phenoxy-LXA$_4$ used for comparison, results represent N=4.
Figure 1:
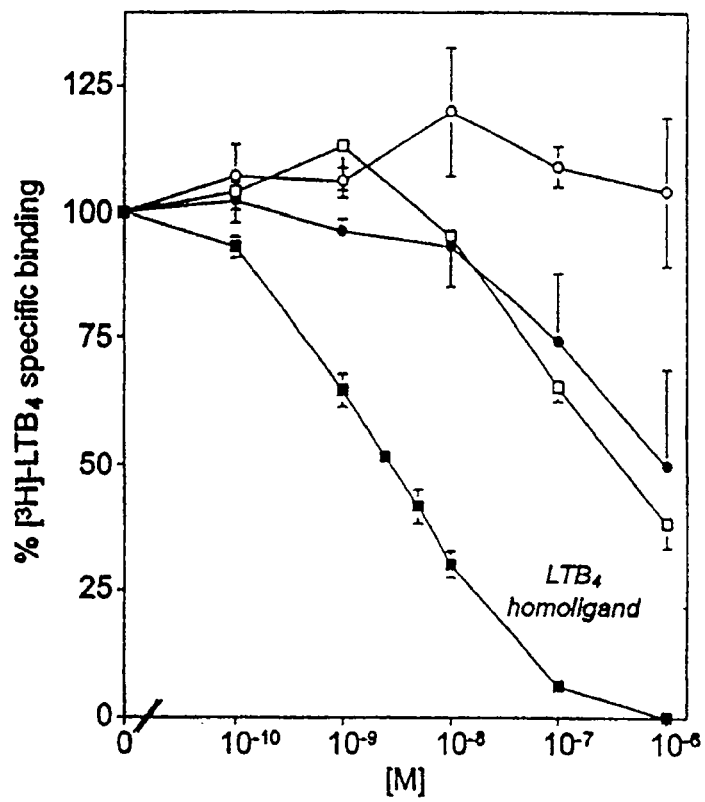
Figures 2, 9:
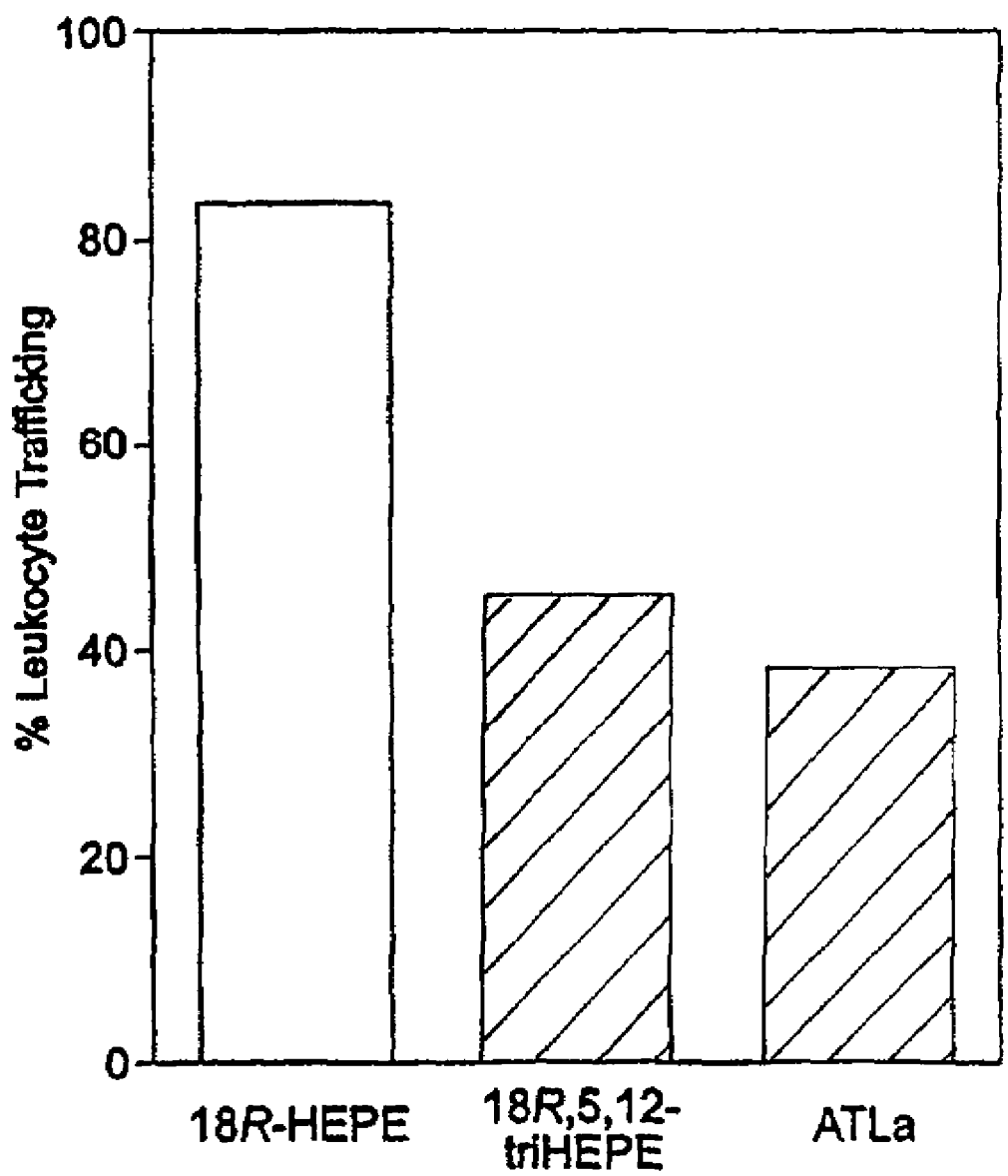
Figures 1, 10A:
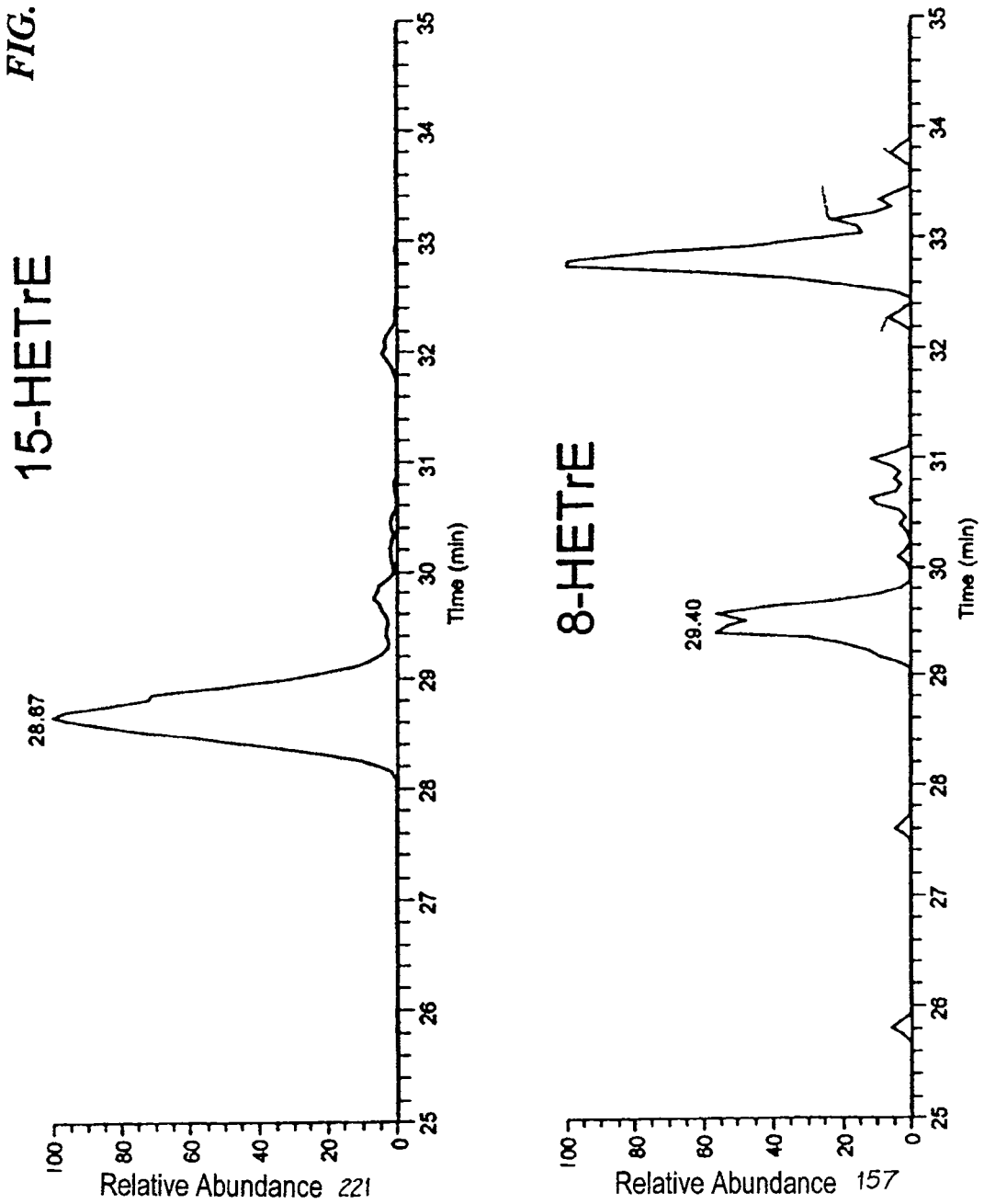
Figure 10A:
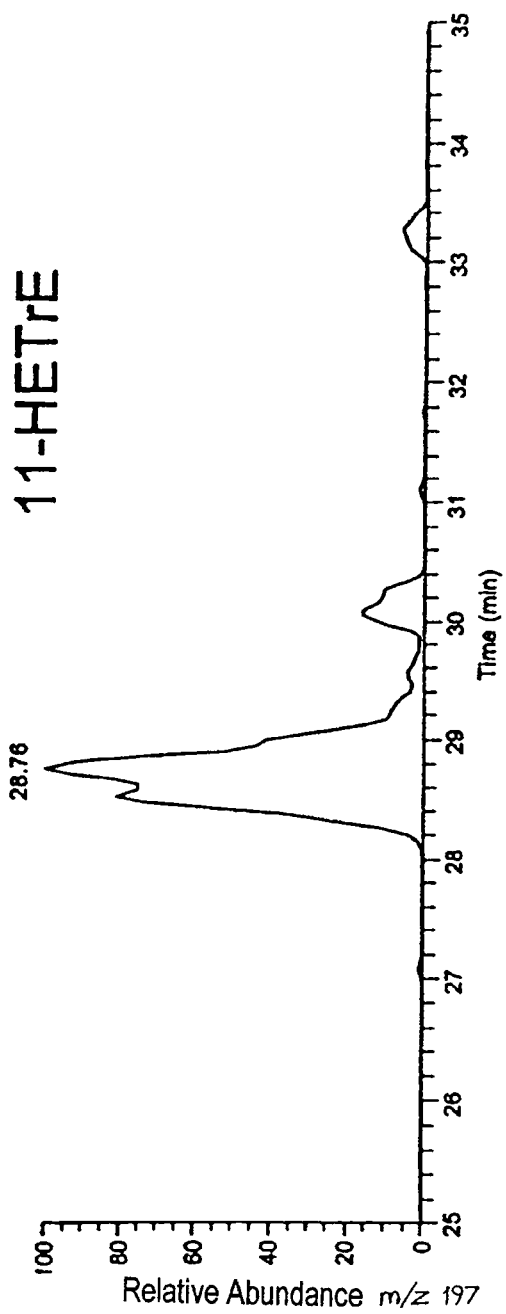
Figure 2:
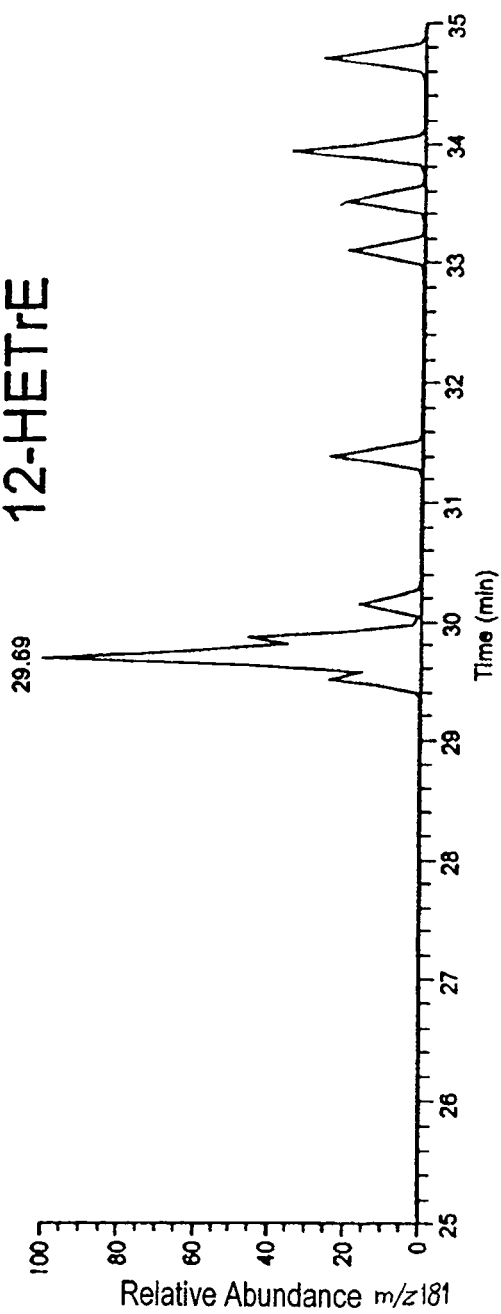
Figure 10A:
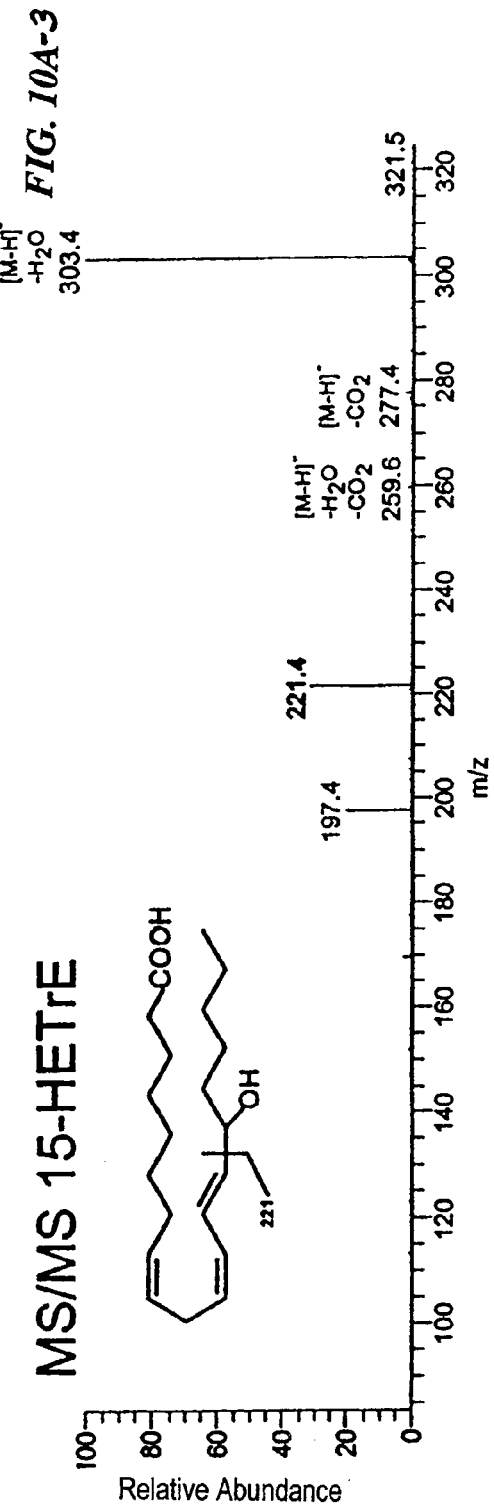
Figure 3:
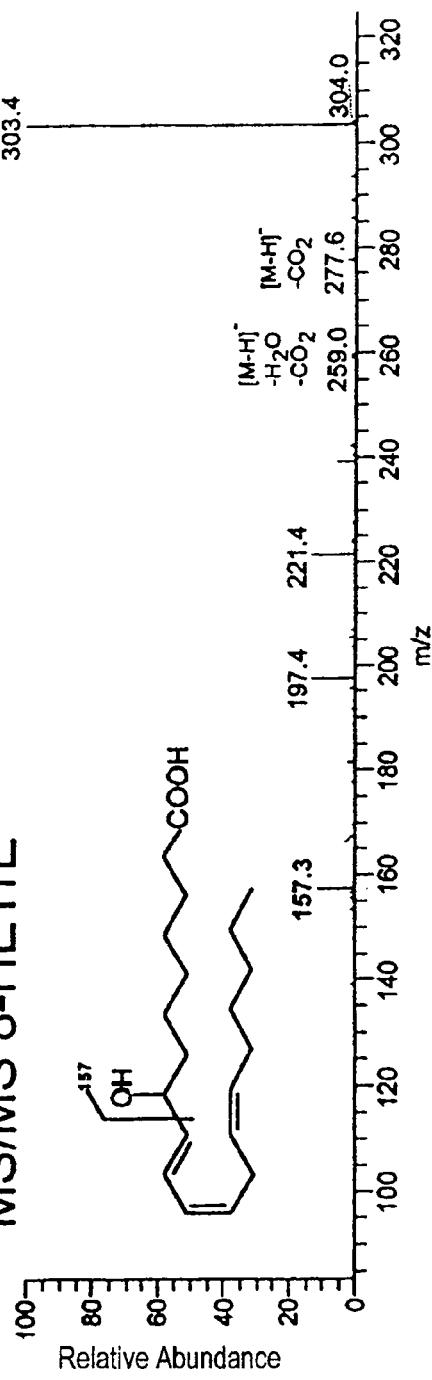
Figure 10A:
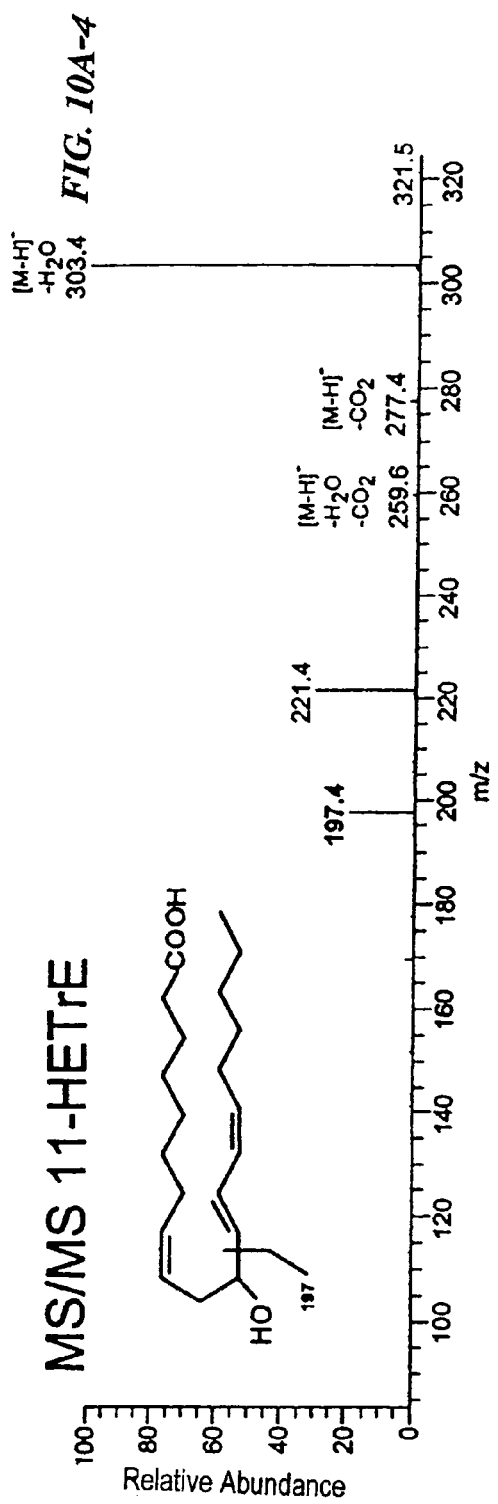
Figure 4:
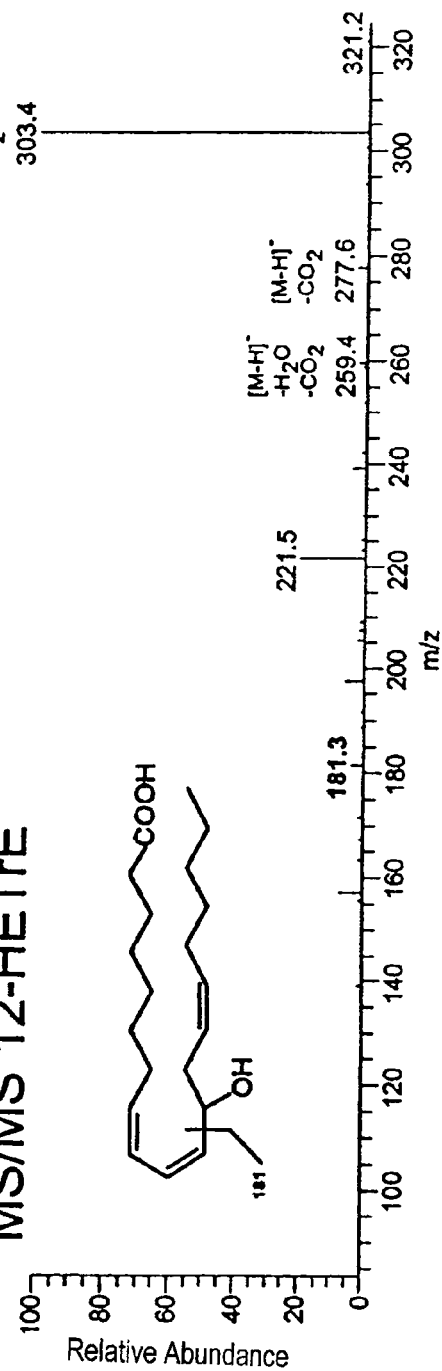
Figure 10B:
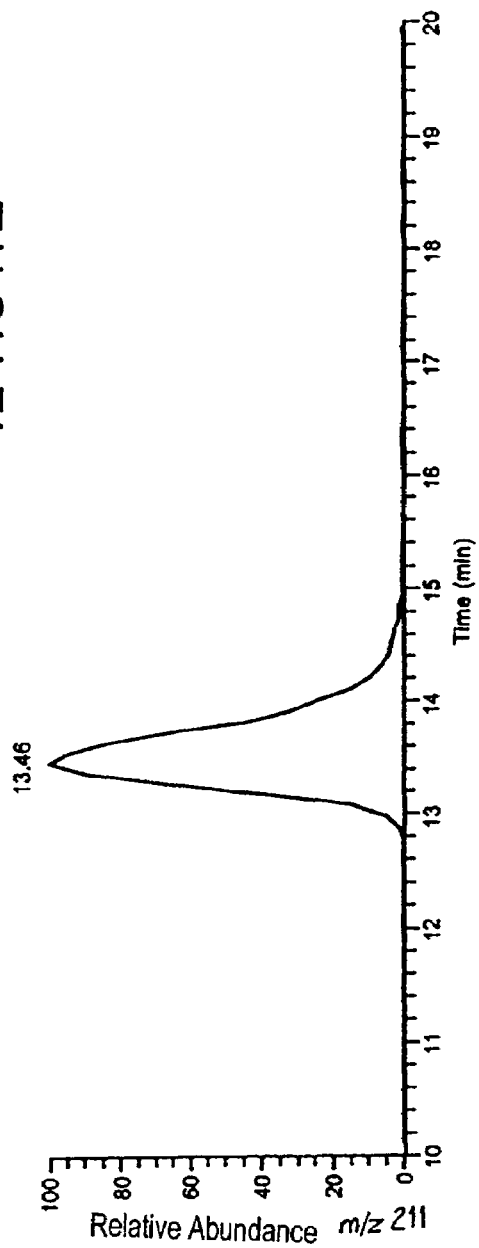
Figure 1:
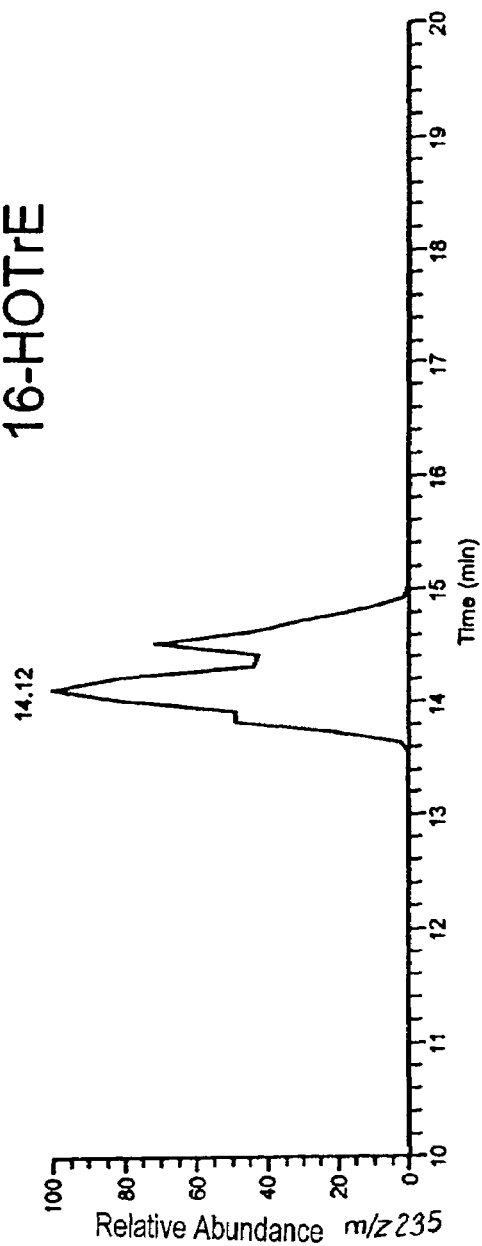
Figure 10B:
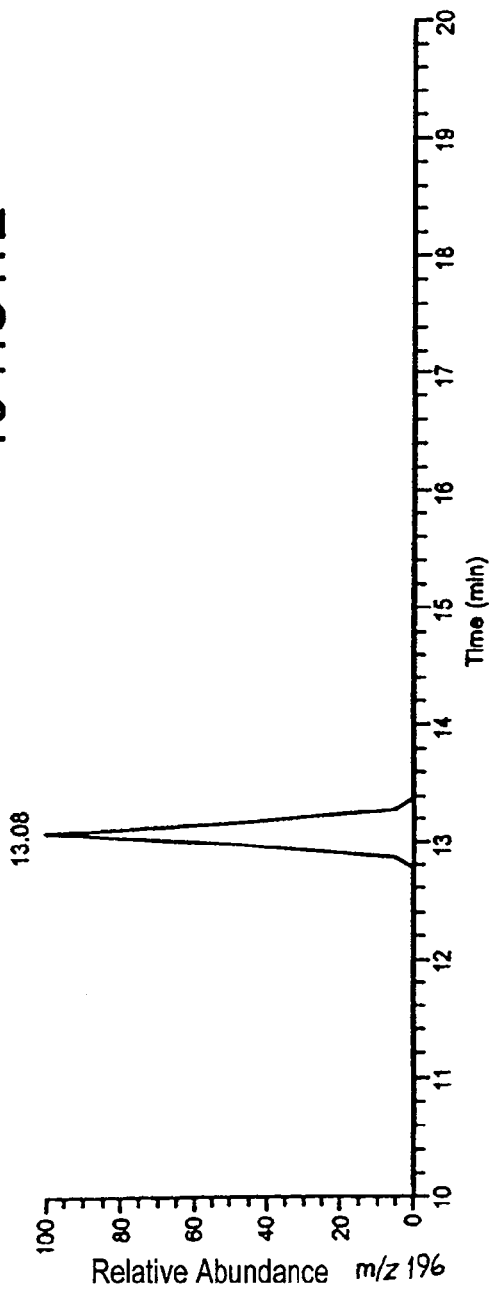
Figure 2:
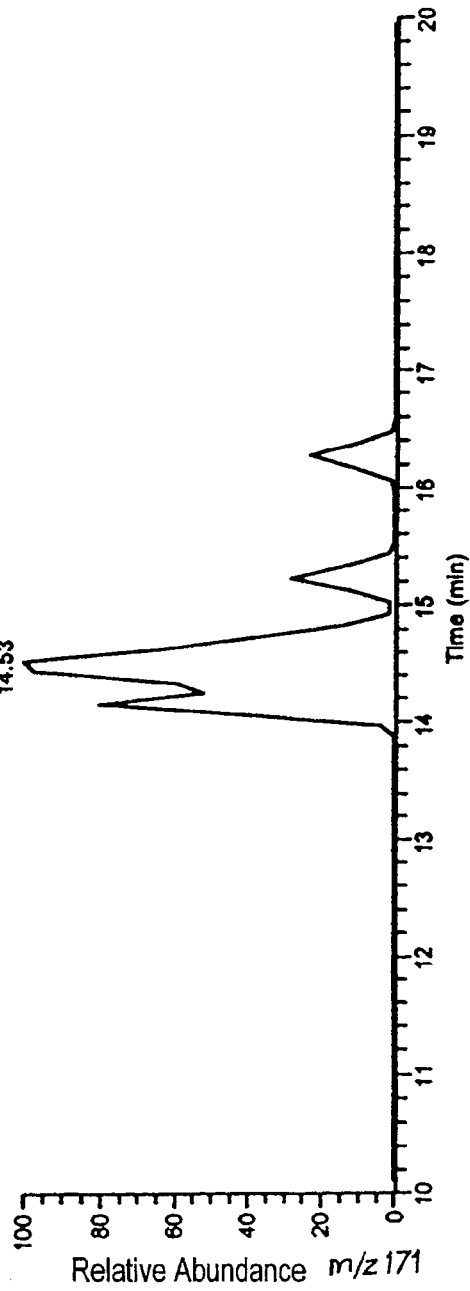
Figure 10B:
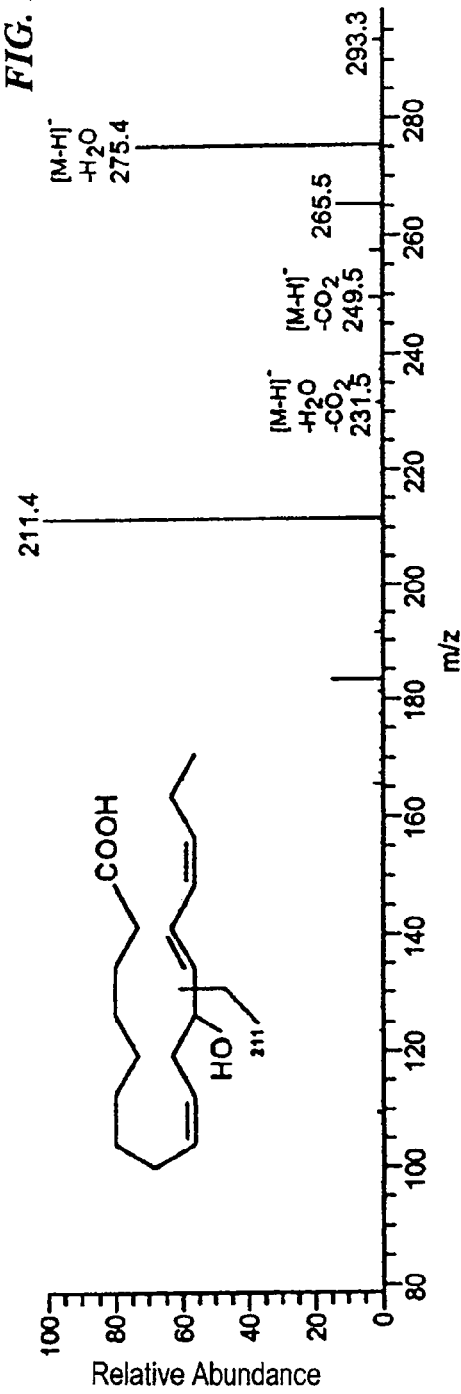
Figure 3:
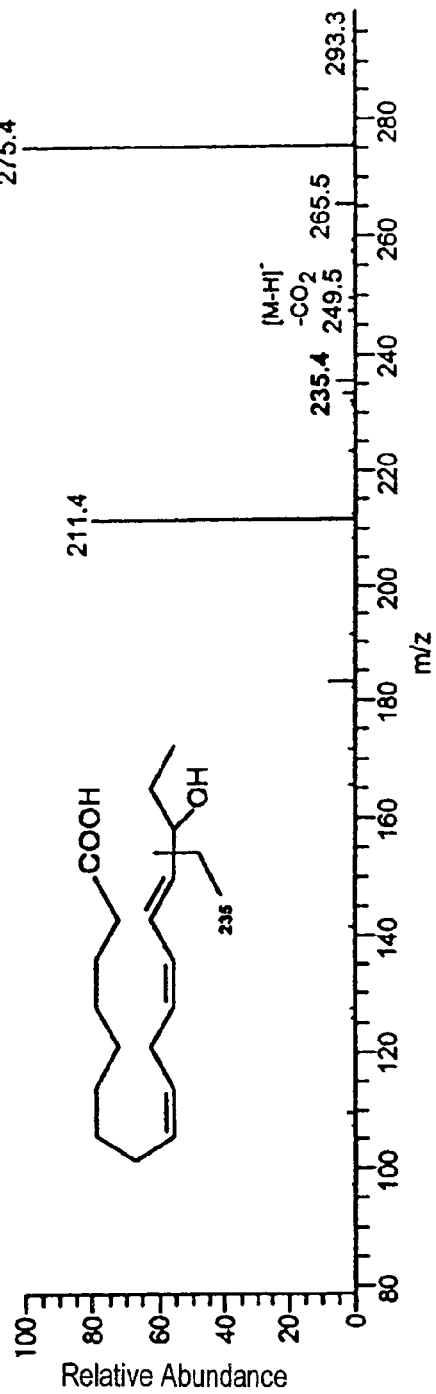
Figure 10B:
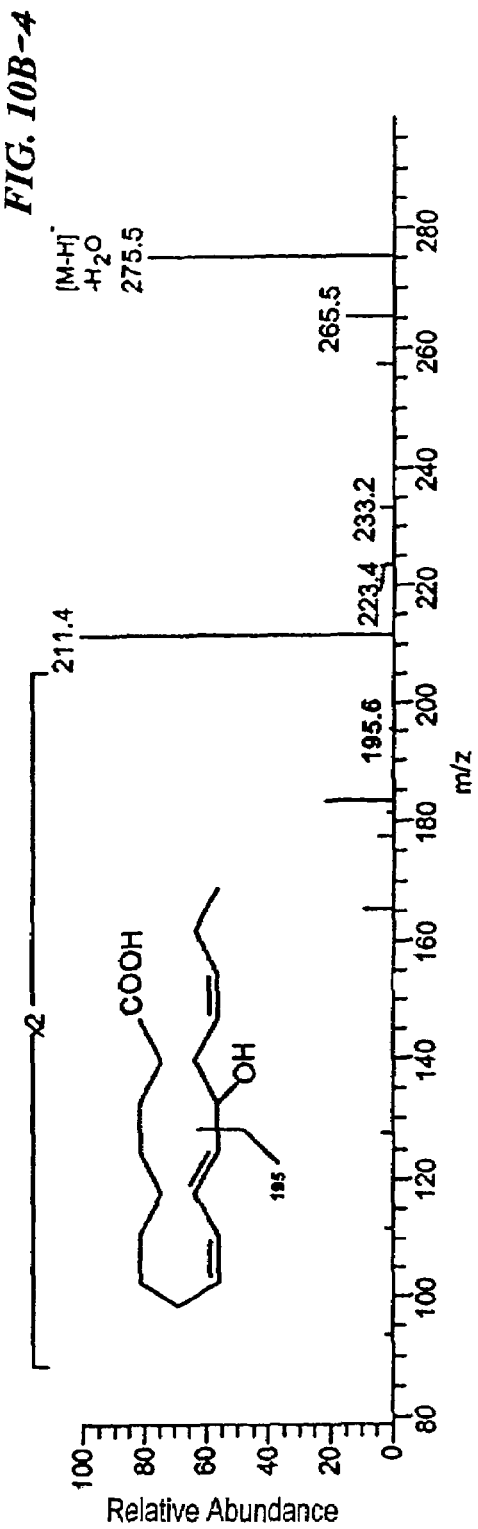
Figure 4:
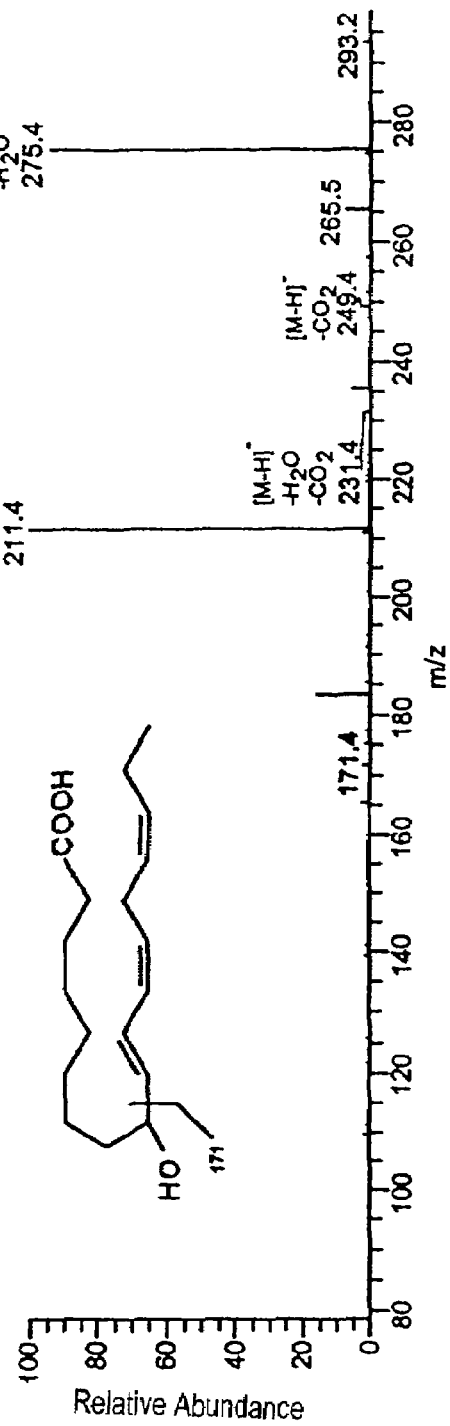
Figures 1, 10C:
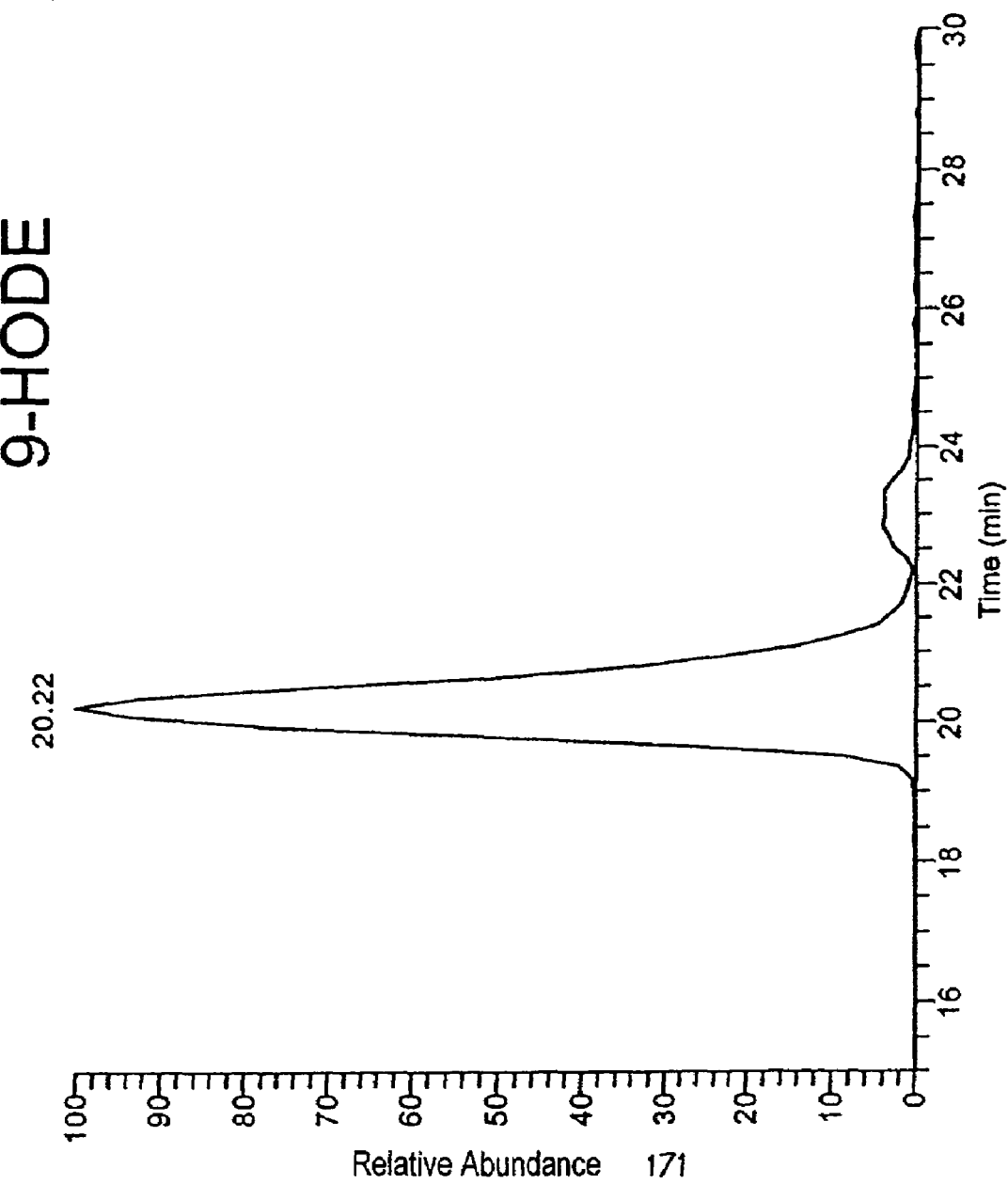
Figures 2, 10C:
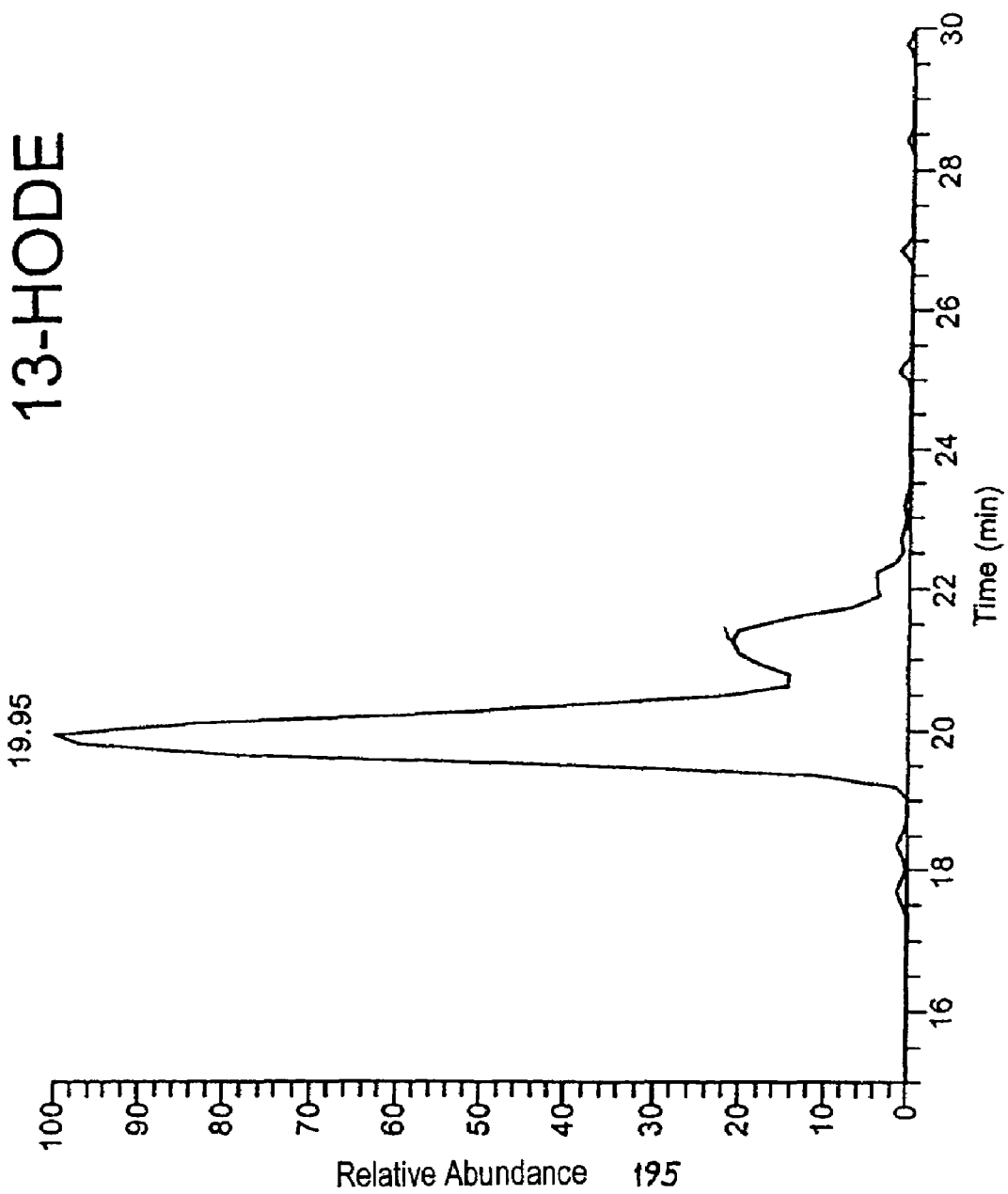
Figures 3, 10C:
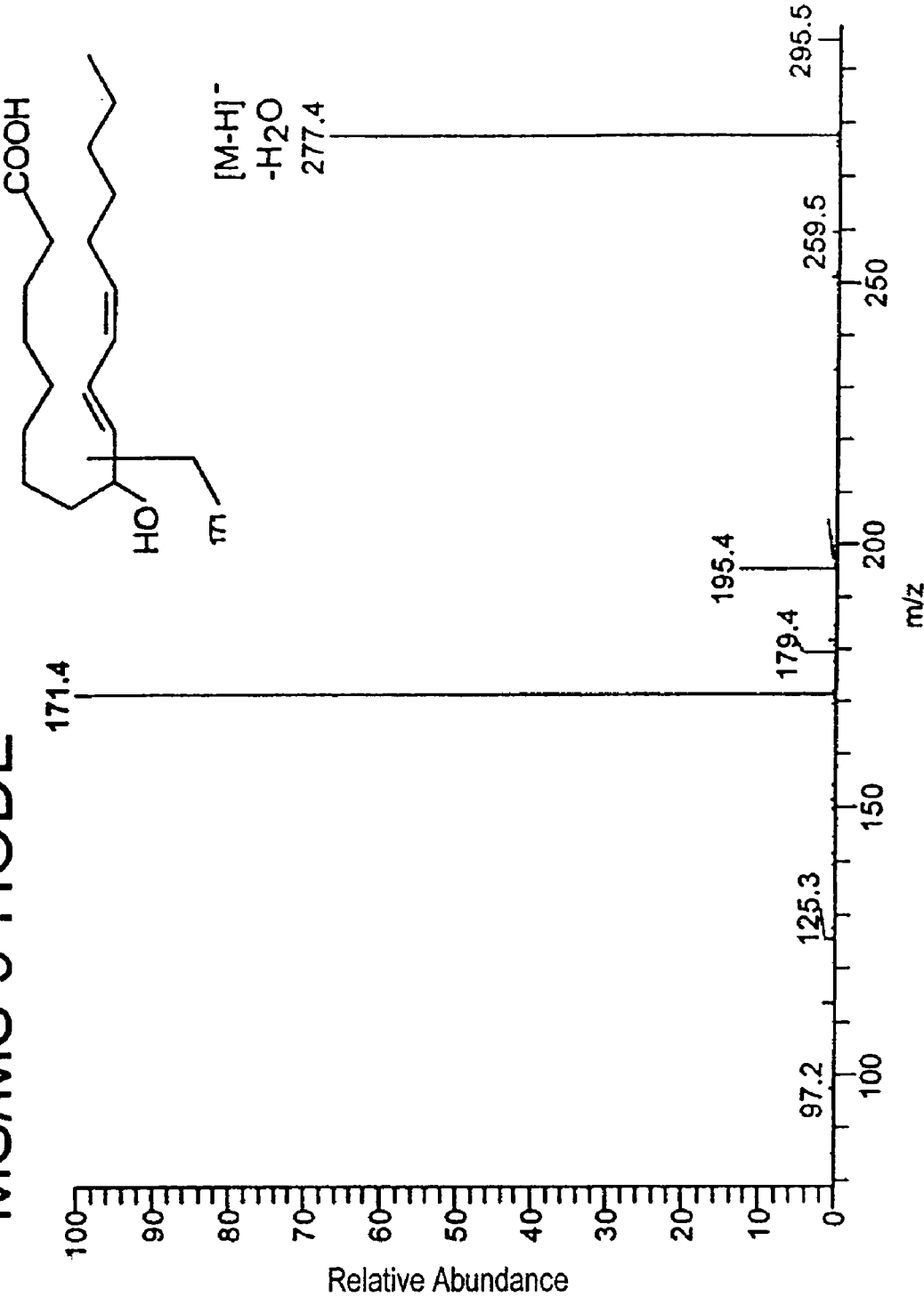
Figures 4, 10C:
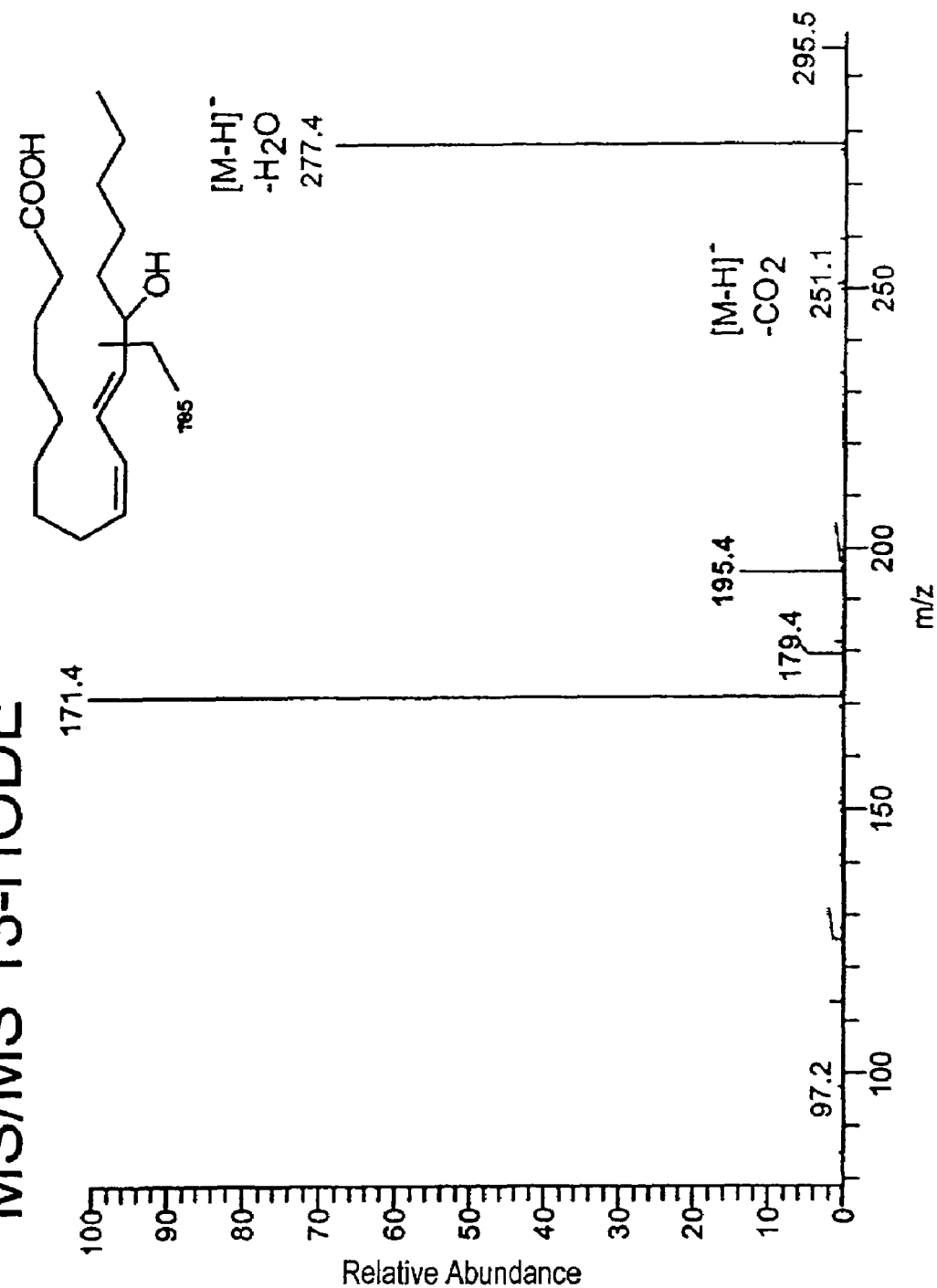

Transendothielial migration is a pivotal event in PMN recruitment and inflammation and a recognized locus of action for traditional antiinflammatory therapies (27. Cronstein, B. N., S. C. Kimmel, R. I. Levin, F. Martiniuk, and G. Weissmann. 1992. A mechanism for the antiinflammatory effects of corticosteroids: The glucocorticoid receptor regulates leukocyte adhesion to endothelial cells and expression of endothelial-leukocyte adhesion molecule 1 and intercellular adhesion molecule 1. *Proc. Natl. Acad. Sci. USA* 89:9991-9995). Endogenous lipid mediators that can control these cell-cell interactions are of interest. Therefore, 5,12,18R-triHEPE and in precursor 18R-HEPE on human PMN transmigration were evaluated and assessed. Both compounds inhibited LTB$_4$-stimulated PMN transendothelial migration (FIG. 9A) with an apparent IC$_{50}$ for 5-50 nM for 5,12,18R-triHEPE and IC$_{50}$>1.0 µM for 18R-HEPE. Thus, the new 5-series members, namely, 18R-carrying trihydroxy-HEPE and 18R-HEPE, inhibited PMN migration, as did 15-epi-LXA$_4$, and in omega and analogue, tested in parallel for direct comparison (FIGS. 10A-10L, Table 1 and Table 2). Their rank order of potency was 15-epi-LXA$_4$ stable analogue >5,12,18R-triHEPE >18R-HEPE.

The G protein-coupled receptor for LTB$_4$ was identified (28. Yokomizo, T., T. Izumi, K. Chang, T. Takuwa, and T. Shimizu. 1997. A G-protein-coupled receptor for leukotriene B4 that mediates chemotaxis. *Nature* 387:620-624.), and to determine whether these 18R-containing products interact with human LTB$_4$ receptors to block PMNs, this receptor was cloned (Reference 11) from reported sequences and stably expressed in HEK293 cells for competition binding experiments (FIGS. 10A-10L). The homoligand LTB$_4$, effectively competed (IC$_{50}$ ~2.5 nM). 18R-HEPE did not, while both LTB$_5$ and 5,12,18R-triHEPE competed (IC$_{50}$ 0.5 µM), giving a trend with LTB$_5$>5,12,18R-triHEPE.

Although the 5,12,18R-triHEPE and a related structure (i.e., LTB$_5$) were substantially less effective than 4-series LTB$_4$, consistent with the reduced PMN activity of LTB$_5$ (Reference 24), their potency for displacing [$^3$H]LTB$_4$ was in the range of currently available synthetic LTB$_4$ receptor antagonists (not shown). These findings suggest that 5,12, 18R-triHEPE serves as a damper for LT-mediated responses in vivo if generated in appropriate quantities within the microenvironment as well as a biotemplate (FIG. 12) for total synthesis of new classes of receptor antagonists.

When administered intravenously into tail at low levels (100 ng), 5,12,18R-triHEPE was a potent inhibitor of PMN infiltration into murine dorsal air pouches (FIGS. 10A-10L), as was a 15-epi-LX stable analogue given at equivalent doses for the purposes of direct comparison. 18R-HEPE also carried some activity in vivo (<5,12,18R-triHEPE), whereas it was far less effective with isolated human PMNs in transendothelial migration and apparently did not interact with recombinant LTB$_4$ receptors at these concentrations.

Figures 1, 11:
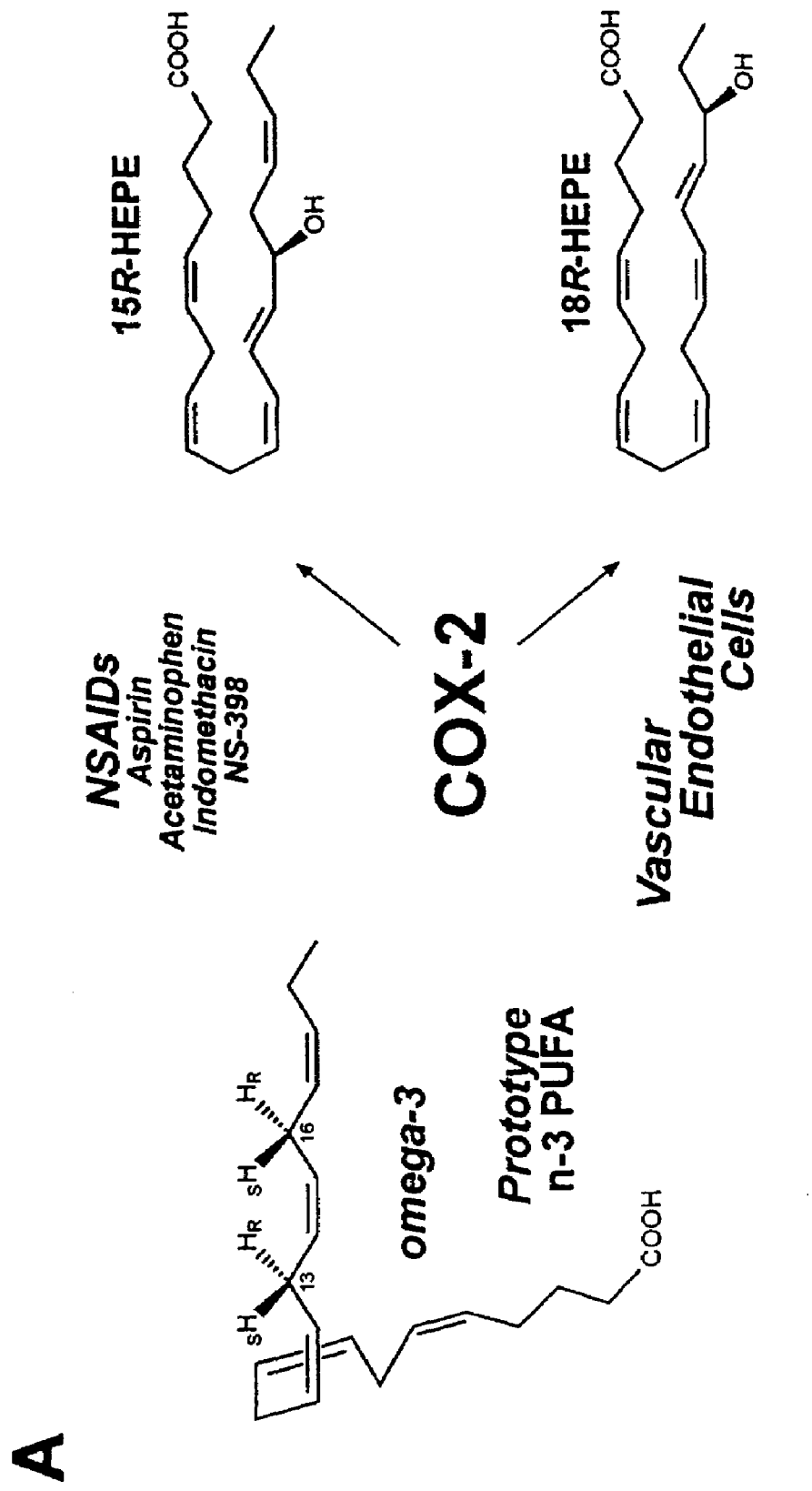
Figures 2, 11:
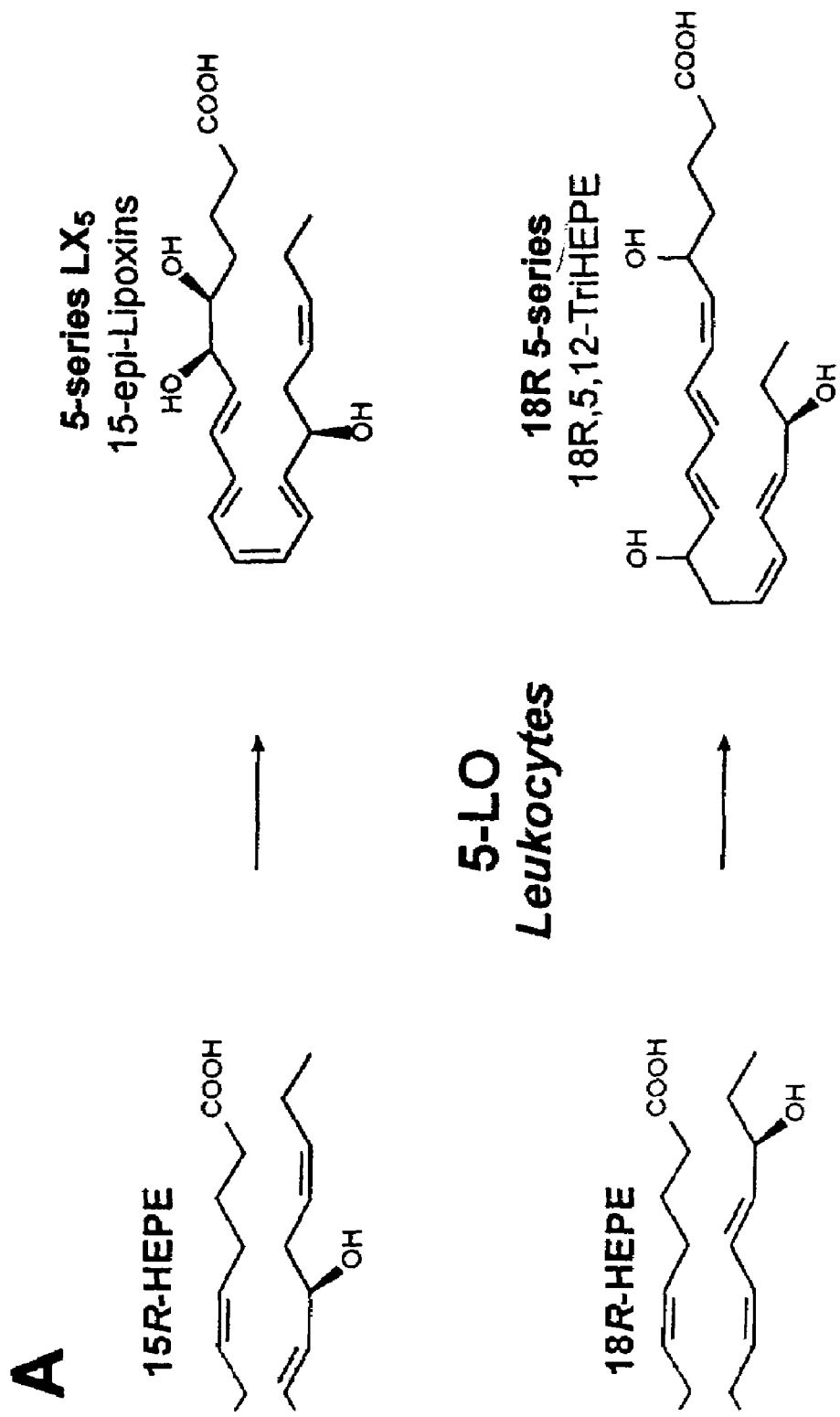
FIG. 11A-11D depict a proposed scheme for Generating Functional Arrays of Lipid Signals from ω-3 PUFA via Transcellular Processing: Endogenous Inhibitors of Microinflammation. At sites where COX-2 is upregulated and treated with NSAIDs, prostaglandin formation from C20:4 is blocked. Systemic ω-3 PUFA are converted via a COX-2-NSAID lipoxygenase-type mechanism that stereospecific hydrogen abstraction at (Panel A) C16 or C13 in EPA (C20:5) to give R insertions of molecular O₂ to yield15R-H(p)EPE or 18R-H (p)EPE from epoxides or are reduced to alcohols or similarly at (Panel B) C13 or C17 in DHA (C22:6) to give insertions of molecular O₂ to yield13-hydroxy-DHA or 17-hydroxy-DHA. The complete stereochemistry of the trihydroxy-compounds remain to be determined and is depicted in their likely configuration. These compounds interact with cells in the local microenvironment, inhibiting PMN recruitment. COX-2-NSAID-dependent hydrogen abstraction and insertion of molecular oxygen occur with all 6-3 PUFA containing 1,4-cis pentadiene units.
Figures 3, 11:
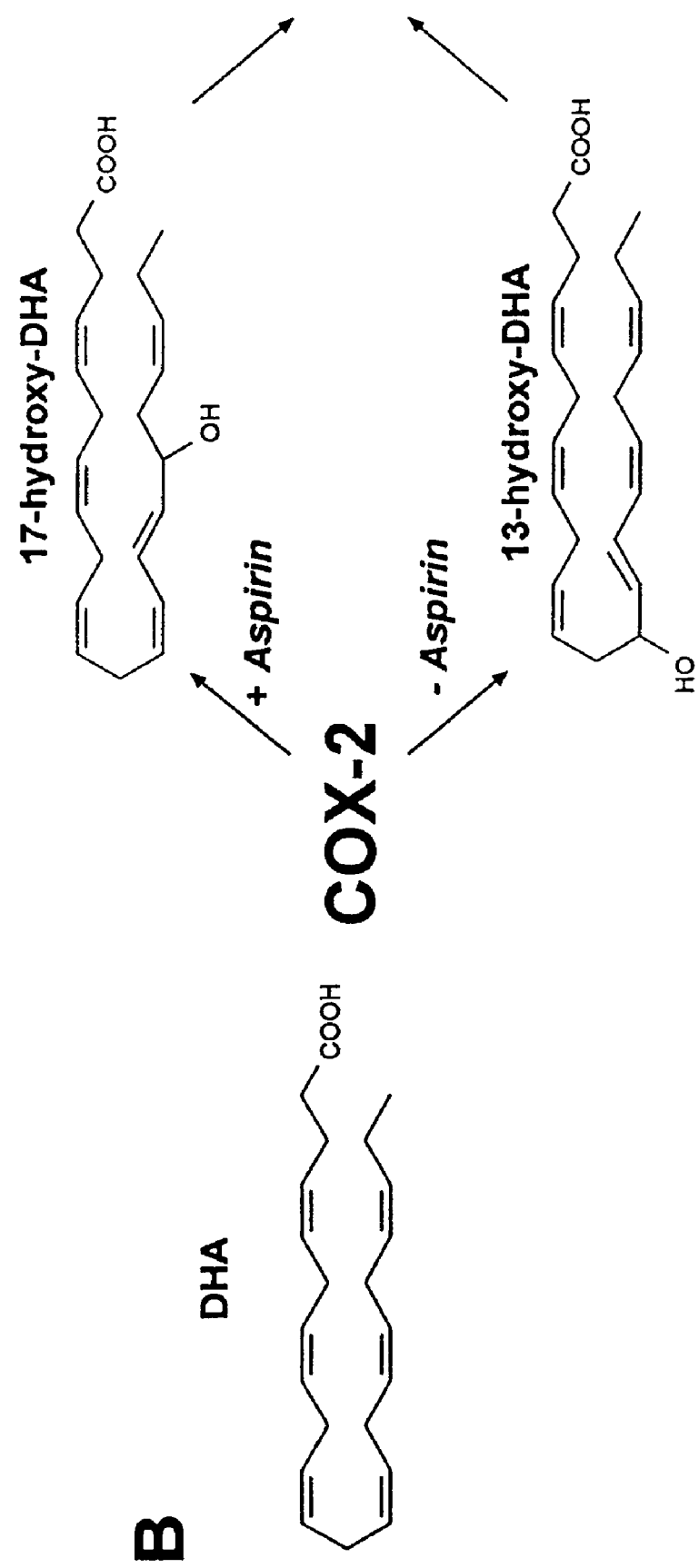
Figures 4, 11:
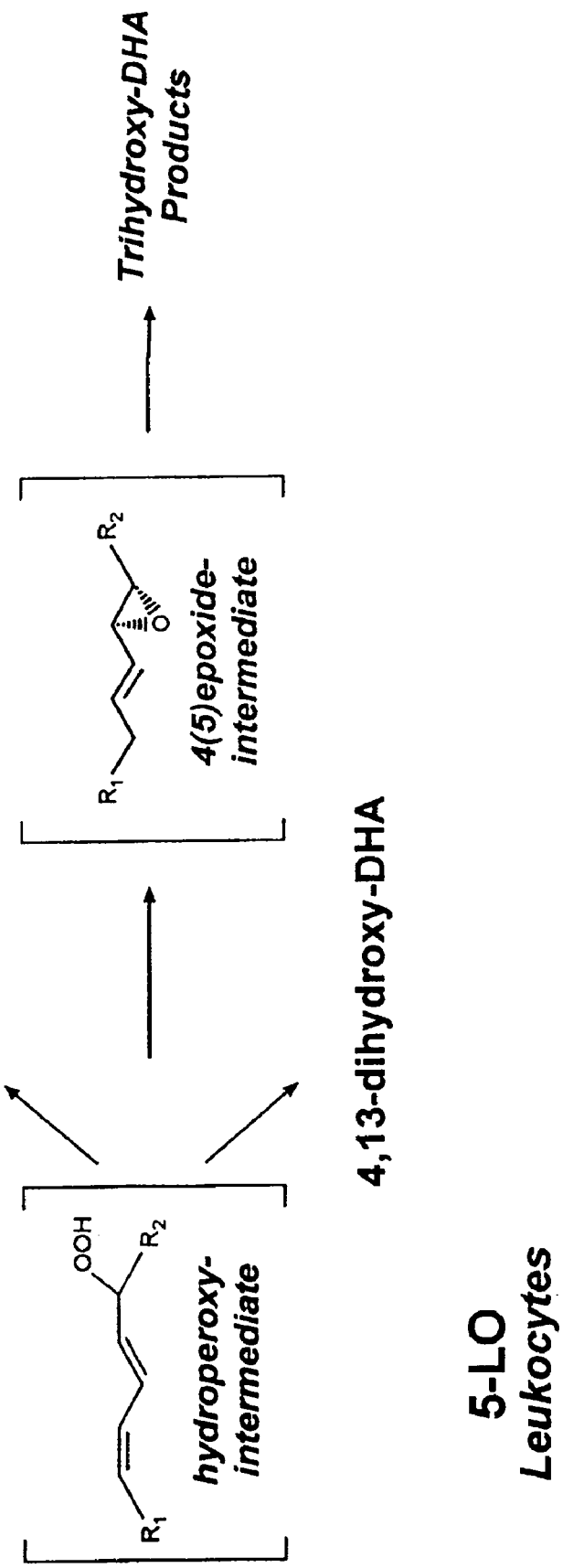

Other widely used NSAIDs (i.e., acetaminophen and indomethacin) were also tested (Table 2) with recombinant COX-2 and C20:5 as in Table 1 to determine whether they altered conversion to HEPE. Each inhibited 11-HEPE by >95%. Interestingly, 18R-HEPE and 15R-HEPE formation persisted (~1:1 ratio) in the presence of either acetaminophen or indomethacin as concentrations as high as 2 mM, even though the levels of 15R- and 18R-HEPE were reduced by three to eight times their levels in the absence of inhibitors (n=3). These findings indicate that the oxygenation of ω3 fatty acids to R-containing monohydro(peroxy)-containing products is not restricted to ASA treatment and arachidonate. Indeed, C18:2, C18:3 and C22:6 were also converted by NSAID-COX-2 complexes to novel reaction products (See FIGS. 11A, B, C and D). Hence, these commonly used NSAIDs and selective COX-2 inhibitors (Table 1 and Table 2) still permit PUFA oxygenation by activated ECs exposed to NSAIDs (FIG. 7) and at sites of inflammation where the degree of COX-2 interactions with drugs to permit the generation of novel oxygenated forms of PUFAs.

Figure 5:
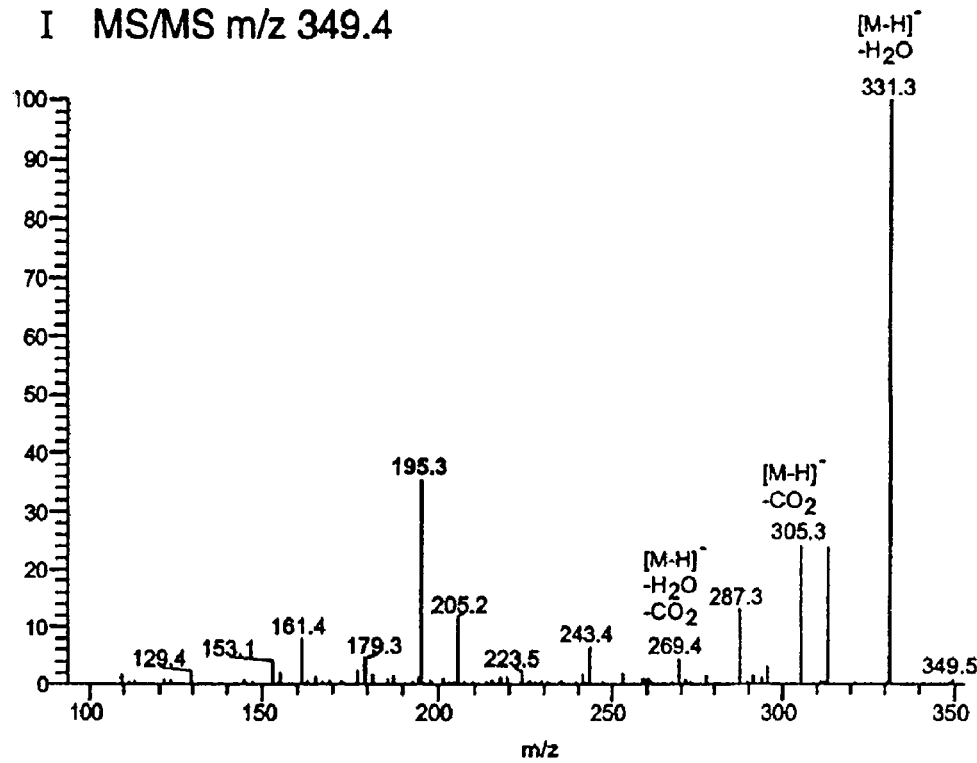
FIG. 5A-5C depict an LC/MS ion chromatogram of 5,12,18-triHEPE isomers generated from 5S,12R-dihydroxy-6Z,8E,14Z,17Z-eicosapentaenoic acid (ω-3) by *B. megaterium* and with mass spectral analyses.
Figure 2:
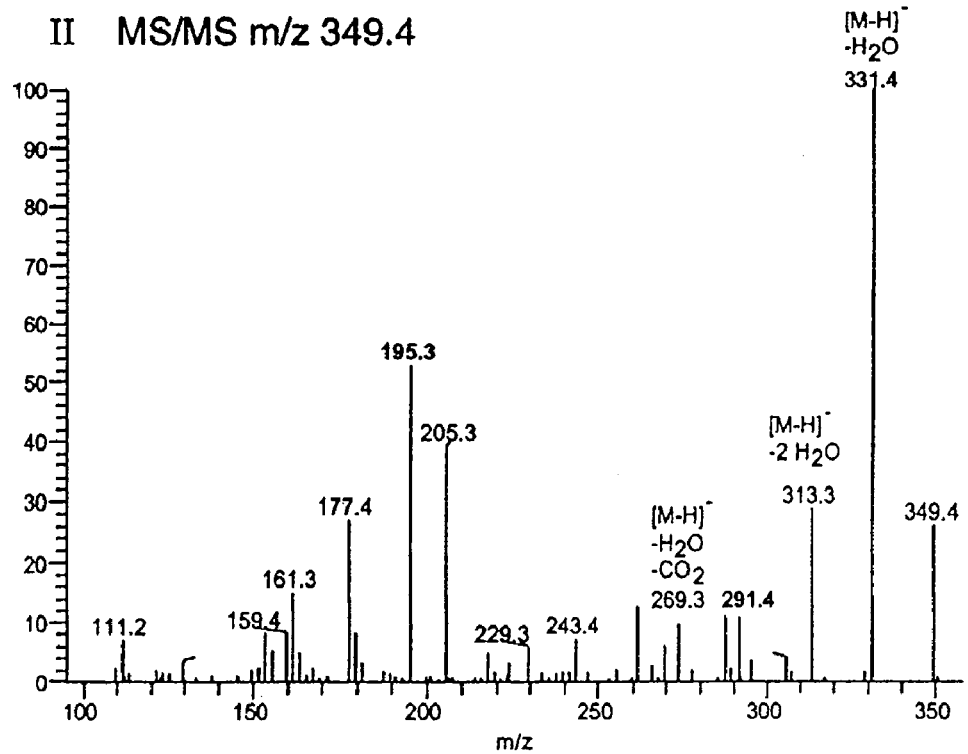

Despite the reports of 6-3 PUFAs (i.e., C20:5) possible beneficial impact in humans (References 1-6), oxygenation by COX-2 to generate novel bioactive compounds that has not been addressed in humans or isolated cells. In fish, both C20:5 and C20:4 are mobilized in macrophages and platelets to produce 5- and 4-series eicosanoids including PG, LT, and LX, with essentially equal abundance (Reference 26). The present invention provides that inflammatory exudates from mice treated with ASA and EPA generate novel compounds (FIG. 4) that are also produced by human ECs, recombinant COX-2, and PMNs (FIGS. 5A-5C). Given the milligram to gram amounts of 6-3 PUFA taken as dietary supplements (References 1-6) and the large area of microvasculature that can carry upregulated COX-2, the conversion of EPA by ECs and neighboring cells as observed in the present experiments (FIGS. 4-8) represent a significant amount at local microenvironments. These COX-2-NSAID-dependent conversions of ω-3 PUFA are likely to be elevated within inflamed or diseased tissues where COX-2 is upregulated and a determinant that impacts fatty acid metabolism when NSAIDs is of therapeutic benefit, namely with microinflammation.

Analogous to 15-epi LX biosynthesis, EPA COX-2-derived 15R-HEPE was converted by 5-lipoxygenation with 5(6)-epoxied formation in leukocytes to give the 15-epi-LX$_5$ series (FIGS. 11A-11D). The stable analogues of 15-epi-LXA$_4$, modified at their C15 position through position 20 with bulk groups, resist inactivating enzymes and are more potent in vivo, inhibiting PMN traffic as well as formation and actions of key proinflammatory cytokines (References 10 and 16). Hence, 5-series 15-epi-LXs should act in a similar fashion, as they possess a ∇17-18 double bond and thus could function as an ω-3-derived 15-epi-LX analogue.

Figure 12:
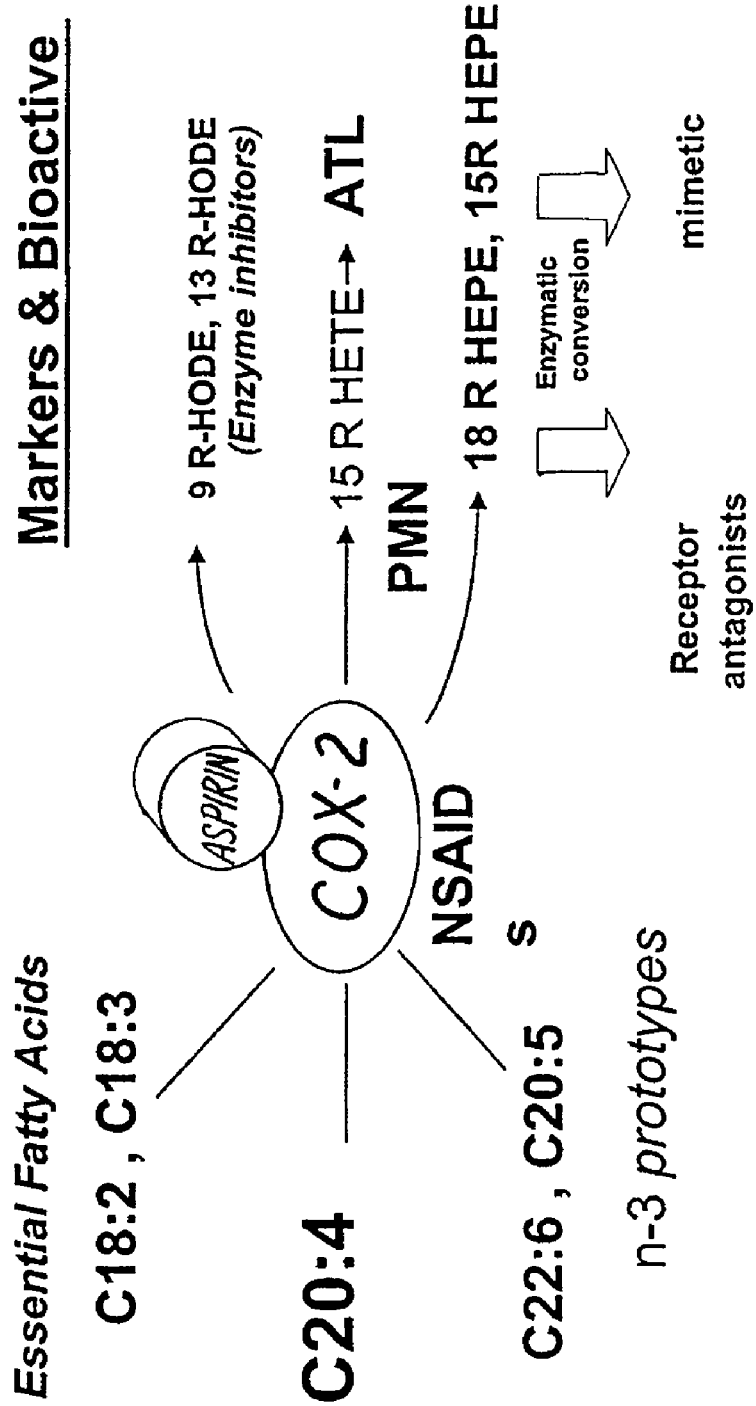
FIG. 12 depicts aspirin acetylated-COX-2 dependent pathways for generating novel lipid mediators that are also markers for aspirin treatment.
Figure 13:
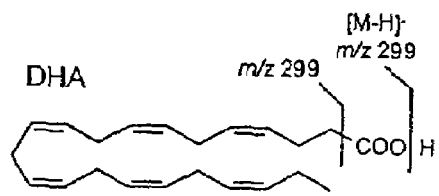
FIG. 13 depicts the structures of the major and minor products generated from docosahexaenoic acid (DHA, C22: 6, ω-3) and aspirin acetylated-COX-2.
Figure 13:
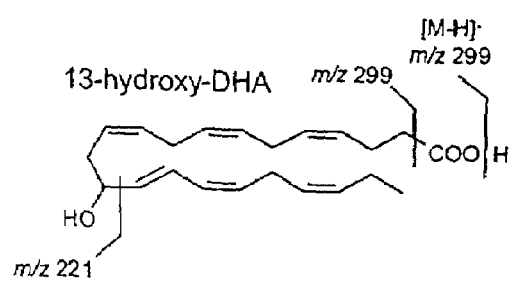
Figure 13:
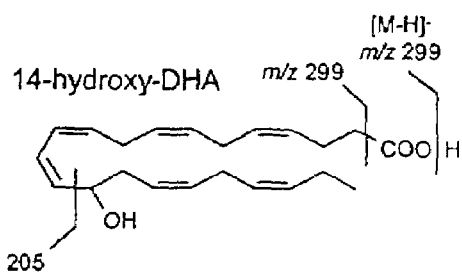
Figure 13:
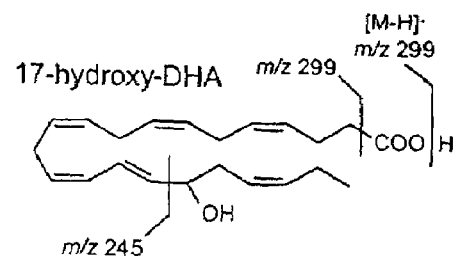
Figure 13:
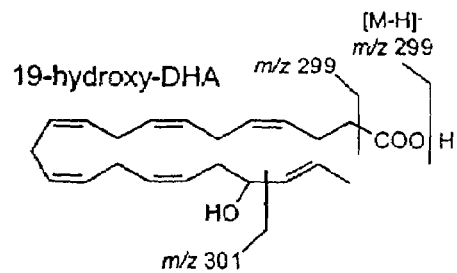
Figure 13:
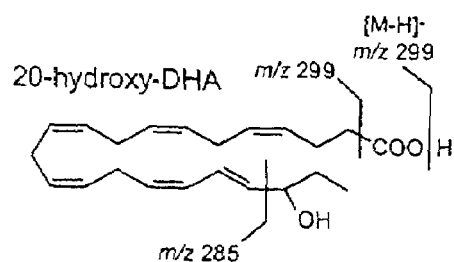
Figure 13:
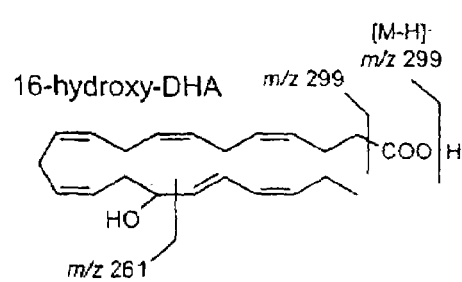
Figures 1, 14A:
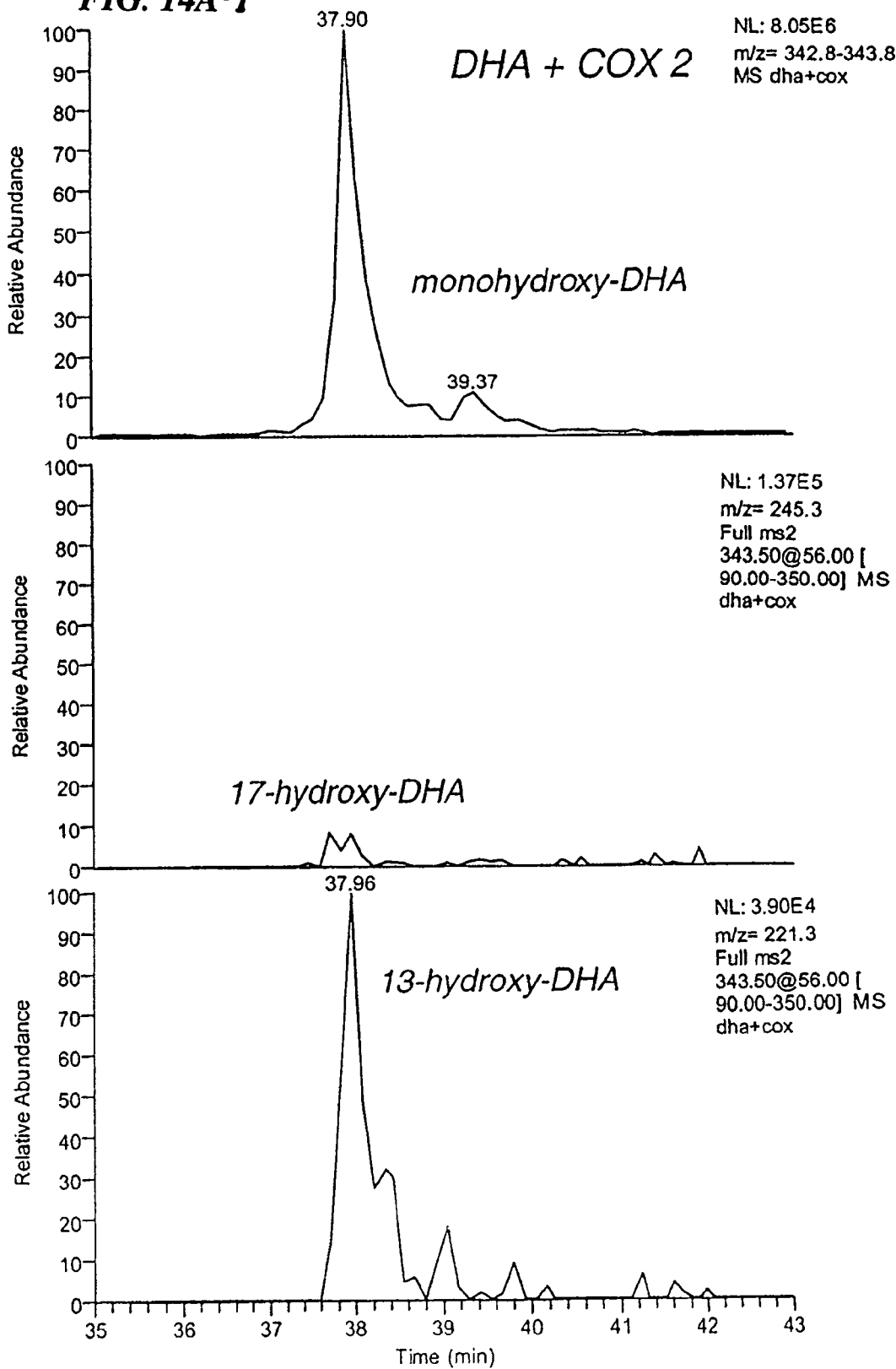
FIG. 14A-14B depict the DHA product profile switch triggered via acetylation of COX-2 by aspirin. The LC/MS ion chromatograms in the left panels show that, in the absence of aspirin, 13-hydroxy-DHA is the dominant product. With acetylation of COX-2 by aspirin, 13-hydroxy-DHA generation is suppressed and, shown in the right panel, 17-hydroxy-DHA generation is becomes the major product.
Figures 2, 14A:
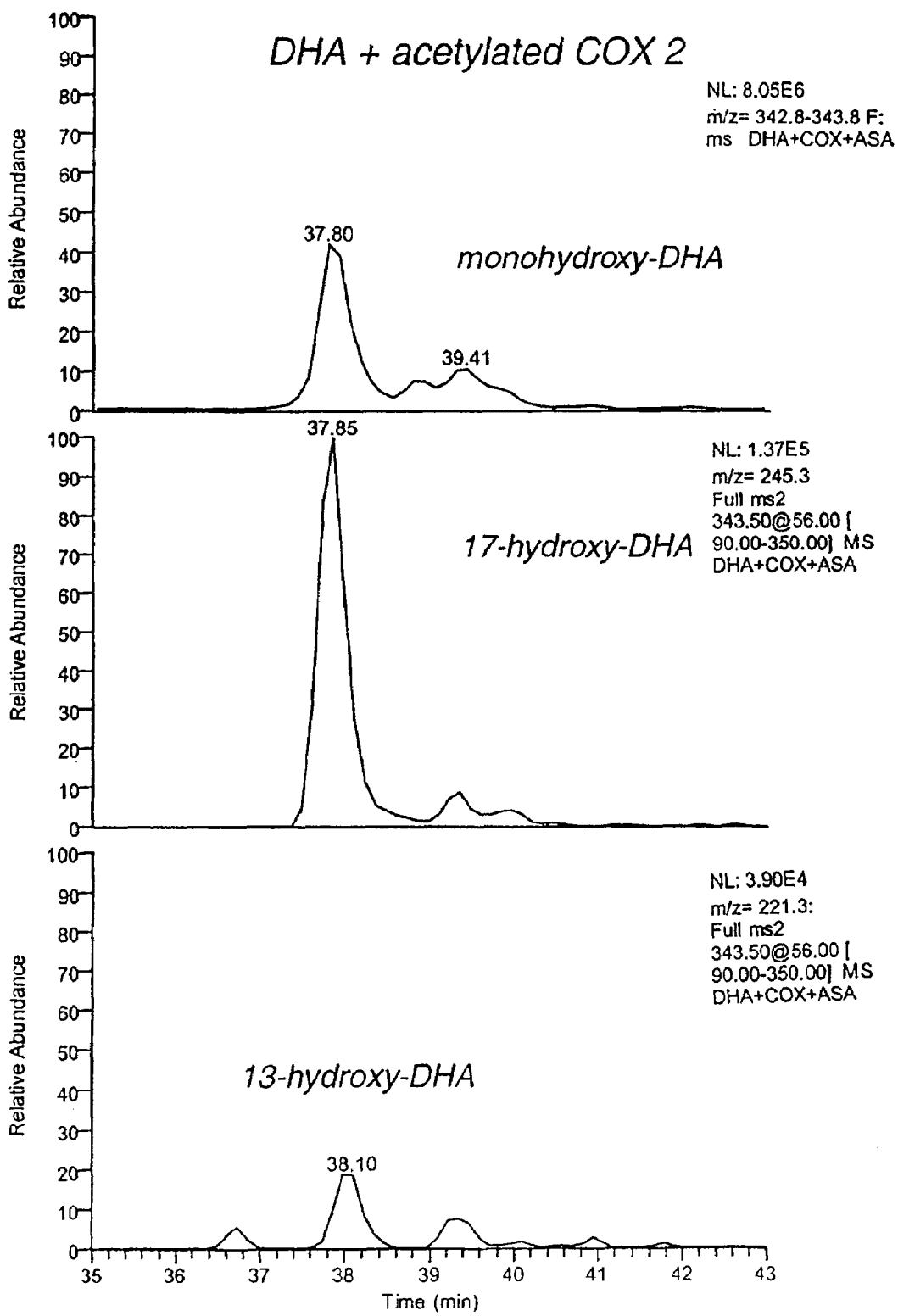
Figures 1, 14B:
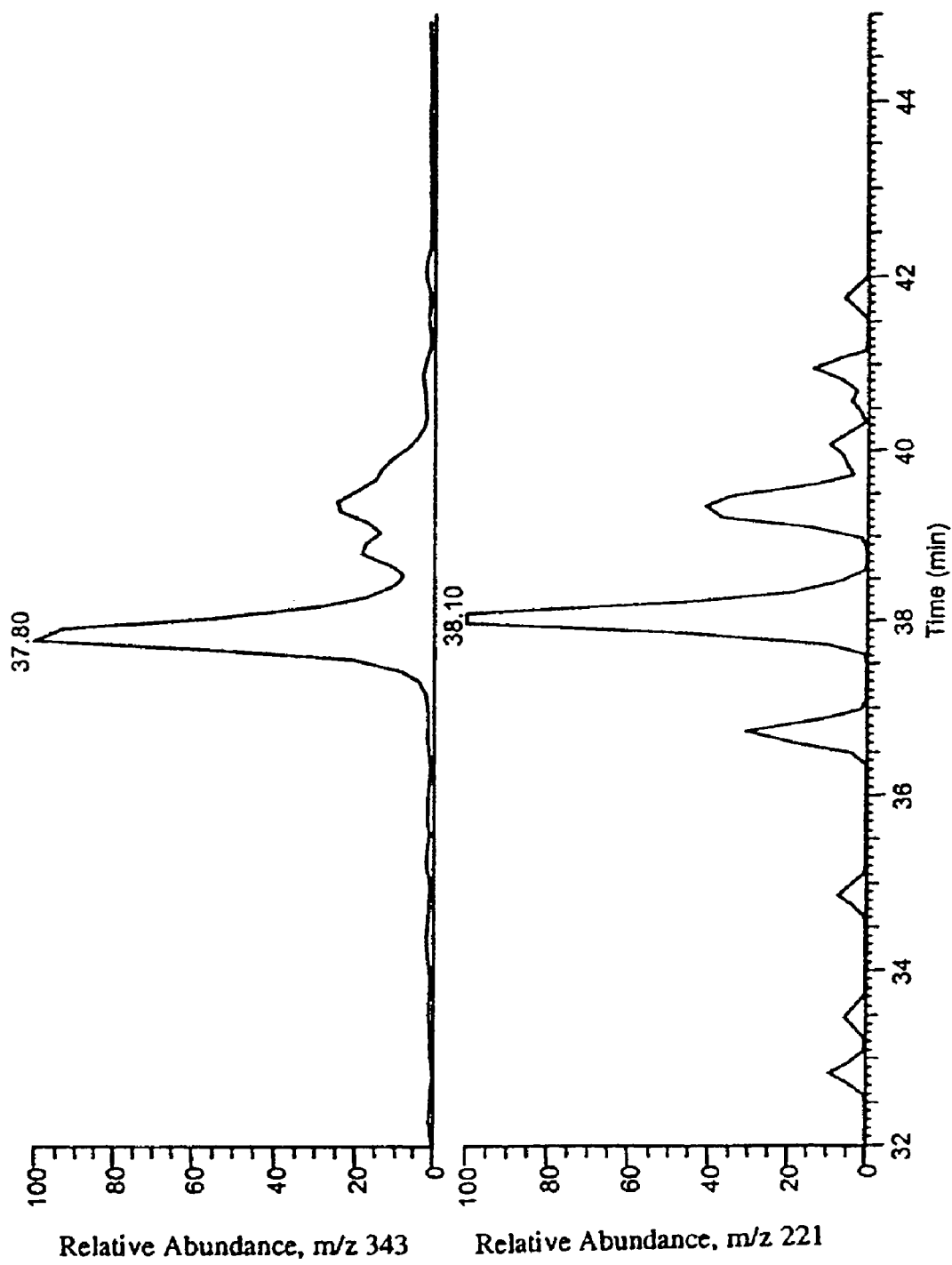
Figures 2, 14B:
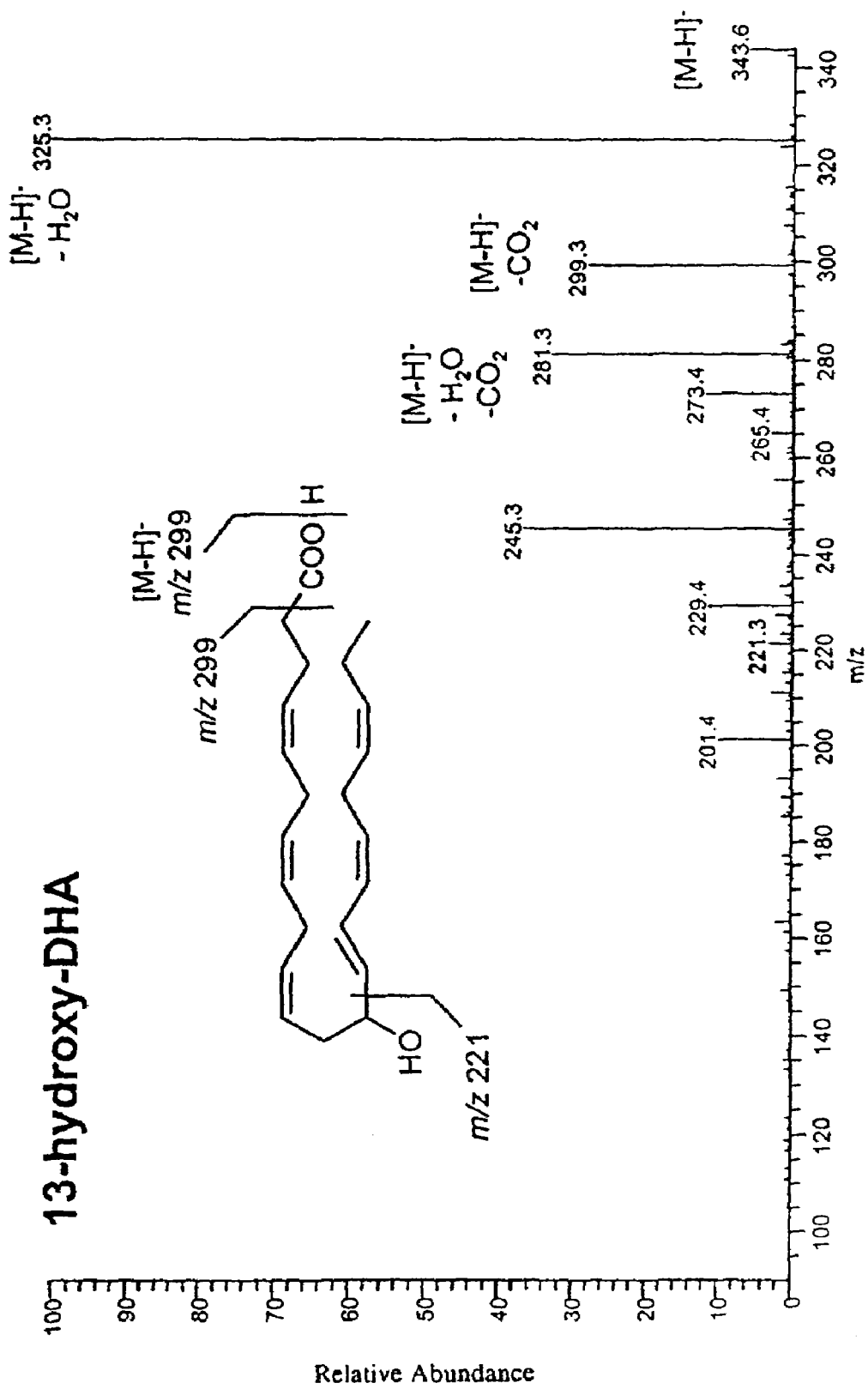
Figures 1, 14C:
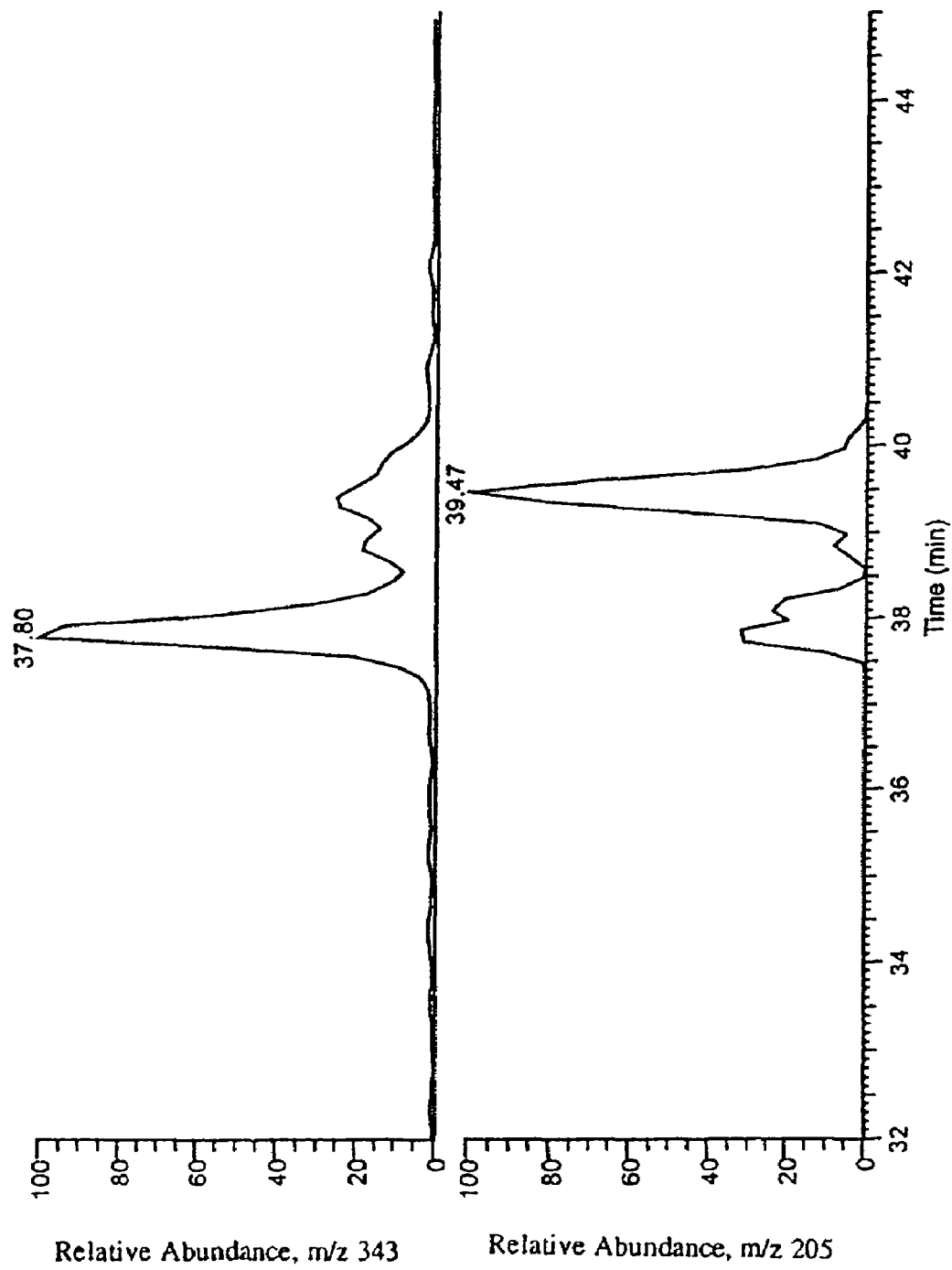
FIG. 14C-14D depict an LC/MS/MS ion chromatogram and mass spectral analysis of 13-hydroxy-DHA generated from DHA by aspirin acetylated-COX-2.
Figures 2, 14C:
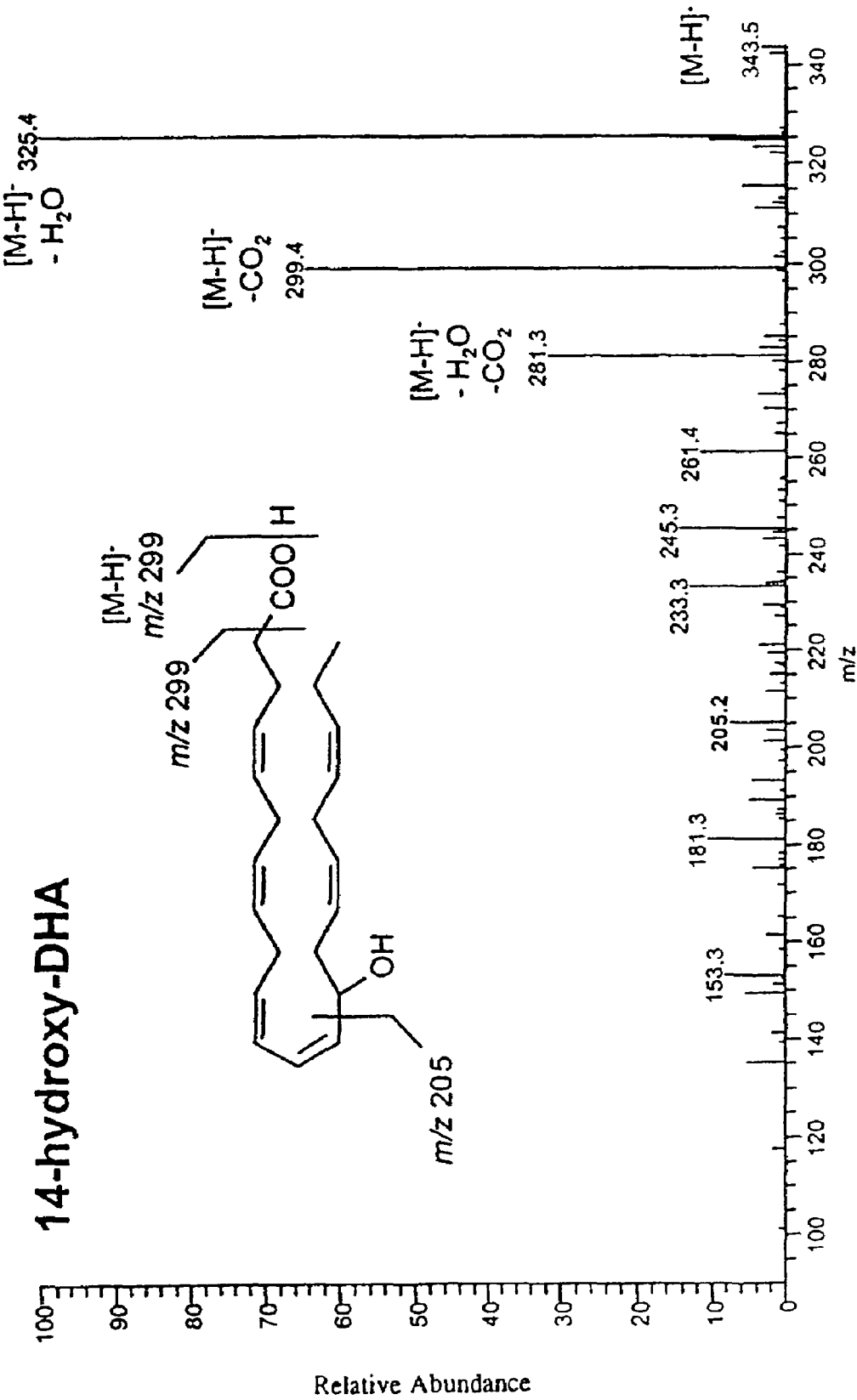
Figures 1, 14D:
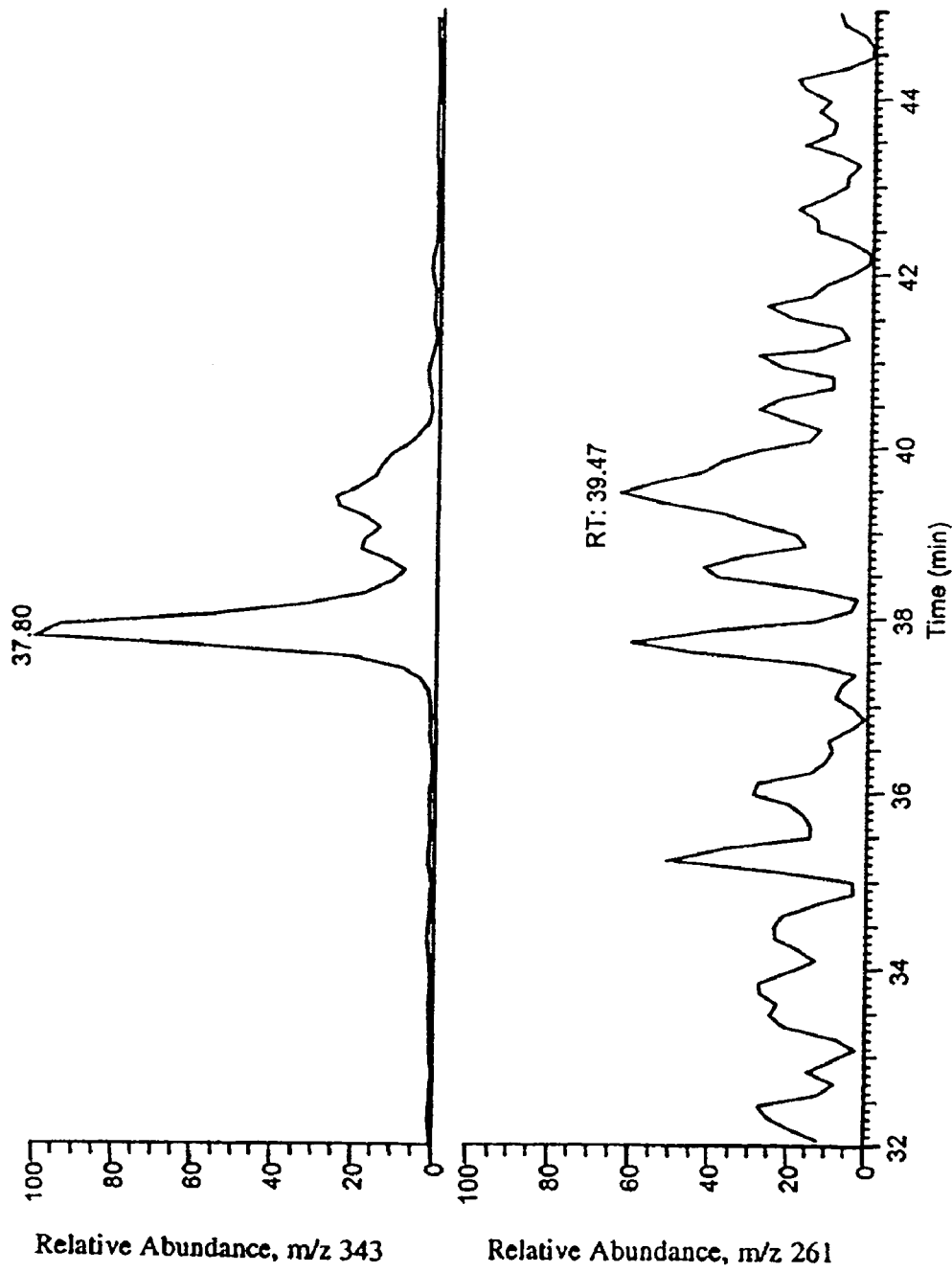
Figures 2, 14D:
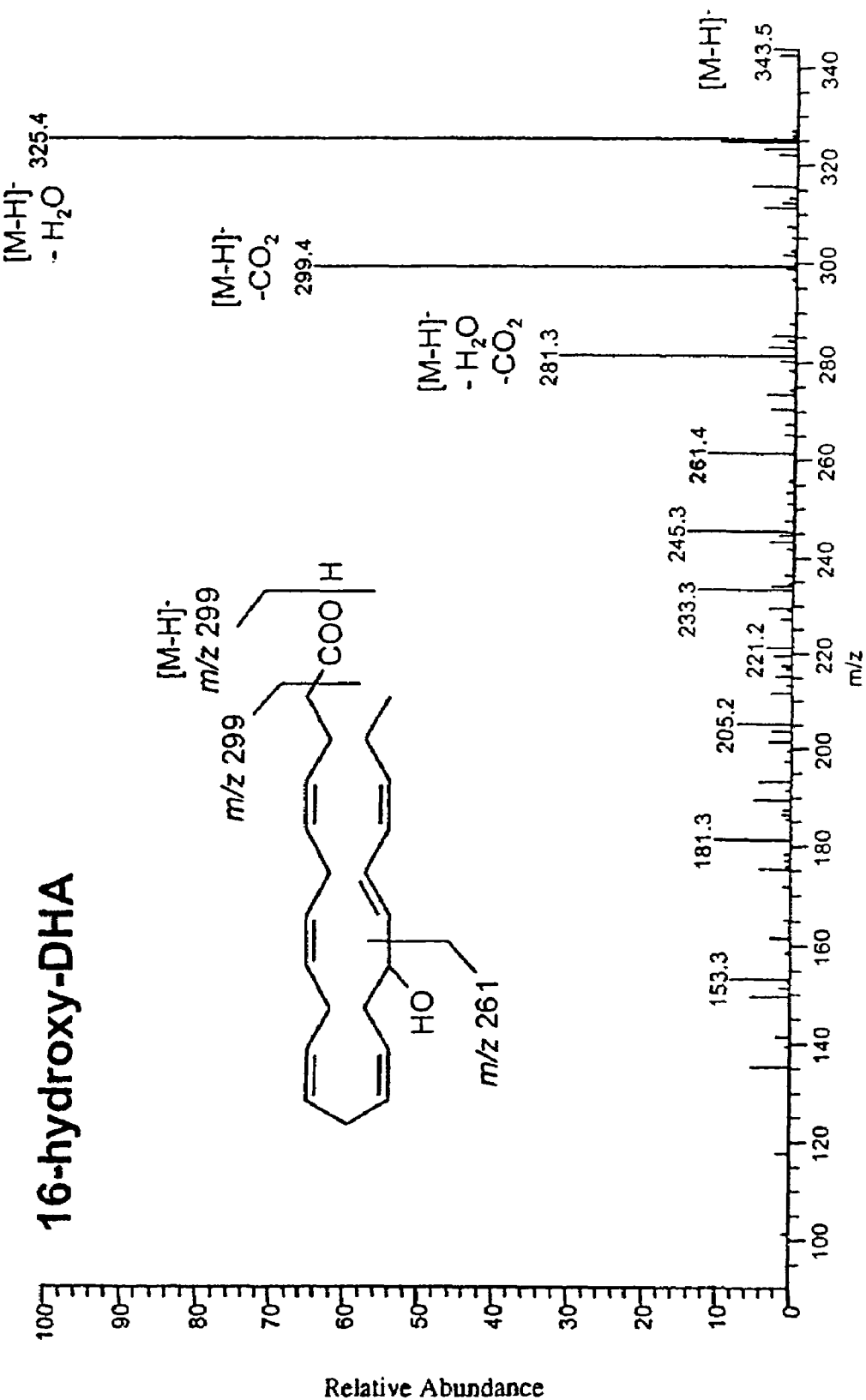
Figures 1, 14E:
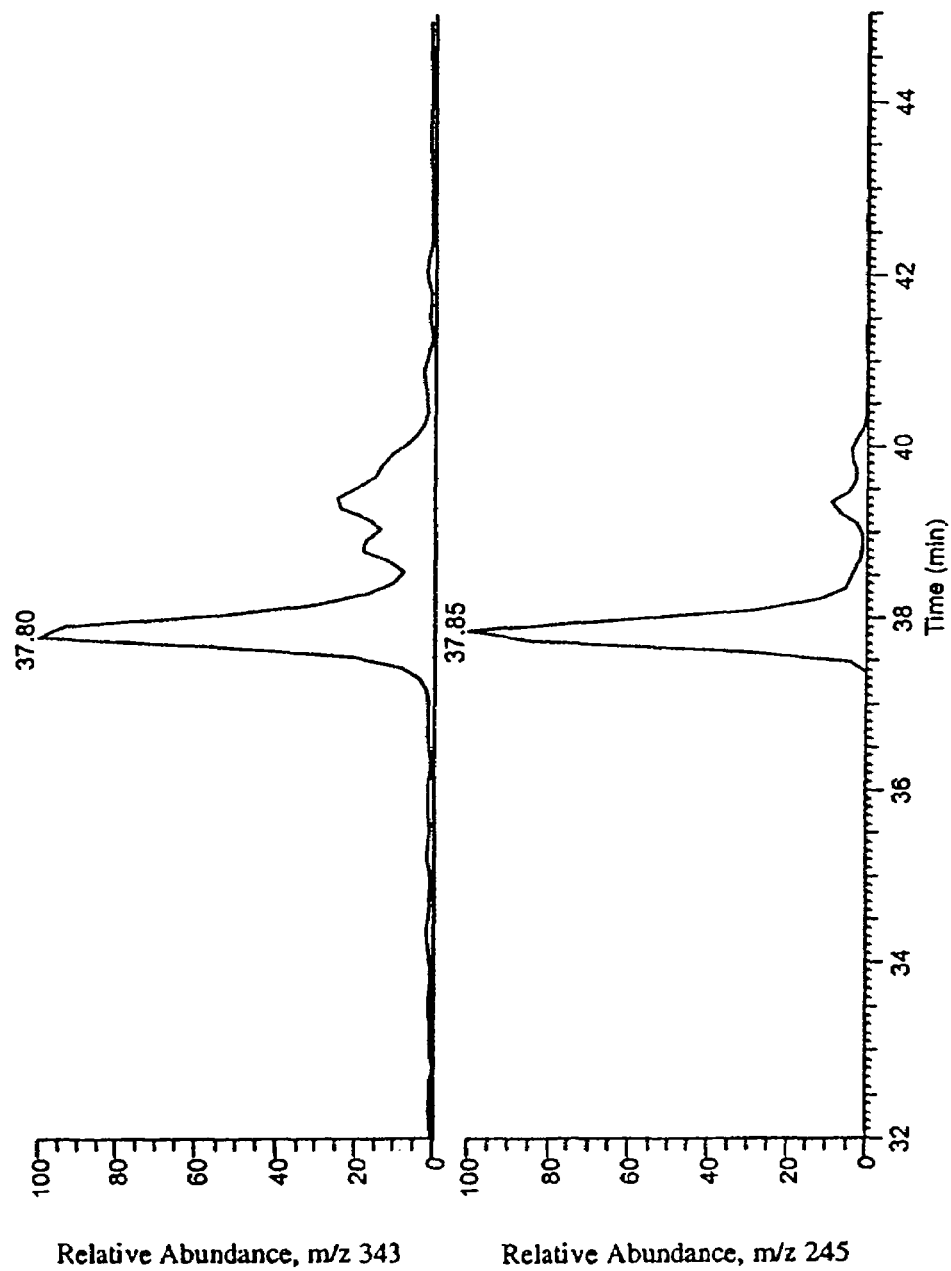
FIG. 14E-14F depict an LC/MS/MS ion chromatogram and mass spectral analysis of 14-hydroxy-DHA generated from DHA by aspirin acetylated-COX-2.
Figures 2, 14E:
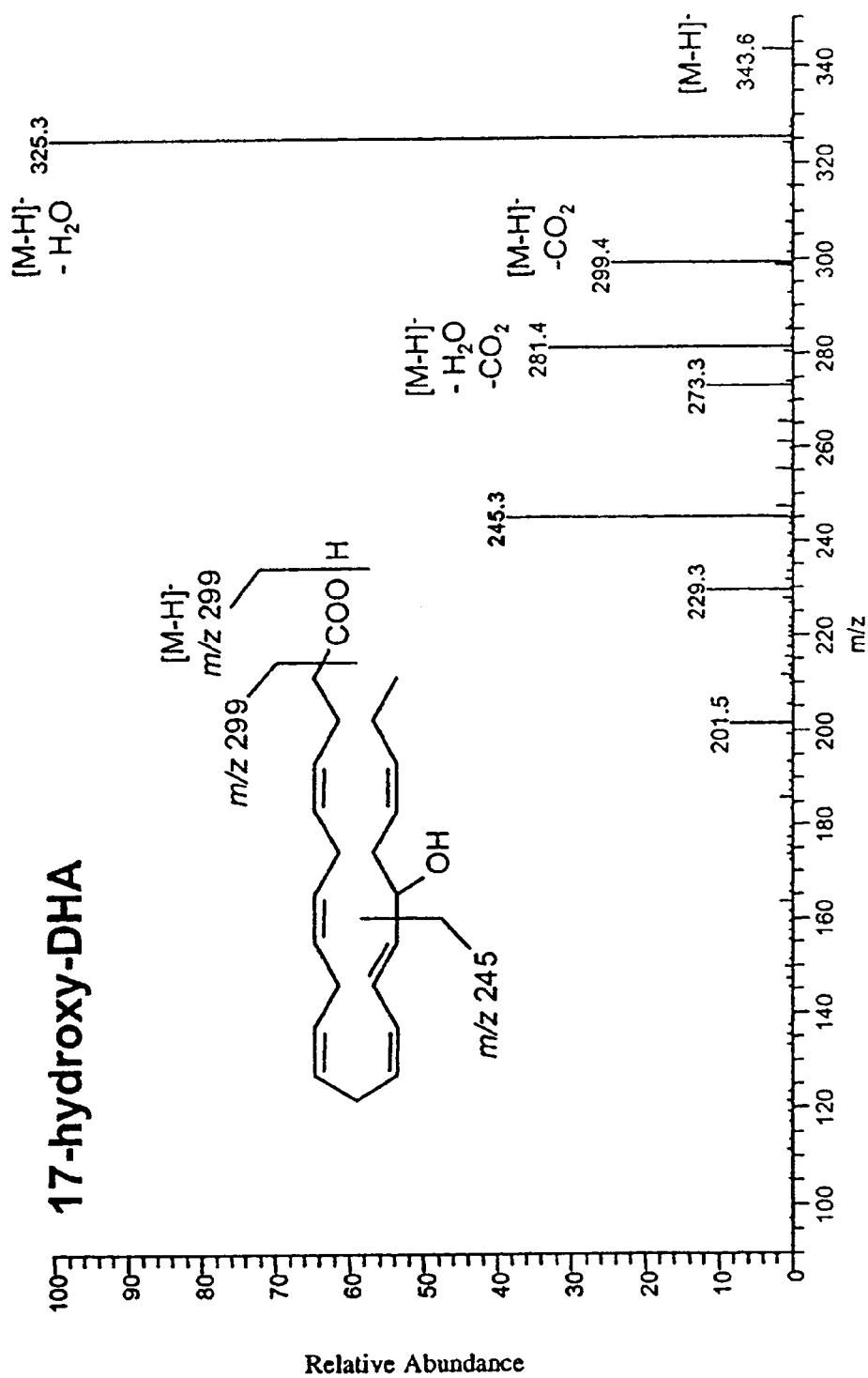
Figures 1, 14F:
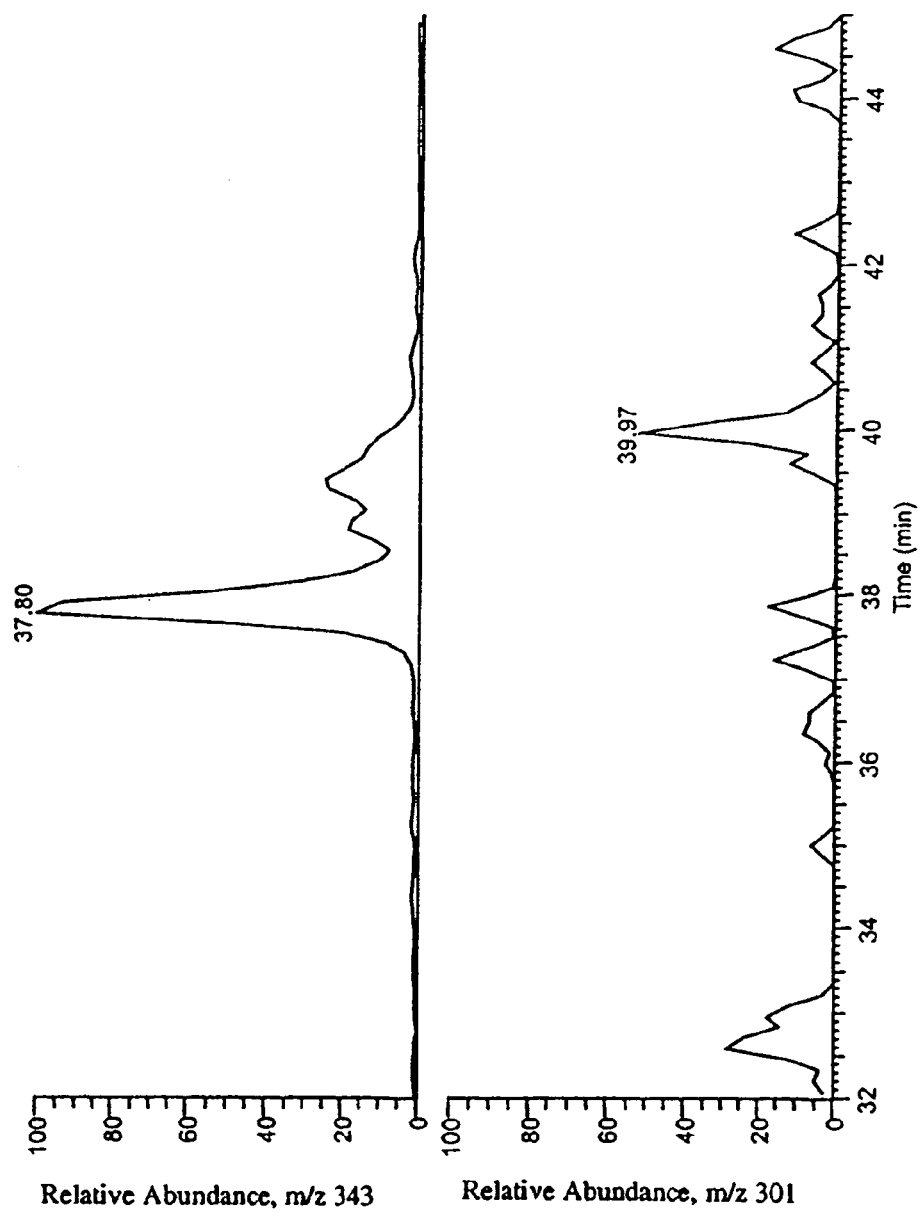
Figures 2, 14F:
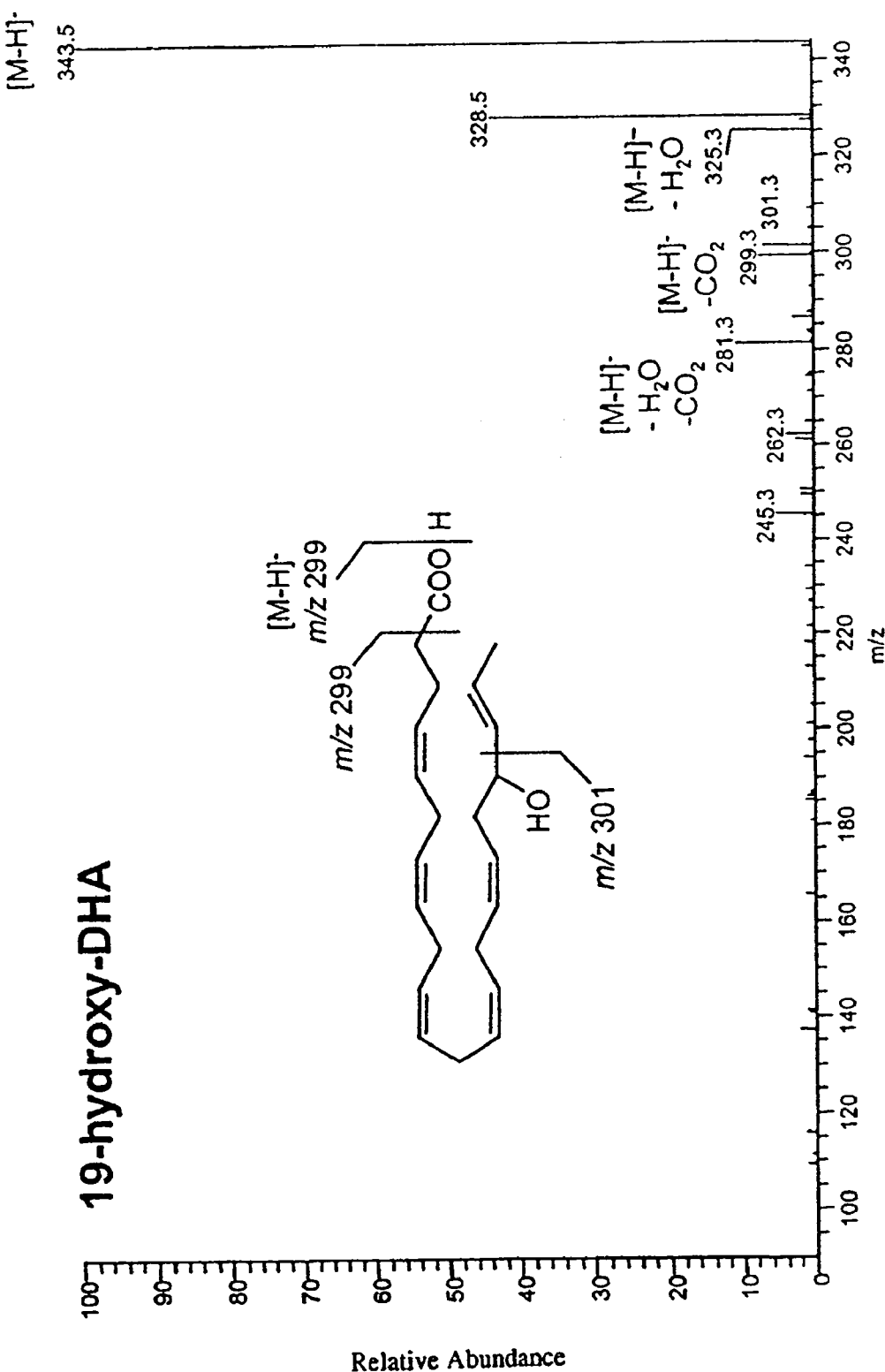
Figures 1, 14G:
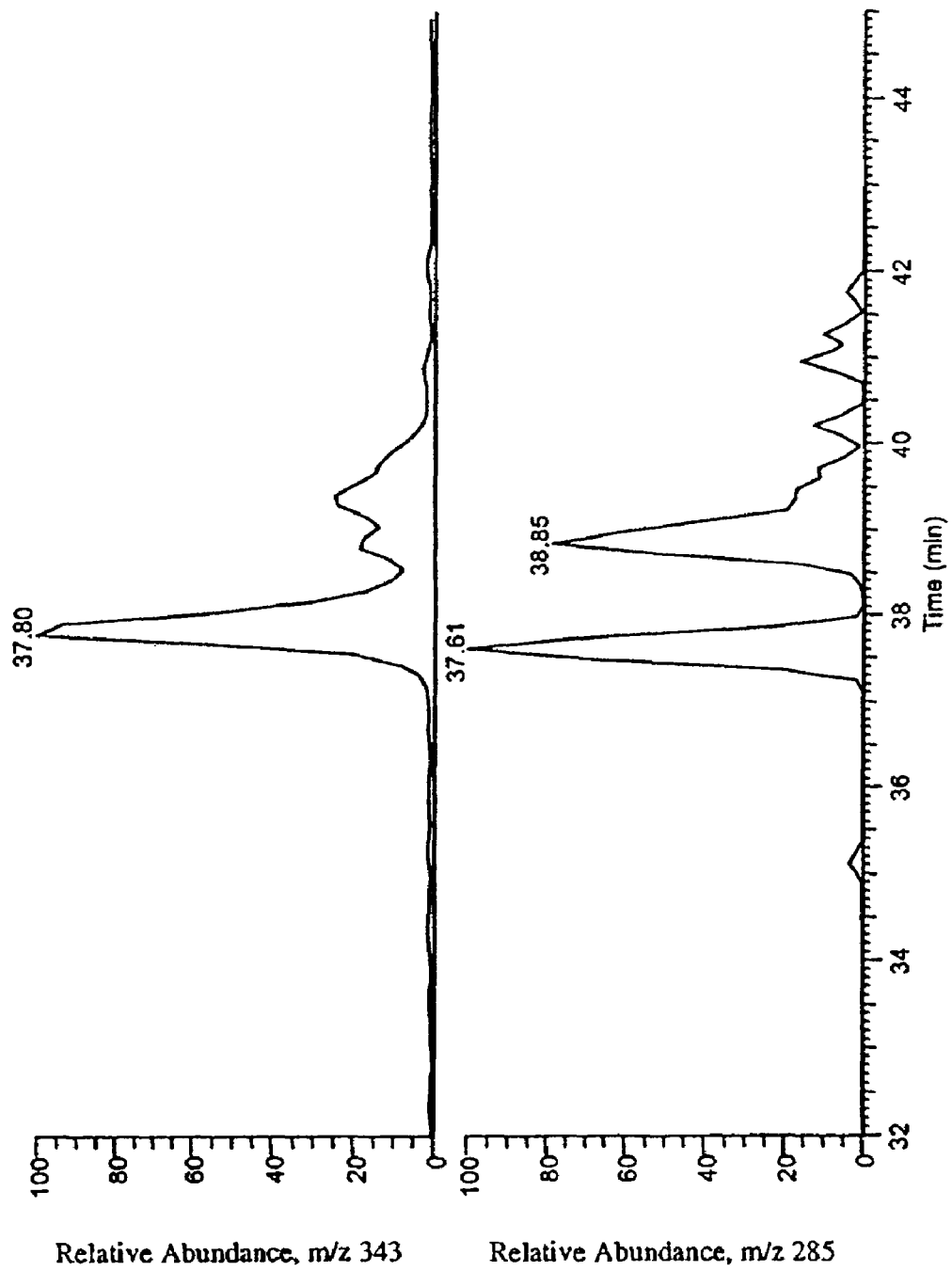
Figure 15:
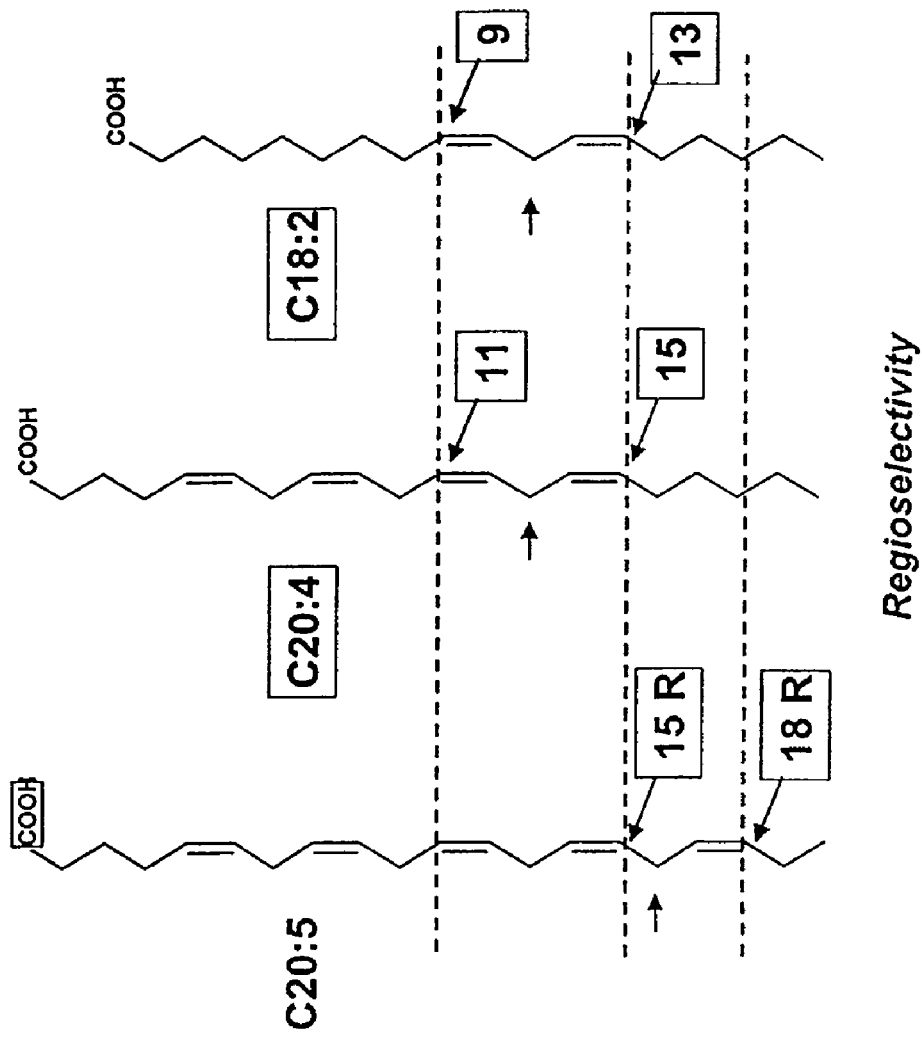
FIG. 15 shows the regioselectivity for oxygenation in ω-3 and ω-6 PUFA by aspirin acetylated-COX-2.

Because COX-2-NSAID-dependent oxygenation (e.g., 18R and 15R) led to bioactive compounds in vivo that block PMN transendothelial migration and infiltration, the findings provide a basis for novel mechanism of action of NSAIDs and dietary ω-3 supplementation, namely the generation of endogenous functional arrays of lipid signals (Table 1 and FIGS. 4 and 7) that could, by dampening key events in microinflammation, mediate some of the beneficial actions noted for ω-3 therapies in human trials. In this context, 13-HODE, a recognized lipoxygenase product that downregulates platelet-EC interactions (29. Buchanan, M. R., P. Horsewood, and S. J. Brister. 1998. Regulation of endothelial cell and platelet receptor-ligand binding by the 12- and 15-lipoxygenase monohydroxides, 12-, 15-HETE and 13-HODE. *Prostaglandins Leukot. Essent. Fatty Acids* 58:339-346.), is also generated by COX-2 (Table 1 and 2) and joins as does DHA (C22:6) (FIGS. 10A-10L) this pathway array and class of mediators (FIG. 12). DHA was also converted to novel reaction products (FIG. 13). In addition, ASA treatment of COX-2 gave different ratios of C17 versus C13 products (FIGS. 14A-14N). These new COX-2 products are likely to play roles in the brain vasculature where COX-2 and DHA are elevated. Hence these compounds could be used to treat inflammatory disorders in neuronal tissues (i.e., Parkinson's disease, Alzheimer's disease, etc.). Hence, it has been surprisingly discovered that COX-2 interactions with NSAIDS lead to novel oxygenations of a wide range of lipid precursors to produce bioactive compounds as illustrated in FIG. 15 and can be used in therapeutic treatment.

As inappropriate inflammatory responses are now recognized as contribution to cardiovascular disease (Ridker, P. M., M. Cushman, M. J. Stampfer, R. P. Tracy, and C. H. Hennekens. 1997. Inflammation, aspirin, and the risk of cardiovascular disease in apparently healthy men. *N. Engl. J. Med.* 336:973-979.) as well as in clinical syndromes where PMN-mediated tissue injury is important (Reference 11), the identification of these novel W-3 PUFA processing pathways evoked by cell-cell interactions and the unexpected impact of NSAIDs opens new avenues for considering the potential clinical protection provided by ω-3 PUFA-based supplementation and mechanisms to generate potent local endogenous mediation that control microinflammation (FIGS. 4-11). Moreover, the present invention provides a basis to circumvent unwanted effects of current antiinflammatory therapies as well as potential biochemical indices and/or markers of effective dietary ω-3 supplementation.

TABLE I

Hydroxy Compounds Generated from PUFA and Recombinant Human COX-2 with ASA or a Selective COX-2 Inhibitor

| PUFA | NSAID | Hydroxy-containing compounds (ng/incubation) | | |
|---|---|---|---|---|
| | | ω-2 | ω-5 | ω-9 |
| | | | 13-HODE | 9-HODE |
| C18:2 | ASA | — | 2.9 ± 0.6 | 25.2 ± 17.8 |
| C18:2 | Vehicle alone | — | 55.0 ± 18.7 | 243.0 ± 68.6 |
| | | | 15R-HETE | 11R-HETE |
| C20:4 | ASA | — | 234.0 ± 112.5 | 1.4 ± 1.6 |
| C20:4 | Vehicle alone | — | 11.5 ± 8.2 | 1.8 ± 1.0 |
| C20:4 | Selective Inhibitor | — | 5.5 ± 0.8 | 0.9 ± 0.1 |
| | | 18R-HEPE | 15R-HEPE | 11R-HEPE |
| C20:5 | ASA | 16.2 ± 3.3 | 16.8 ± 5.8 | 5.4 ± 3.3 |
| C20:5 | Vehicle alone | 7.0 ± 3.3 | 17.9 ± 5.2 | 40.7 ± 10.3 |
| C20:5 | Selective Inhibitor | 5.8 ± 2.6 | 0.0 ± 0.6 | 0.0 ± 0.3 |

Results are the mean ± SEM, 3. The selective COX-2 Inhibitor NS398 was used at 100 uM. All products were extracted, identified, and quantitated using Internal standards and LC/MS/MS. Compounds of interest are shown in bold type.

TABLE 2

NSAID - Human Recombinant COX 2 (Conversion of n-3 C20:5)

| NSAID | 18R-HEPE | 15R-HEPE | 11R-HEPE |
|---|---|---|---|
| ASA | 12.2 +/− 4.6 | 8.0 +/− 5.6 | 5.5 +/− 2.3 |
| Indomethacin | 3.0 +/− 1.4 | 2.6 +/− 1.4 | 3.3 +/− 1.8 |
| Acetaminophen | 5.5 +/− 2.4 | 4.6 +/− 1.2 | 6.7 +/− 3.0 |
| COX-2 alone | 18.3 +/− 11.2 | 42.0 +/− 23.8 | 90 +/− 43.0 | values are the mean amount in ng +/− SEM, n = 3

EXPERIMENTAL

Materials and Methods

Zymosin, hematin, NADPH, and ASA were from Sigma-Aldrich. EPA (Cayman Chemical) and other synthetic standards, hydroxy fatty acids, and intermediates used for identification were purchased from Cascade Biochem Ltd. *Bacillus megaterium* was from American Type Culture Collection. Materials used in liquid chromatography random mass spectrometry (LC/MS/MS) analyses were from vendors given in (20. Gronert, K., C. B. Clish, M. Romano, and C. N. Serhan. 1999. Transcellular regulation of eicosanoid biosynthesis. In Eicosanoid Protocols. E. A. Lianos, editor. Humana Press, Totowa, N.J. 119-144).

Human PMNs were freshly isolated from venous blood of healthy volunteers (that declined taking medication for 2 wk before donation; Brigham and Women's Hospital protocol no. 88-02642) by Ficoll gradient and enumerated. Human umbilical vein or microvascular ECs (HUVECs or HMVECs, respectively) were cultured for transendothelial migration (Reference 10), HMVEC monolayers (one, two, or three passages) were seeded (~$2\times10^5$ cells/cm$^2$) on polycarbonate permeable supports precoated with 0.1% gelatin for incubations with NSAIDs and PUFA.

Inflammatory exudates were initiated with intrapouch injection of TNF-α (R&D Systems) into 6 d dorsal air pouches with (Reference 16) 6-8-wk-old male FVB mice (fed standard rodent diet 5001 containing 0.26% n-3 fatty acids) followed by ASA (500 µg) at 3.5 h and 300 µg C20:5/pouch at 4 h. At 6 h, pouches were lavaged (3 ml saline), and exudate cells were enumerated and activated 94 µM $A_{23187}$, 37° C., 20 min). Inhibition of TNF-α-stimulated (100 ng/pouch, FVB strain) PMN infiltration with intravenous tail injection of either 18R-hydroxyeicosapentaenoic acid (HEPE), 5,12,18R-HEPE, or 15-epi-LXA$_4$ analogue was determined (Reference 16) with pouch lavages taken at 4 h.

Specific [$^3$H]LTB$_4$, (NEN Life Science Products) binding was performed with human embryonic kidney (HEK)293 cells stably transfected with human LTB$_4$ receptor (Chiang, N., K. Groner, C. B. Clish, J. A. O'Brien, M. W. Freeman, and C. N. Serban. 1999, Leukotriene B$_4$ receptor transgenic mice reveal novel protective roles for lipoxius and aspirin-triggered lipoxins in reperfusion. *J. Clin. Invest.* 104:309-316). Human recombinant COX-2 (a gift from Dr. R. A. Copeland, DuPont Merck, Wilmington, Del.) was overexpressed in 5/9 insect cells (American Type Culture Collection) with microsomal fractions (~8 µl) suspended in Tris (100 mM, pH 8.0) as in Reference 21. George, H. J., D. E. Van Dyk, R. A. Straney, J. M. Trzaskos, and R. A. Copeland. 1996. Expression purification and characterization of recombinant human inducible prostaglandin G/H synthase from baculovirus-infected insect cells. *Protein Expres. Purif.* 7:19-26. NSAIDs were incubated (i.e., ASA ~1M) at 37° C. for 30 min before addition of PUFA (20 µM), and conversions were also monitored using 1-$^{14}$C-labeled C20:4 (See FIGS. 2A and 2B) or C20:5 (NEN Life Science Products) (See FIGS. 2C and 2D).

For biogenic synthesis of intermediates and reference compounds, *B. megaterium* was grown in Bacto Nutrient Broth (Fisher Scientific) at 30° C. with shaking. To prepare standards for 18R-HEPE, a biogenic synthesis was used with *B. megaterium* sonicates incubated with NADPH (2 mM) and C20:5 (EPA) (330 µM) in 2 M Tris buffer. pH 8.1. Similar conditions were employed to convert LTB$_5$ (15 µM) to novel products; see Results. Incubations were extracted with deuterium-labeled internal standards (15-HETE and C20:4) for LC/MS/MS analysis using a Finnigan LCQ equipped with a LUNA C18-2 (150×2 mm; 5 µM) column and a rapid spectra scanning UV/Vis detector. Also, a Chiralcel CB-H column (J. T. Baker) was used to determine R and S alcohol configurations of monohydroxy-PUFA using isocratic (hexane/isopropanol 96:4 vol/vol). Detailed procedures for isolation, quantification, and structural determination of lipid-derived mediators were recently reported and used here essentially as described for the elucidation of the novel products.

Preparation of Hydroxy-DHA Compounds:

Hydroxy-DHA compounds were prepared in vitro using recombinant COX-II, both in the presence and absence of aspirin acetylation. Briefly, an incubation mixture was prepared using recombinant human COX-II that was purified as a membrane preparation from SF9 cells expressing the enzyme. The enzyme was suspended in 400 µl of 1 M Tris buffer (pH 8.0) containing 5 mM phenol. For aspirin acetylation of COX-II, aspirin (2 mM) was added to the mixture and incubated at 37° C. for 30 minutes. DHA (5 µM) was then added and the incubated for 5 minutes at 37° C. The reaction was stopped with the addition of 400 µl of chilled methanol. The products were then extracted using solid phase extraction cartridges (SepPak C18).

The novel DHA compounds, 13-hydroxy-DHA, 14-hydroxy-DHA, 16-hydroxy-DHA, 17-hydroxy-DHA, 19-hydroxy-DHA or 20-hydroxy-DHA, have potencies equivalent to those described above for the compounds derived from EPA, i.e., for example, similar to those results depicted in FIGS. 9A and 9C.

Those skilled in the art will know, or be able to ascertain, using no more than routine experimentation, many equivalents to the specific embodiments of the invention described herein. These and all other equivalents are intended to be encompassed by the following claims. All publications and references cited herein, including those in the background section, are expressly incorporated herein by reference in their entirety.

What is claimed is:

1. A pharmaceutical composition comprising a pharmaceutically acceptable carrier and a compound having the formula:

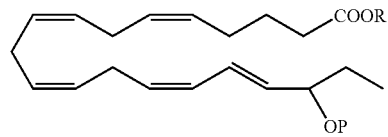

wherein R is a hydrogen atom, or a pharmaceutically acceptable salt or ester thereof, and wherein P is a hydrogen atom or a protecting group.

2. The composition of claim 1, wherein P is H.
3. The composition of claim 2, wherein R is H.
4. The composition of claim 1, wherein the C-18 carbon has an R configuration.
5. The composition of claim 3, wherein the C-18 carbon has an R configuration.

* * * * *